(12) United States Patent
Butler

(10) Patent No.: US 9,943,432 B1
(45) Date of Patent: Apr. 17, 2018

(54) ENERGY RETURN ORTHOTIC SYSTEMS

(71) Applicant: Barry A. Butler, Owatonna, MN (US)

(72) Inventor: Barry A. Butler, Owatonna, MN (US)

( * ) Notice: Subject to any disclaimer, the term of this patent is extended or adjusted under 35 U.S.C. 154(b) by 0 days.

(21) Appl. No.: 15/495,380

(22) Filed: Apr. 24, 2017

(51) Int. Cl.
*A61F 5/01* (2006.01)
*A43B 7/14* (2006.01)
*A43B 13/38* (2006.01)

(52) U.S. Cl.
CPC ............ *A61F 5/0127* (2013.01); *A43B 7/141* (2013.01); *A61F 5/0102* (2013.01); *A43B 13/386* (2013.01)

(58) Field of Classification Search
CPC ................ A61B 5/1038; A61B 5/6807; A61B 2560/0257; A61B 2562/0219; A43B 13/386
See application file for complete search history.

(56) References Cited

U.S. PATENT DOCUMENTS

| | | | | |
|---|---|---|---|---|
| 5,701,685 A * | 12/1997 | Pezza | ..................... | A43B 13/18 36/27 |
| 5,766,265 A * | 6/1998 | Phillips | ..................... | A61F 2/60 623/52 |
| 6,226,901 B1 * | 5/2001 | Rosen | .................. | A43B 7/1465 36/159 |
| 6,397,496 B1 * | 6/2002 | Seymour | .................. | A43B 5/00 36/27 |
| 6,942,704 B2 * | 9/2005 | Sulprizio | .................. | A61F 2/66 623/52 |
| 8,808,395 B2 * | 8/2014 | Townsend | ................. | A61F 2/60 623/47 |
| 9,480,303 B2 * | 11/2016 | Barnes | ................. | A43B 13/183 |
| 2005/0126039 A1 * | 6/2005 | LeVert | ................. | A43B 7/1425 36/27 |
| 2006/0236564 A1 * | 10/2006 | Allard | ....................... | A61F 5/14 36/140 |
| 2009/0013556 A1 * | 1/2009 | Nishiwaki | ............ | A43B 13/181 36/28 |
| 2010/0175279 A1 * | 7/2010 | Segel | ....................... | A43B 7/20 36/145 |
| 2011/0009982 A1 * | 1/2011 | King | ..................... | A43B 7/1425 623/53 |
| 2011/0054358 A1 * | 3/2011 | Kim | ..................... | A61B 5/1038 600/592 |
| 2014/0000125 A1 * | 1/2014 | Butler | .................. | A43B 13/386 36/43 |
| 2014/0059895 A1 * | 3/2014 | Arciuolo | .................. | A43B 7/00 36/173 |

* cited by examiner

*Primary Examiner* — Sean Dougherty
(74) *Attorney, Agent, or Firm* — Fox Rothschild LLP

(57) ABSTRACT

A plurality of orthotic systems are provided. One bi-layer system is constructed from a single sheet of fabric that is molded into two layers. One tri-layer system includes a base layer; a mid-layer; and an upper layer. The upper layer is joined to the mid-layer and the mid-layer is joined to the base layer. The coupling of the base layer, the mid-layer and the upper layer create a rear spring section, a mid-spring section and a front spring section in which the upper layer is suspended over the mid-layer and the heel portion is suspended on the proximal heel end of the base layer.

14 Claims, 51 Drawing Sheets

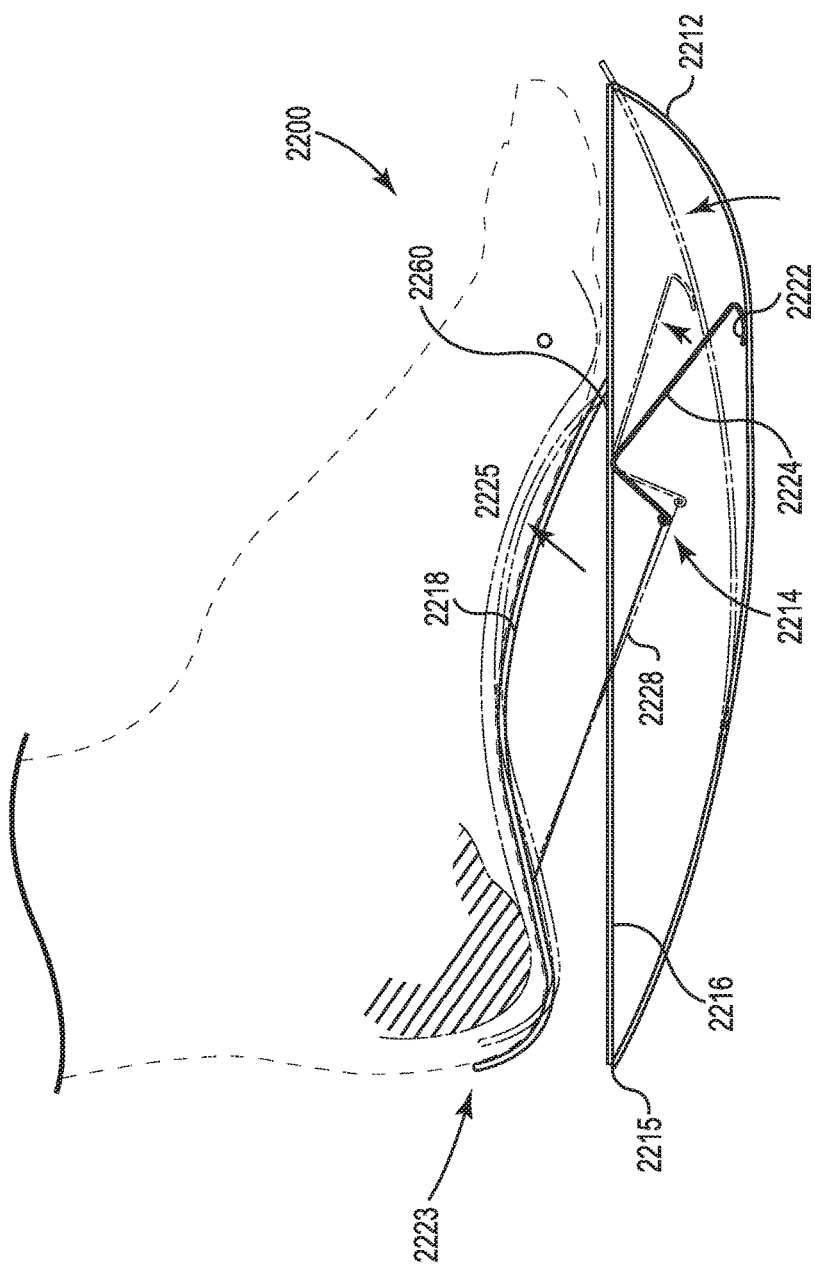

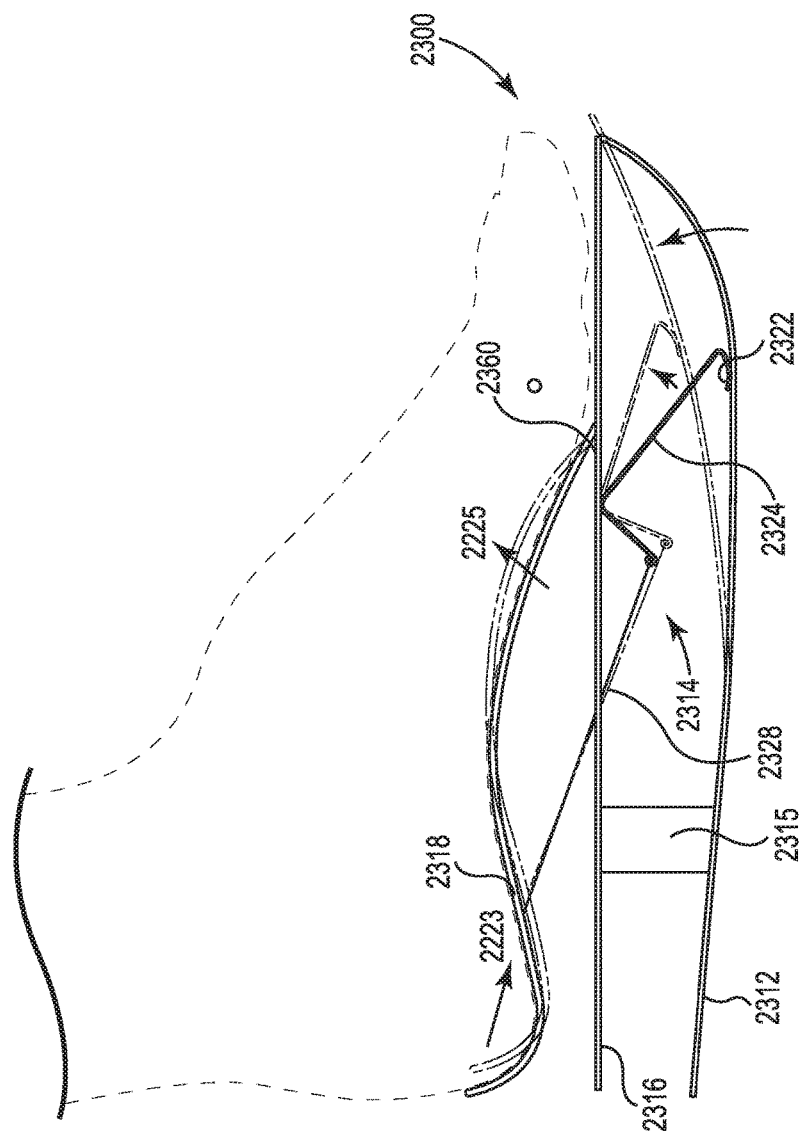

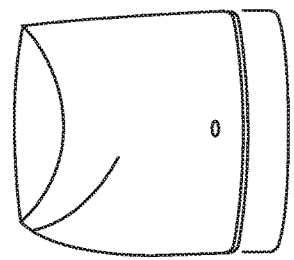
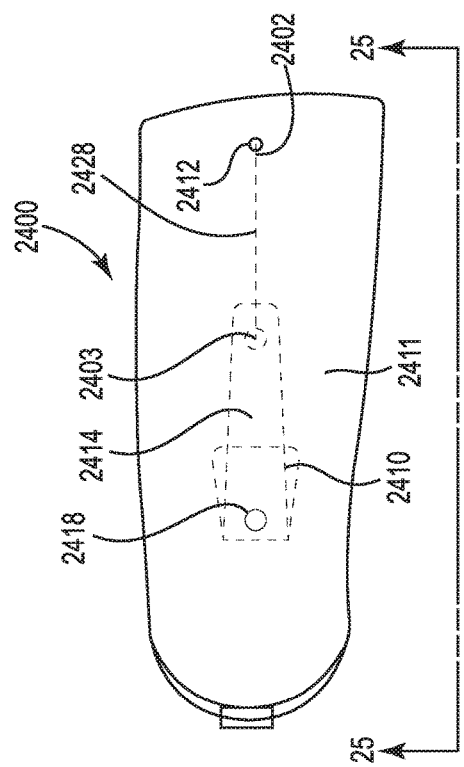
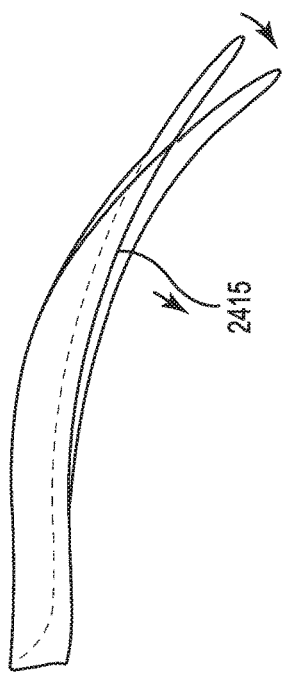

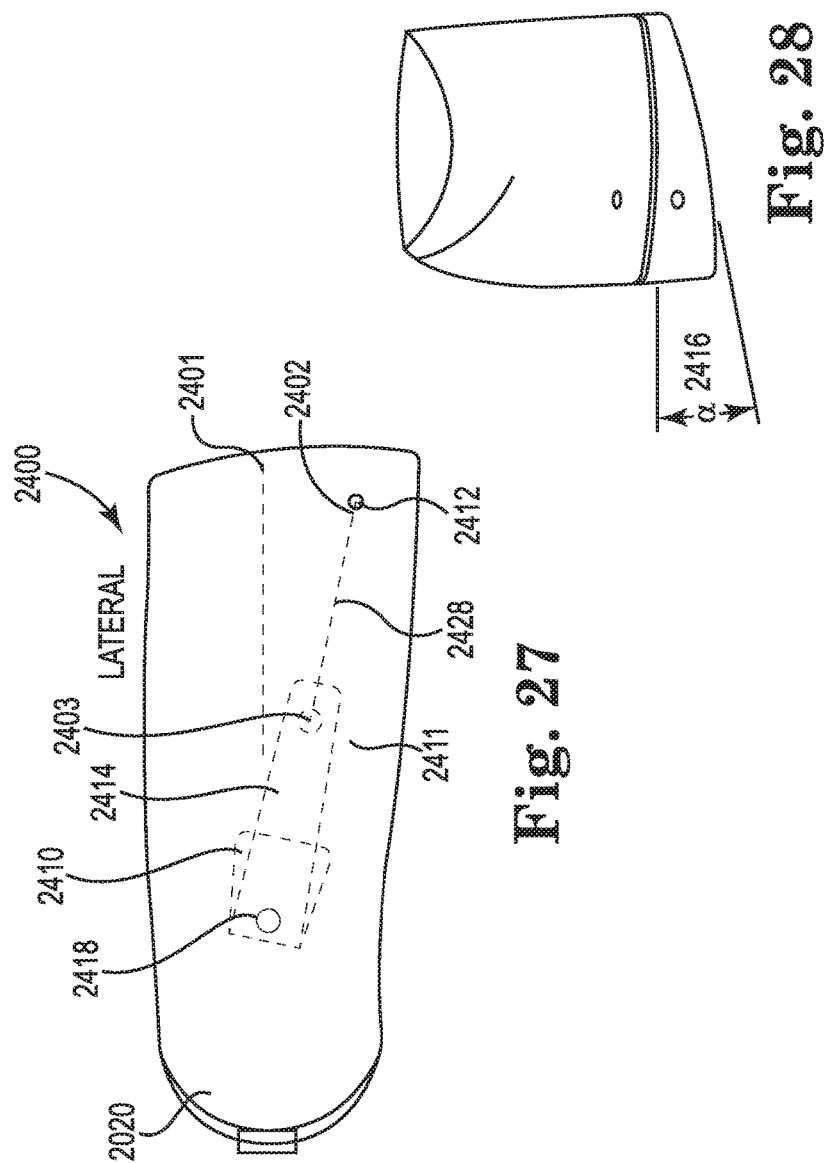

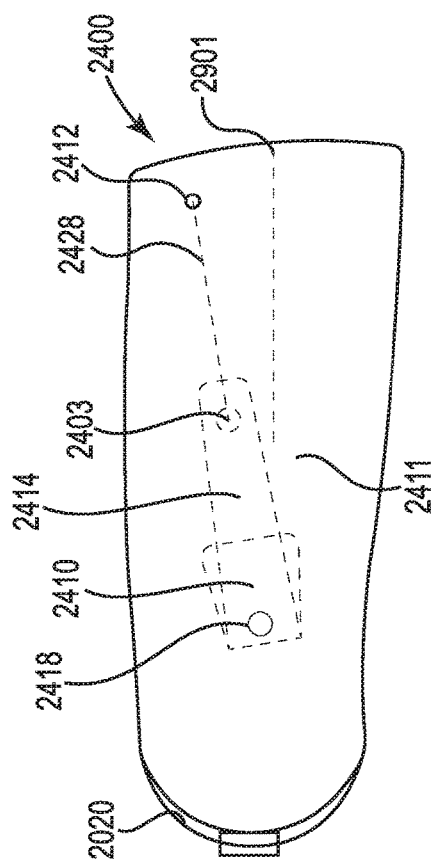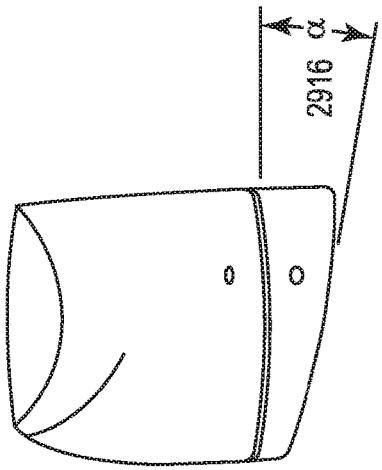

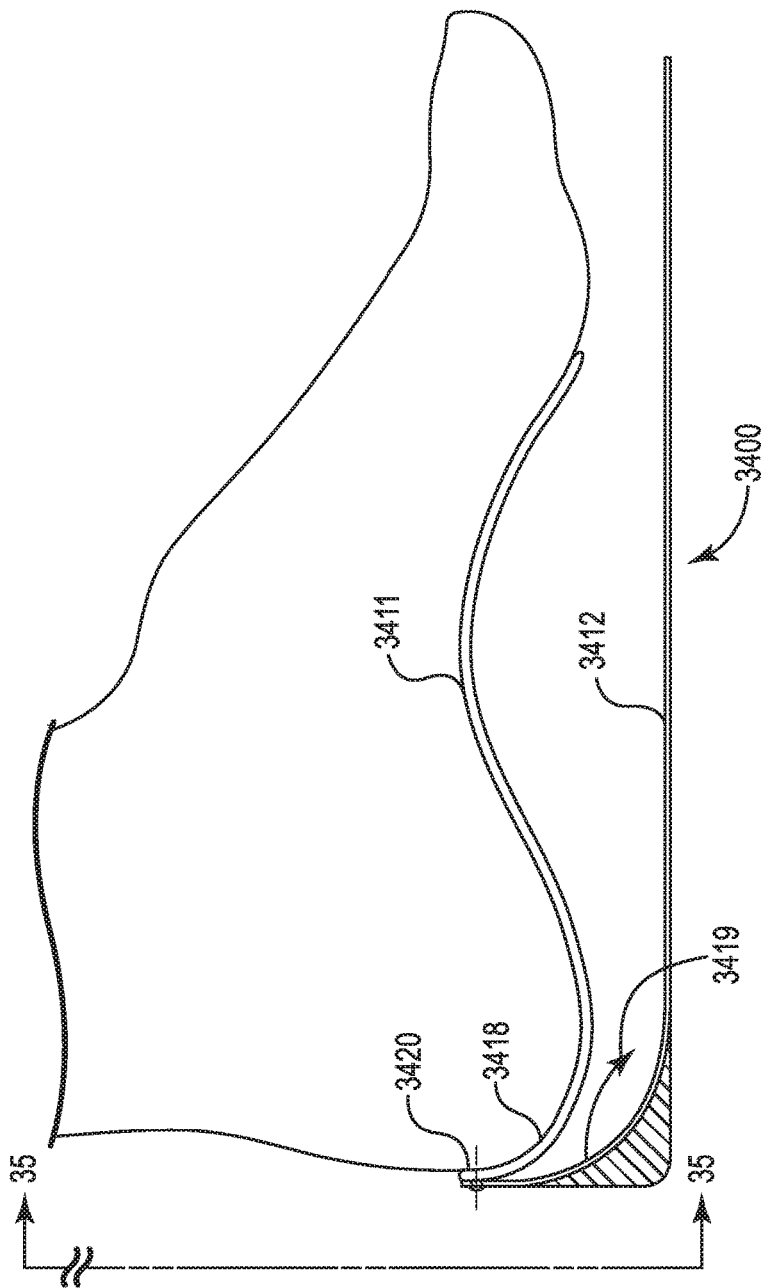

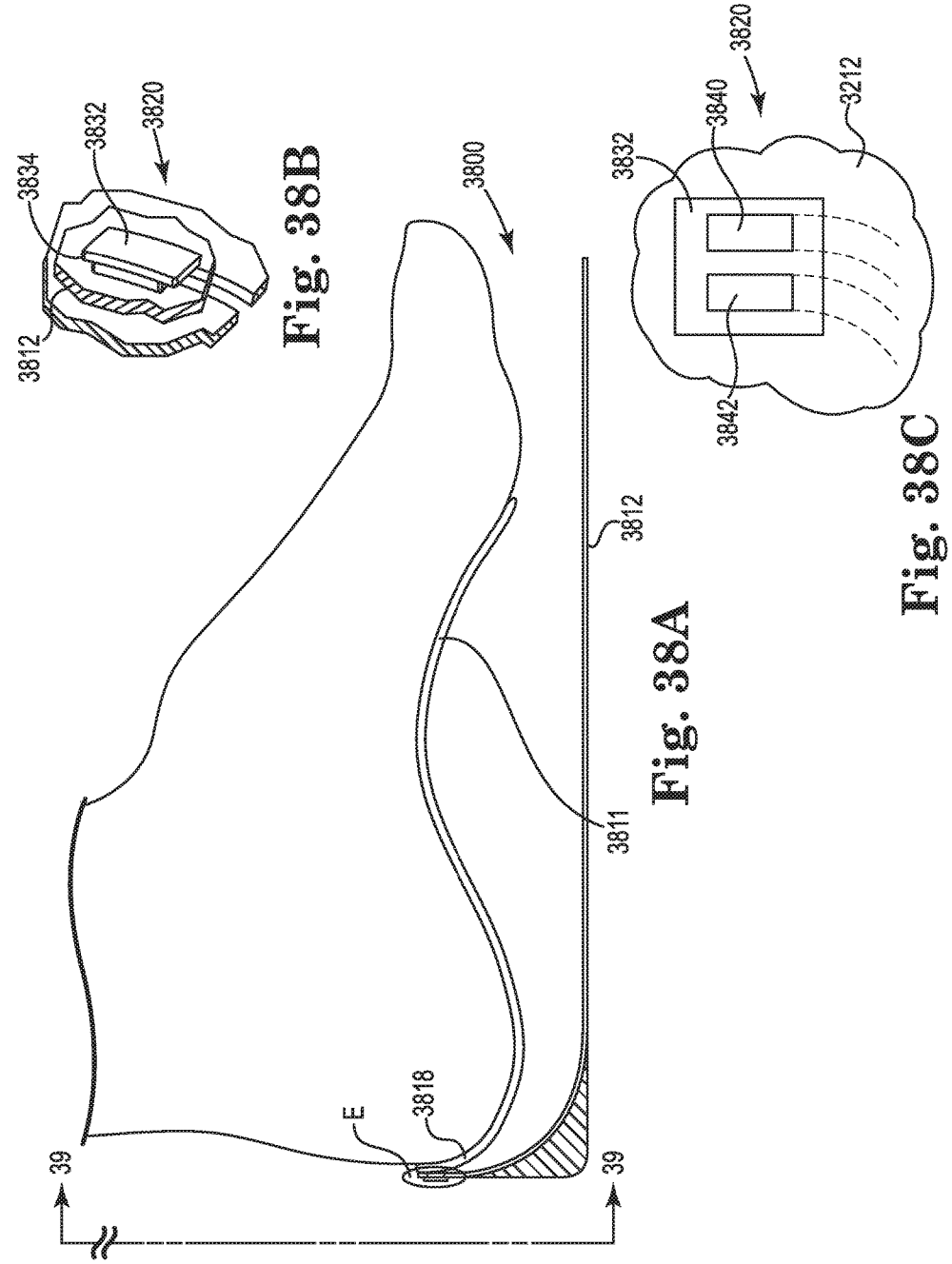

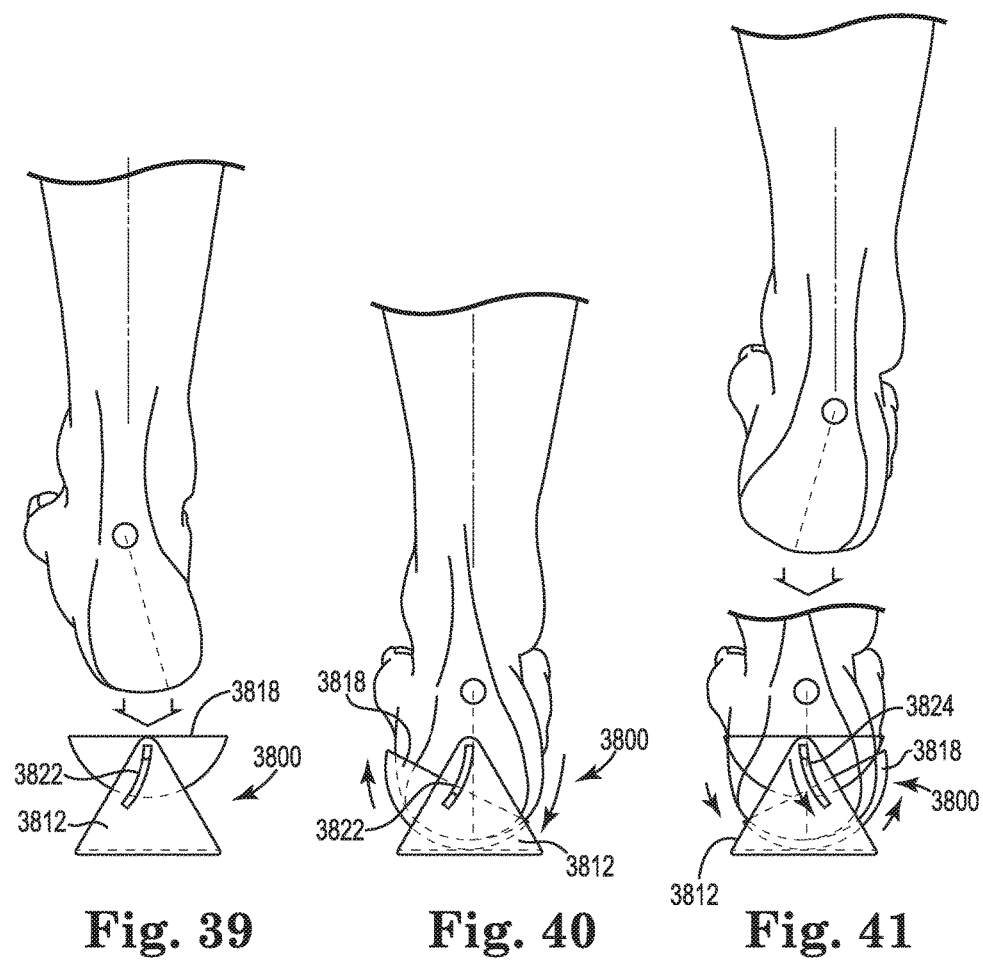

ENERGY RETURN ORTHOTIC SYSTEMS

FIELD OF THE INVENTION

The invention relates generally to orthotic systems that are configured to absorb energy and return it to an individual wearer's foot.

BACKGROUND OF THE RELATED ART

Walking and running can be defined as methods of locomotion involving the use of the two legs, alternately, to provide both support and propulsion, with at least one foot being in contact with the ground at all times. While the terms gait and walking are often used interchangeably, the word gait refers to the manner or style of walking, rather than the actual walking process. The gait cycle is the time interval between the exact same repetitive events of walking.

The defined cycle can start at any moment, but it typically begins when one foot contacts the ground and ends when that foot contacts the ground again. If it starts with the right foot contacting the ground, then the cycle ends when the right foot makes contact again. Thus, each cycle begins at initial contact with a stance phase and proceeds through a swing phase until the cycle ends with the limb's next initial contact. Stance phase accounts for approximately 60 percent, and swing phase for approximately 40 percent, of a single gait cycle.

Hard surfaces in modern human environments have changed the forces encountered by the human musculoskeletal system during the gait cycle as compared to the forces which it evolved to sustain. Impact energies from such surfaces enter the body through boney and dense tissues and through soft and fatty tissues. Such impact energy frequently causes physical damage leading to injury, in particular injury of the foot. At times, this type of physical injury can be treated by an orthotic insert.

Functional orthotic inserts may be placed in a shoe either on top of or in place of the insole to correct foot alignment and side-to-side movement during standing, walking, running to influence the orientation of the bones in a human foot and to influence the direction and force of motion of the foot or parts of the foot. Orthotics thereby decrease pain, not only in the foot, but also in other parts of the body such as the knee, hip and lower back. They can also increase stability in an unstable joint and prevent a deformed foot from developing additional problems. However, conventional devices are not dynamic as designed. Conventional orthotic devices typically include a shimmed, rigid post and as a result, dynamic adjustments to the foot during the gait cycle cannot be done. For example, adjustments such as making the foot tip out further, making the foot tip in further, raising the heel, raising the ball of the foot, and the like cannot be accomplished with conventional devices dynamically during the gait cycle.

Other causes of injury to the foot relate to underlying pathological disease states, such as by way of example, diabetes. Diabetes is a chronic disease that affects up to six percent of the population in the U.S. and is associated with progressive disease of the microvasculature. Complications from diabetes include not only heart disease, stroke, high blood pressure, diabetic retinopathy but also in particular diabetic neuropathic foot disease.

Diabetic neuropathic foot disease typically results in the formation of ulcers which commonly result from a break in the barrier between the dermis of the skin and the subcutaneous fat that cushions the foot during ambulation. This rupture may lead to increase pressure on the dermis. While there are devices and methods that purport to prevent plantar ulcer formation in a diabetic patient there are no orthotic devices on the market that treat the ulcer with dynamic offloading after formation.

Other types of injury to the foot include fractures, pressure sores, surgical sites and overuse injuries. Patho-mechanical foot dysfunctions include supination and pronation pathologies.

Therefore, what is needed are orthotic systems that can be used remedially to correct deformities resulting from physical and other injuries to the foot. What is also needed are dynamic orthotic systems that can be used therapeutically to address underlying pathologies and patho-mechanical foot dysfunctions to accurately and precisely position the foot throughout the gait cycle in order to promote proper function and alignment and mitigate excessive forces. In particular, what is needed is a dynamic orthotic suspension system that addresses foot pathologies that cause systemic pathologies such as ankle, knee and hip misalignment.

BRIEF SUMMARY OF THE INVENTION

The aforementioned problems are addressed by the orthotic system in accordance with the invention. In some aspects the orthotic systems comprise "The Artificial Foot and Ankle" and are designed as the ultimate mobile adaptor to meet the ever changing shape of the environment on which we ambulate. In some aspects the orthotic system in accordance with the invention is a 3D biomechanics controlling suspension platform that allows infinite force alteration and dynamic force redistribution. In some aspects a 3D biomechanics controlling suspension platform that allows range of motion control and pathological force mitigation is disclosed.

In other aspects the orthotic system may be coupled with a computer having video analysis of motion software and capabilities and sensing mechanisms that allows the tracking of foot pathology and the ability to change its progression over the course of time by modifying the orthotic as foot function changes or pathology progresses. Coupling the orthotic system with Vicom and sensing mechanisms will likely improve and/or restore balance when the platform is real-time controlled in conjunction with sensing feedback. Controlling balance artificially with such mechanisms will prevent falls which lead to fractures and gait instability as well as sprains and other pathology resulting from instability. The sensing mechanism may include one or more sensors operably coupled to the orthotic and capable of transmitting data regarding gait, stance and other movements made during the gait cycle to the computer wherein the computer includes video analysis of motion software for analyzing the sensing data and providing visual feedback on a display screen regarding existing pathologies and required corrections.

In some aspects, the orthotic system includes at least one sensor positioned on or near said orthotic that senses movement and/or pressure during the gait cycle; a knowledge base that provides data on a plurality of foot pathologies and a plurality of information regarding a normal foot and/or normal gait cycle; a processing device in operable communication with said at least one sensor and said knowledge base, said processing device operative to (a) receive data from said at least one sensor related to the gait cycle of an individual; (b) compare said data received from said at least one sensor to the plurality of foot pathologies in said knowledge base; (c) determine a therapeutic correction to the orthotic based on the plurality of information regarding a normal foot and/or normal gait cycle to improve the gait cycle of the individual; and (d) outputting a visual representation of said correction to the individual.

In some aspects, the orthotic system is an interventional platform for the treatment of orthopedic pathology throughout the body, such as ankle, knee, spine and hip pathologies that relate to gait cycle biomechanics. In some aspects, tracking of pathologic forces coupled with periodic fine tuning of the suspension to compensate and maintain proper alignment may change the course of related ankle, knee, spine and hip pathologies and associated pain. In some aspects, the orthotic suspension system comprises a gait altering device that will change the feel of ambulation as presently known, making activity not only more tolerable but more enjoyable and fun. In some aspects the orthotic systems allow for performance enhancing effects that improve the efficiency of ambulation allowing an individual to walk/run farther, faster and longer with the same energy. In some aspects the orthotic systems harness the forces of ambulation and redistribute the forces to improve the efficiency of ambulation.

In some aspects, a multi-layer suspension orthotic or single layer suspension orthotic with any number of possible deflections that create multiple layers is provided. In some aspects the orthotic suspension systems can be passively; static-dynamically or dynamic-dynamically controlled during the gait cycle to control foot, ankle and body biomechanics through the creation of a wave of counter forces to oppose, reduce, and/or amplify those forces naturally occurring during the gait cycle. In some aspects, the orthotic suspension systems may be passively controlled or tuned by interposing material of variable resistance to travel between the layers/deflections such that a desired deviation in travel is obtained that may either offset angulation change, i.e. control movement biomechanics, or alteration in resistance to travel or to control ground reactive pressures.

In some aspects the orthotic systems are static dynamically tunable like a guitar when fixed forces can be applied to layers/deflections, such as segments or rays, to effect angulation change or control ground reactive forces where the amount of force during the gait cycle is fixed.

In some aspects dynamic-dynamically (changing throughout the gait cycle) leverage control of a lever operably coupled to a filament or similar mechanics, such that applied force to the segments/rays or layers/deflections changes during the gait cycle. The force multiplier component of which may create additional performance enhancing characteristics.

In some aspects, the platform could create an inverse wave to oppose the natural rise and fall of pressure during the gait cycle thus leveling pressures and reducing the need for motion induced by the normal forces of the gait cycle.

In some aspects the orthotic systems create an interventional platform for off loading—as in the case of the diabetic foot: uploading with a force multiplier to effect (performance); range of motion management (enhancing reduction); alignment restoration; and biomechanics control.

In some aspects any of the disclosed orthotic systems may be constructed using 3D printing.

Thus, in some aspects of the present invention, the system broadly includes a base layer; a platen; an orthotic and a lever operably coupling the base layer through a pass in the platen. The foregoing elements work together as a system to absorb energy in walking, running and the like and return it to the foot at the proper time and location. The orthotic may comprise a segmented orthotic or a non-segmented orthotic. The lever may include a slide portion and a draw pin or tensioning member that is anchored to the orthotic through the pass in the platen. The orthotic energy system in accordance with the invention controls the energy produced from the gait cycle to deform the orthotic layer in a particular location or in a particular angulation to supinate or pronate the foot. The system may also be adapted to address a variety of orthopedic remedial and therapeutic issues.

Also disclosed is a bi-layer orthotic that therapeutically addresses pronation and supination issues in a patient.

Also disclosed is an air-heel that is a bi-layer orthotic adapted to be cosmetically incorporated in women's shoes that promote proper function and alignment and mitigate excessive forces.

Also disclosed is an orthotic that includes a kick stand that moves medially or laterally to correct supination or pronation.

Traditionally, the heel cup of an orthotic is shimmed by integrally forming the shim in the heel cup, which has the effect of tilting the entire orthotic and foot back to front. Thus the mid-foot and forefoot are potentially misaligned. In the case of varus shim built into the heel cup, the midfoot and forefoot are over supinated and misaligned. In the case of a valgus shim built into the heel cup the mid-foot and forefoot are over pronated and misaligned. To address this problem, an orthotic system is disclosed that includes one or more cut segments that extend from the medial side across to the lateral side. Any of the segments may be positioned medially or laterally to define an area of desired control, for instance the cuts may separate an area under the fifth metatarsal base whereby elevation of this segment may pronate the mid-tarsal joint and simulate peroneal tendon function in a patient who has lost peroneal function due to trauma or stroke, downwardly or upwardly adjusting any desired area between two such cuts could also be used to correct joint or bone structure malalignment created by shimming of another segment of the dynamic orthotic. In the case of a standard custom functional orthotic that is shimmed in four degrees of varus at the rear foot post to improve subtalar joint alignment and treat pathological pronation, the entire orthotic is tipped in this alignment causing further disruption of normal function and alignment of other joints and structures within the foot. The segmental orthotic allows for individual segments to be adjusted independently allowing more finite control of individual segments of the foot or individual structures such that specific pathologies can be better treated with the conservative modality, and better biomechanical control of the foot, ankle, and as a result everything upstream including knees, hips, and back potentially avoiding long term effects of malalignment resulting in orthopedic pathologies, pain and dysfunction leading to procedures such as joint replacement or arthrodesis. A semi-rigid spine, i.e. any non-articulated contiguous portion of semi-rigid material or in some cases a semi-rigid backbone allowing articulated segments to rotate on a central axis runs from a toe portion to a heal portion of the orthotic holds the cut segments in place. The cut segments may articulate upwardly or downwardly depending on the desired anatomical correction.

Also disclosed is a modification of the foregoing wherein the cut segments extend only partially across the orthotic. Functionally, the central area of the orthotic foot bed serves as a spine.

Also disclosed is a tri-layer orthotic that includes three layers of material of varying thicknesses laminated together in a mold with resin, or similar materials, joining the three layers together. Alternatively, those of skill in the art will appreciate that adhesive or other bonding means, such as tape and the like, can be used to bond the layers together. The orthotic may be vacuumed formed and baked to cure the resin and trimmed to appropriate sizes, i.e. size 6, 7, 8, etc. The orthotic may also be trimmed to match the size and contour of the foot of a particular individual user. The tri-layer orthotic may include segments configured to be articulated upwardly or downwardly, as hereinbefore discussed, rays under metatarsals, as shown, and/or one or more apertures in the heel area or anywhere on the orthotic. Those of skill in the art will appreciate that the tri-layer orthotic may also be manufactured using 3D printing as hereinafter described.

Also disclosed is a bi-layer orthotic that is constructed from a single layer or sheet of material. A rear portion of the orthotic functions as a rear spring area that provides suspension to the heel and decelerates heel strike. An arch portion is cut into the orthotic to provide support and lift to the arch area. A front portion may include an optional bi-layer area that provides suspension for the forefoot or ball of the foot similar to the rear spring area. The orthotic may be inserted into footwear and extend the full length of the footwear or stop as shown under the base of the toes or may be the functioning sole of the footwear.

A top cover may be applied to any of the orthotic systems disclosed herein and stretch like a hammock across the articulated areas to further provide suspension to the foot and move support to the perimeter and out from directly beneath the suspended foot.

Those of skill in the art will appreciate that the orthotic systems disclosed herein have broad applications and may be incorporated into diabetic shoes; sports or athletic shoes; every day footwear including women's shoes, boots and the like whether a remedial or therapeutic result is desired without departing form the scope or spirit of the invention.

BRIEF DESCRIPTION OF THE DRAWINGS

For a better understanding of the invention, and to show how the same may be carried into effect, reference will now be made, by way of example, to the accompanying drawings, in which:

FIG. 22 is a side elevational view of a sixth alternate embodiment of the invention in a static position showing the secondary position of selected elements.

FIG. 23 is a side elevational view of a seventh alternate embodiment of the invention showing the secondary position of selected elements.

FIG. 24 is top plan view of an exemplary embodiment of an orthotic in accordance with the invention.

FIG. 25 is a side elevational view taken along line 25-25 of FIG. 24 showing a secondary position.

FIG. 26 is a front elevational view thereof showing the secondary position.

FIG. 27 is a top plan view of a first variation of the subject of FIG. 24 wherein the orthotic is segmented laterally.

FIG. 28 is a front elevational view thereof showing a secondary position and the angle of correction.

FIG. 29 is a top plan view of a second variation of the subject of FIG. 24 wherein the orthotic is segmented medially.

FIG. 30 is a front elevational view thereof showing a secondary position and the angle of correction.

FIG. 34 is a side elevational view of a bi-layer orthotic in accordance with an embodiment of the invention with parts omitted for clarity.

FIG. 38A is a side elevational view of a bi-layer orthotic in accordance with the invention.

FIG. 38B is an enlarged fragmentary pictorial detail taken from the area E of FIG. 38A.

FIG. 38C is an enlarged fragmentary pictorial detail taken from the area E of FIG. 38A showing a modification thereof.

FIG. 39 is a rear elevational view of the orthotic of FIG. 38A taken along line 39-39 and showing a supinated foot requiring correction descending into the orthotic.

FIG. 40 is a rear elevational view thereof showing the therapeutic correction using the bi-layer orthotic of FIG. 38A in accordance with the invention.

FIG. 41 is a rear elevational view similar to that of FIGS. 39 and 40 showing the correction of a pronated foot using the bi-layer orthotic of FIG. 38A in accordance with the invention.

DETAILED DESCRIPTION OF THE INVENTION

Figure 1:
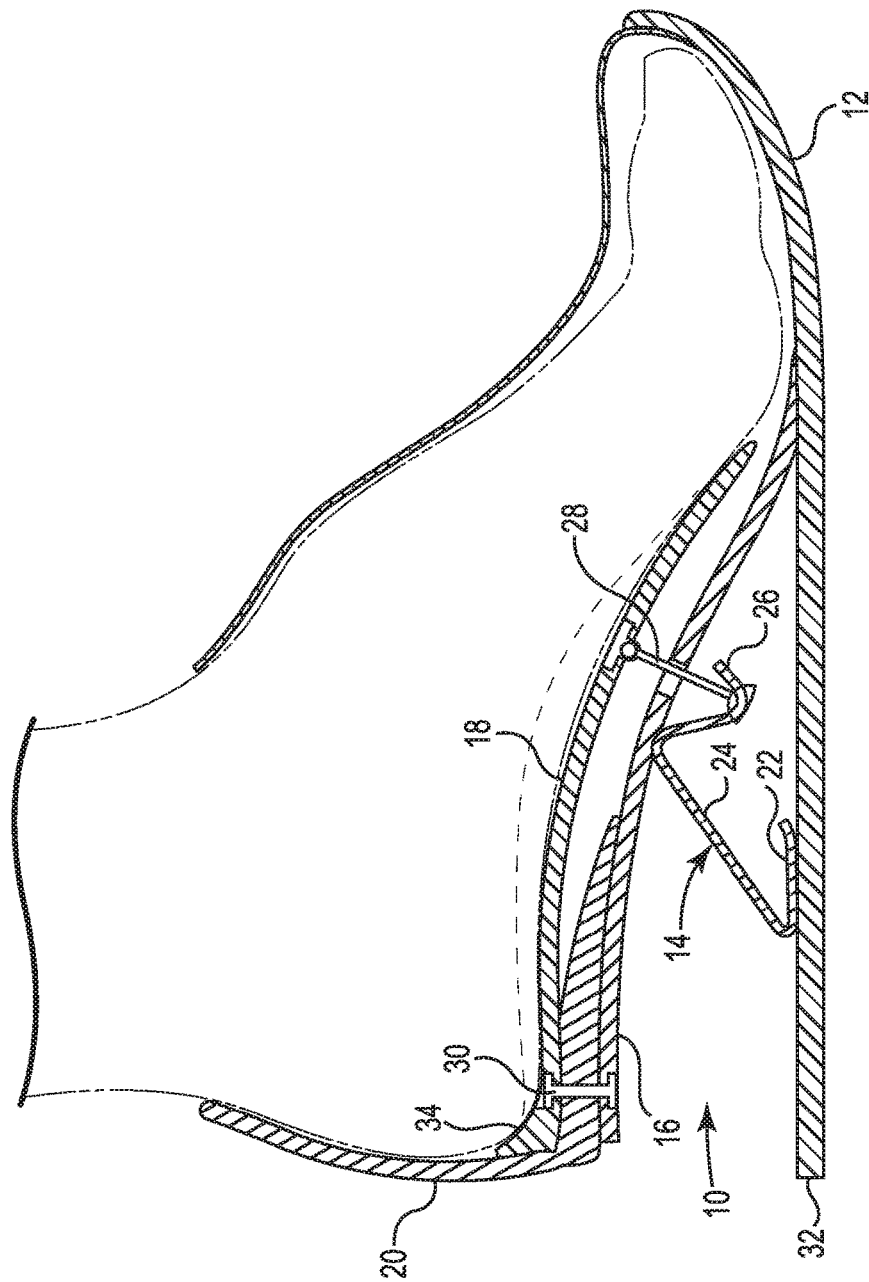
FIG. 1 is a side elevational view of the orthotic energy return system in accordance with the invention with foot shown in phantom dashed lines.

Referring now to FIGS. 1 through 6, a first embodiment of the orthotic energy return system in accordance with the invention is depicted. FIG. 1 illustrates a foot (in phantom lines) at rest wearing the energy return system 10 in accordance with the invention. The energy return system 10 is shown in the unburdened or off-loaded position with the base layer 12 at rest on a surface such as the ground. The energy return system 10 broadly includes base layer 12, lever 14, platen 16 and orthotic 18. Base 12 may be of any length so long as it generally extends from the sole of the foot to the toe region. Base 12 may comprise any material used for the soles of shoes including but not limited to rubber, plastics, polymers, polyurethanes and the like. Lever 14 includes slide 22, angled central portion 24 and angled connecting portion 26. Lever 14 is made from a material that is resilient to allow it to dynamically deform during the gait cycle. Suitable materials that may be utilized for lever 14 include plastics, polymers and resilient metals. Orthotic 18 is also made from a material that is resilient to allow it to dynamically deform during the gait cycle. Suitable materials that may be utilized to construct orthotic 18 include polyolefin; polypropylene, open and closed cell foams and graphites. Platen 16 is desirably made from rigid or semi-rigid materials such as plastics, polypropylene, fiberglass, carbon fiber and other materials known to those of skill in the art.

Tensioning member 28 operably couples lever 14 at angled connecting portion 26 to orthotic 18. Tensioning member 28 is depicted as a pin however those of skill in the art will appreciate that rods, cables, wires, filaments and the like may be substituted for pin 28. Platen 16 may be substantially rigid and is operably coupled to orthotic 18, through heel cup 20, by connecting member 30. Connecting member 30 may comprise pins, rods, wires, filaments and the like. Those of skill in the art will appreciate that connecting member 30 may be eliminated and platen 16 may be indirectly coupled to orthotic 18 by adhesive means or chemical bonding between platen 16 and heel cup 20 and between heel cup 20 and orthotic 18.

The energy return system in accordance with the invention will now be described in operation. Referring now to FIGS. 2-5 the gait cycle and the operation of the energy return system is illustrated. Thus, an understanding of the gait cycle is helpful to the understanding of the operation of the energy return system in accordance with the invention.

The gait cycle begins when one foot contacts the ground and ends when that foot contacts the ground again. Thus, each cycle begins at initial contact with a stance phase and proceeds through a swing phase until the cycle ends with the limb's next initial contact. There are two phases of the gait cycle. Stance phase is the part of the cycle when the primary foot is in contact with the ground and begins with initial contact or heel strike and ends with toe-off. Swing phase occurs when the opposite, second foot is in the air and begins with toe-off and ends with the second heel strike.

Figure 2:
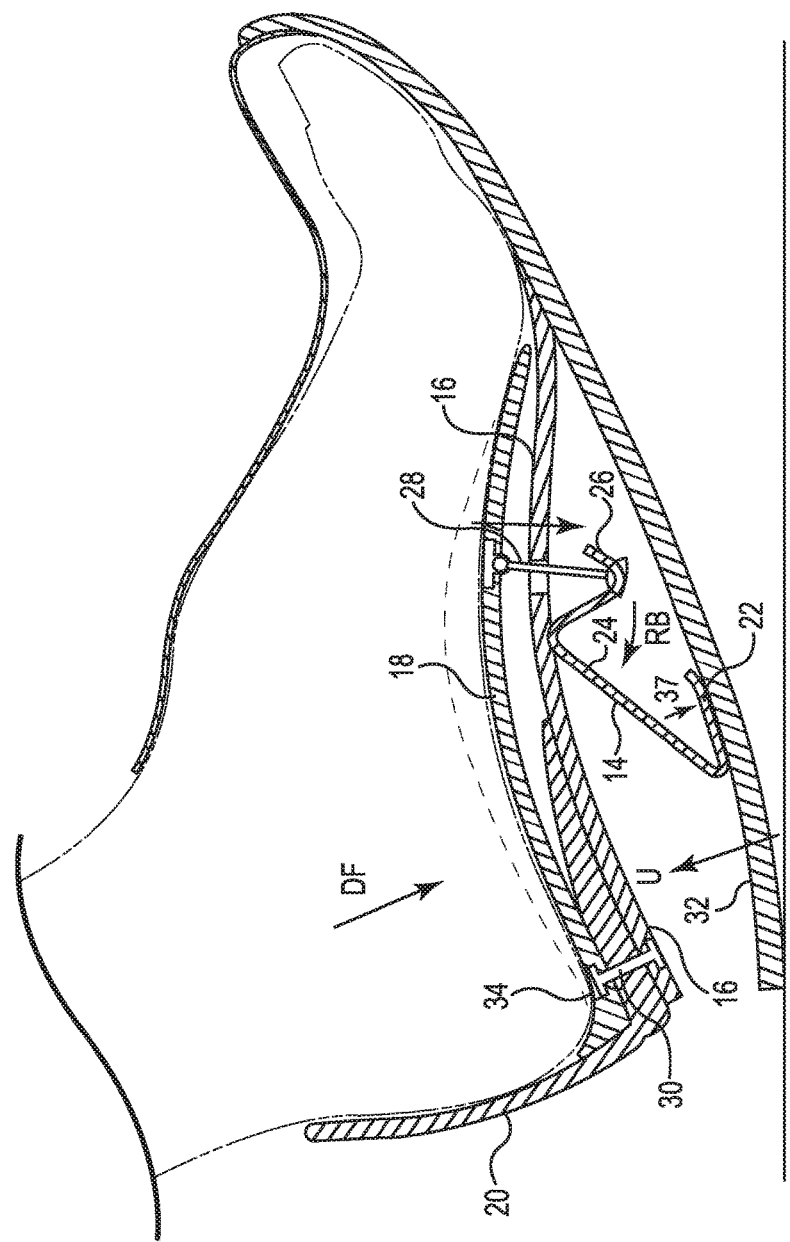
FIG. 2 is a view thereof wherein the subject has initiated the gait cycle.

Referring now to FIG. 2, the loading response begins with initial contact, the instant the primary foot contacts the ground. In a normal gait pattern, the heel of the primary foot contacts the ground first (unless the patient has equines as depicted in alternative embodiment in FIGS. 5-6). The downward force (DF) of the heel causes base layer 12 to deform upwardly toward the heel as noted by arrow U. Angled central portion 24 of lever 14 commences to compress downwardly 37 toward slide 22 as angled connecting portion rotates distally RB toward angled central portion 14 causing the buildup of tension on tensioning member 28. Because angled connecting portion 26 is operably coupled to orthotic 18 by tensioning member 28 the tensioning of tensioning member causes the orthotic to deform downwardly. These motions collectively cause the energy return system in accordance with the invention to load.

Figure 3:
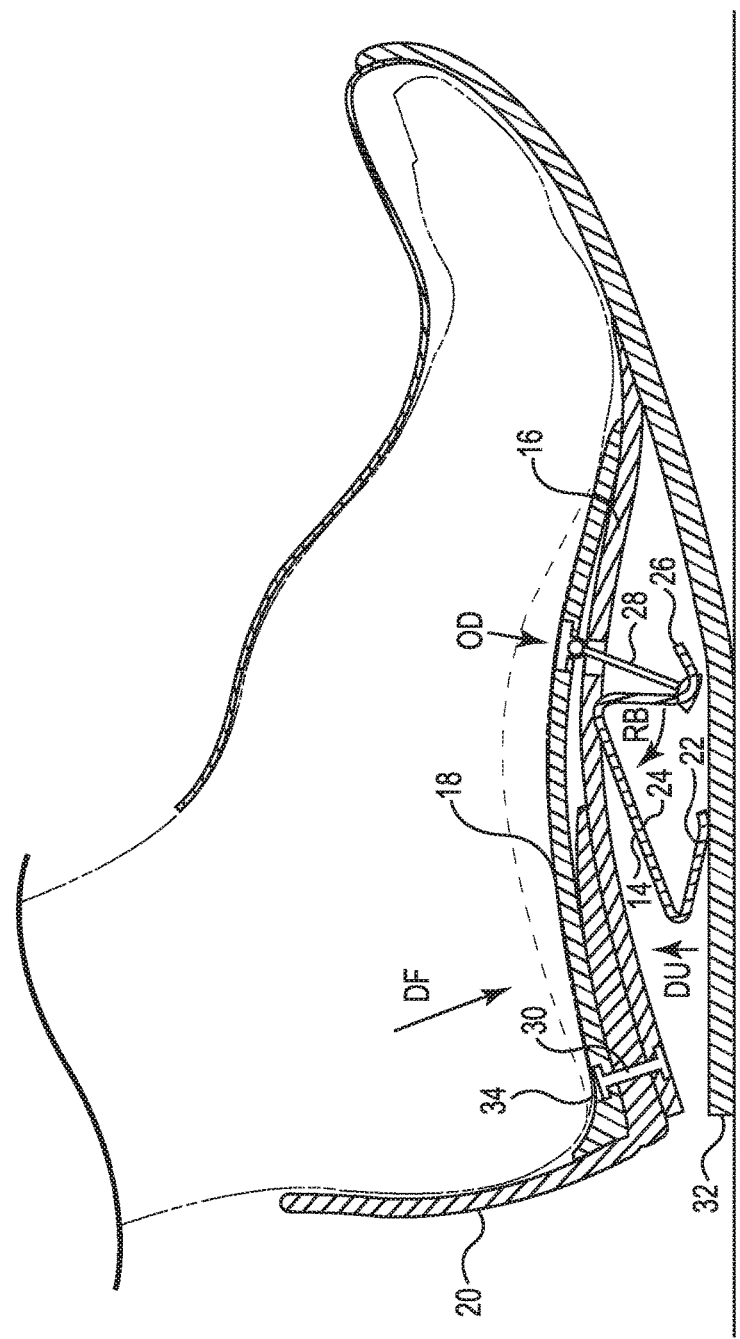
FIG. 3 is a view thereof wherein the foot has advanced in the gait cycle to initial contact with the ground or heel strike.

Referring now to FIG. 3 the downward force of the heel continues to cause base 12 to deform upwardly U toward platen 16. Particularly, angled central portion 24 of lever 14 deforms closer to slide 22 as connecting portion 26 rotates distally RB loading tension member 18 with tension. Tensioning member 18 causes orthotic to continue to move downwardly OD. As can be seen, the arch of the foot is compressed down further than as seen in FIG. 2 and thus more energy is being stored in the orthotic layer 18.

Figure 4:
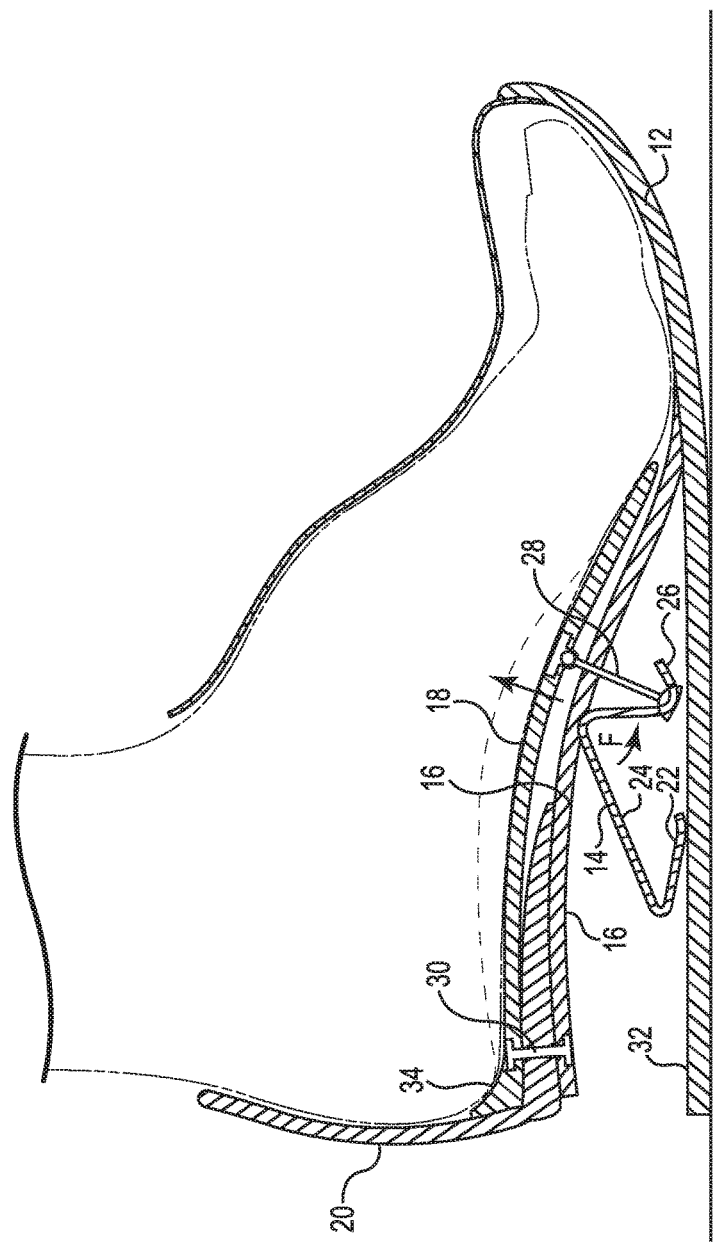
FIG. 4 is a view thereof rebounding from initial contact or heel strike at mid-stance.

Loading response ends with contralateral toe off, when the opposite, second foot leaves the ground (not shown). Midstance begins with contralateral toe off and ends when the center of gravity is directly over the reference foot as seen in FIG. 4. This phase, and early terminal stance, are the only times in the gait cycle when the body's center of gravity truly lies over the base of support. Terminal stance begins when the center of gravity is over the supporting foot and ends when the contralateral foot contacts the ground. During terminal stance, the heel rises from the ground.

Referring now to FIG. 4 the foot is shown at mid-stance as it commences to rotate forward and energy stored in the orthotic 18 combined with the previous deformation of the base 12 begins a rebound effect to the foot along the arch. Slide 22 releases partially from base 12 as angled connecting member 26 rotates forwardly F thus starting to release the tension of tensioning member 28 on orthotic 18.

Pre-swing begins at contralateral initial contact and ends at toe off, at around 60 percent of the gait cycle. Thus, pre-swing corresponds to the gait cycle's second period of double limb support. Initial swing begins at toe off and continues until maximum knee flexion (60 degrees) Occurs.

Figure 5:
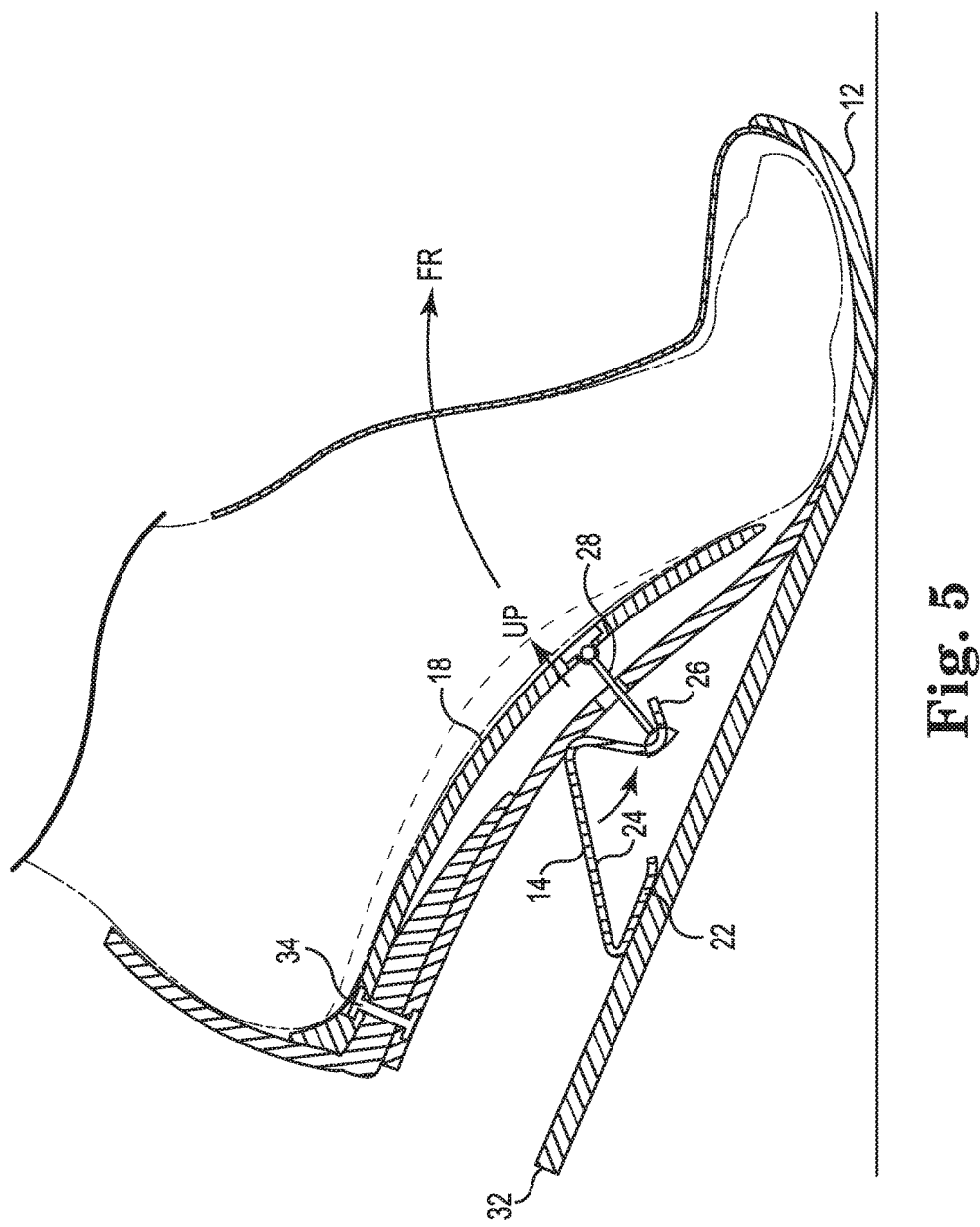
FIG. 5 is a view thereof showing terminal stance with arrow moving toward toe-off or pre-swing phase.

Referring now to FIG. 5 the primary foot is shown at terminal stance moving toward toe-off. In toe-off the foot continues its forward rotation FR and energy stored in the orthotic 18 combined with the base 12 completes the rebounding of energy to the foot along the arch. Downward tension is completely off-loaded from tensioning member 28 and in turn orthotic 18. However, due to the storage of energy in orthotic 18, orthotic 18 presses upwardly UP against arch causing the arch to rise until it reaches the position should in FIG. 1.

Referring again to FIGS. 2-5, the heel strike and the deceleration of the body mass as it impacts the ground will deforms the base 12, flexing it up in the rear, which will then cause lever 14 to lever off the platen 16 and tension the tensioning member 28 which in turn deforms orthotic 18 due to the coupling thereof with tensioning member 28. Orthotic 18 may be coupled in the back (as best seen in FIGS. 2-5) to allow for the tensioning member 18 to dynamically pull the front of the orthotic 18 back towards the fixed point in the rear 34.

Alternatively, orthotic 18 may be operably coupled to platen 16 at a fixed point in the front (as best seen in FIG. 22). If orthotic 18 is fixed at a front point to platen 16 the leverage from flexion of the front of the sole as it bends up would in turn leverage tensioning member 28 and pull the heel portion of the orthotic 18 forward resulting in the base 12 storing energy.

Thus, the constraint of the base 12 is not controlled; rather it is dynamic in that the stored energy is readily disbursable. The base layer 12 is not just deflecting the lever. It also absorbs energy and provides shock absorption at heel strike. The stored energy has a tendency to be destabilizing. Thus, the energy return system in accordance with the invention controls the energy to deform the orthotic 18 in such a way that the treatment of particular foot pathologies is possible. In addition, the energy return system is capable of releasing the energy later in the gait cycle by adjusting the location of the lever front to back and by reversing its direction and/or by lengthening the orthotic to perform a particular function.

Figure 31:
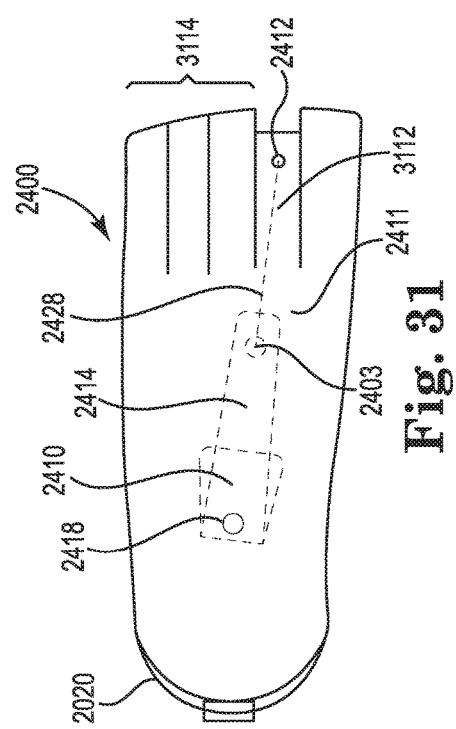
FIG. 31 is a top plan view of an exemplary embodiment of a orthotic in accordance with the invention having all rays segmented.

For example, if one desires to offload an area of excessive pressure such as a diabetic ulcer or a non-union of a fracture (that cannot be loaded when a person is walking otherwise it will cause the fracture to move), the orthotic can be segmented at the front portion (as best seen in alternative embodiment depicted in FIG. 31). Thus, the tensioning member may be manipulated to deform the orthotic at a particular location/segment or in a particular angulation. Alternatively, the arch can be raised to supinate the foot. Still alternatively, if there is a lateral attachment point the foot can be pronated by drawing up the lateral side of the orthotic thus being able to dynamically generate a supination or pronation moment or force while the person is walking.

Further, if the attachment point of the tensioning member 28 to the orthotic 18 was substantially at the middle of the arch the tensioning member 28 would drive the orthotic 18 down and flatten it. Alternatively, if the attachment point of the tensioning member 28 to the orthotic 18 was towards the front of the orthotic 18 the tensioning member 28 would draw the orthotic 18 back and raise the arch. Critical to understanding the forgoing is that the ball of the foot is drawn down into a position closer to contact on the platen, i.e. the plane of support, causing the arch of the foot to carry weight bearing pressure and not the ball of the foot during mid-stance (as seen best in FIG. 13).

Referring again to FIG. 3, it depicts further compression of the energy return system. Thus, the arch of the foot is seen as compressed downwardly even further (than in FIG. 2) and thus more energy is being stored in the orthotic 18. If pathology exists in the forefoot, by way of example an ulcer or a stress fracture or a metatarsal non-union, when the orthotic 18 is once again allowed to elevate, it creates an upward moment or force behind the ball of the foot that will lift and unload the ball as the person is moving toward forefoot loading in which the ball of the foot sustains a great deal of pressure. The lift created right behind the ball of the foot will unload or unweight. FIGS. 1-5 depict a basic energy return system. A lever operably coupled at the front of the orthotic and a lever operably coupled to a back portion of the orthotic have been described. As lever deforms the orthotic layer also deforms. How it deforms, i.e. in which direction and at what angulation, depends primarily in part on the point of attachment of lever 14 as will now be discussed in detail.

Figure 6:
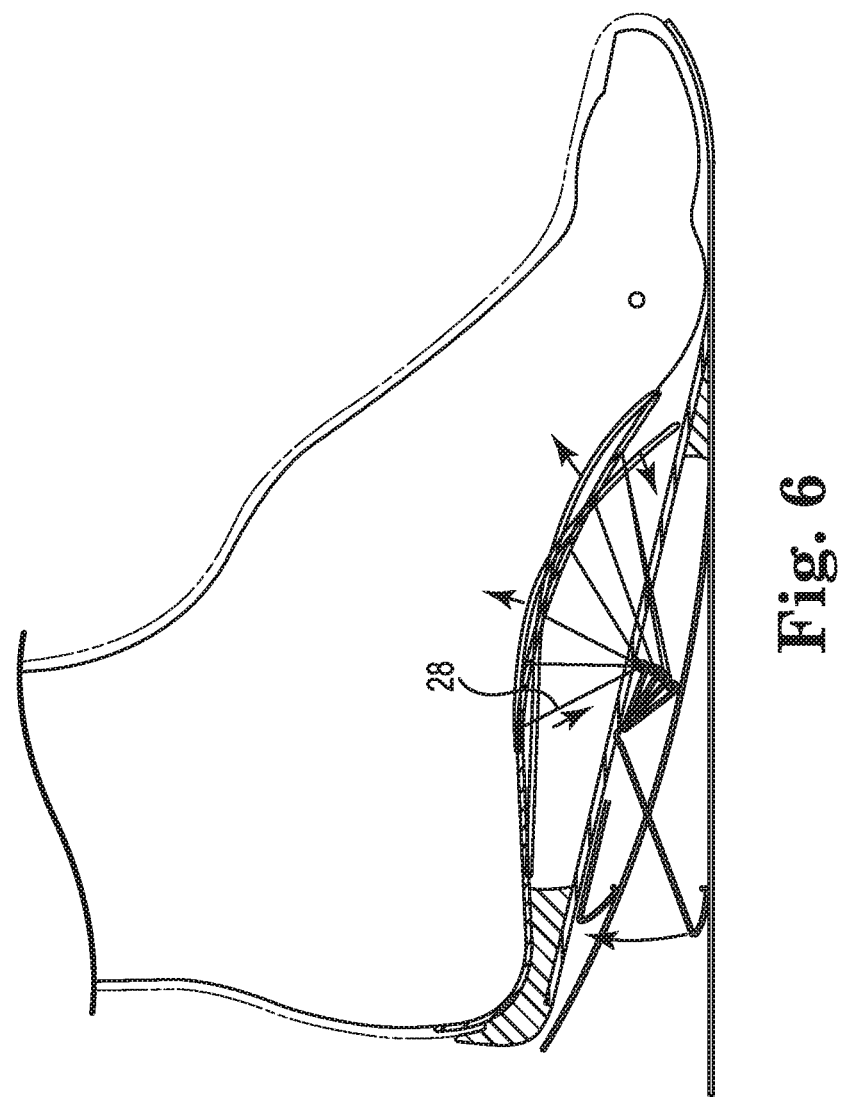
FIG. 6 is a view of the tri-layer orthotic in accordance with the invention showing various attachment points for tensioning member and the effects thereof.
Figure 13:
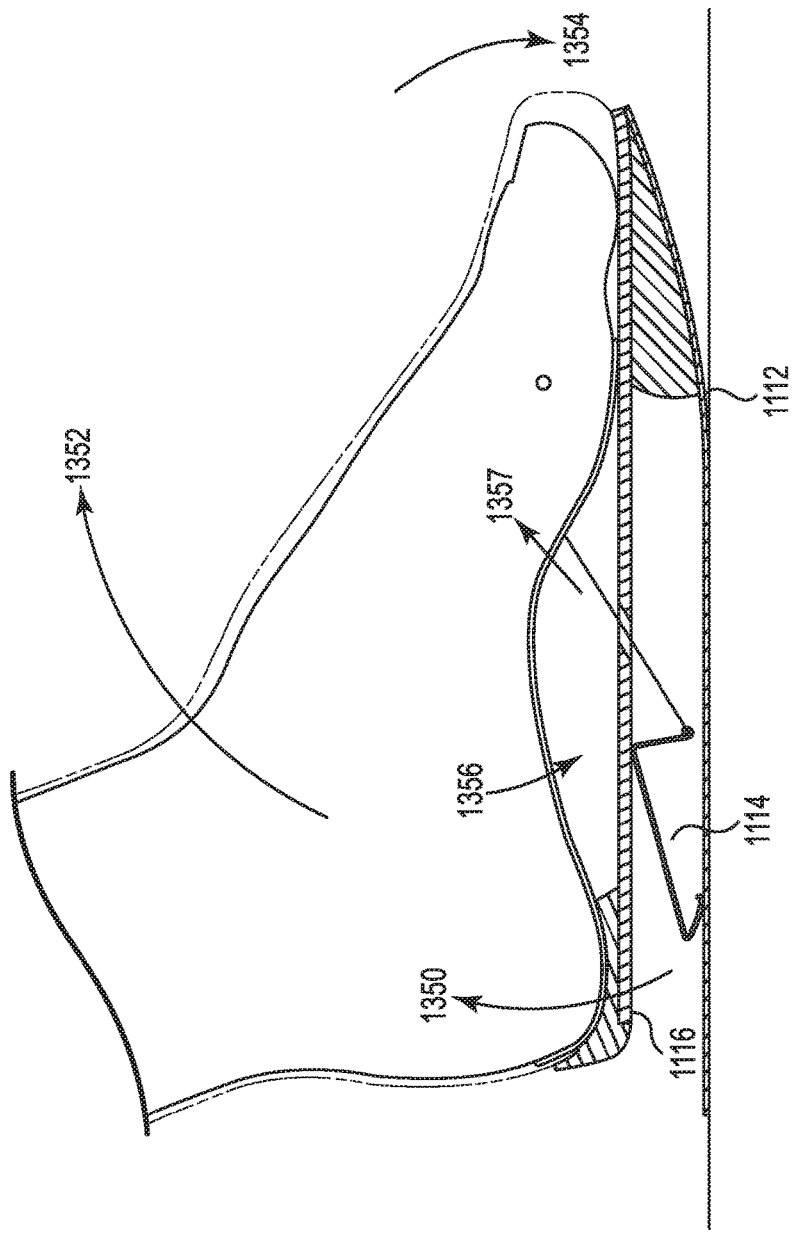
FIG. 13 is a view thereof at mid-stance with arrow showing foot advancing toward terminal stance.

Referring now to FIG. 6 various attachment points on tensioning member 28 and resulting actions are depicted. If the attachment point of the tensioning member 28 to the orthotic 18 is varied, such variation will cause the orthotic 18 to flex in different ways to affect the foot. With a rear attachment of tensioning member 28 to orthotic, the arch of the orthotic 18 is lowered thus reducing ground reactive force between the foot and the orthotic that in the case of posterior tibial dysfunction may make the orthotic intolerable to the patient. This dynamic lowering of ground reactive forces at impact may allow greater biomechanical control to be tolerated by the patient. If the attachment point of the tensioning member 14 to the orthotic 18 is at the front of the orthotic 18, the orthotic arch is raised as best seen in FIG. 13.

In human anatomy, the subtalar joint occurs at the meeting point of the talus and the calcaneus. The subtalar joint allows inversion and eversion of the foot during the gait cycle. Thus, depending on what foot pathology needed treatment, the attachment point of the tensioning member would affection the function of the energy return system. If the attachment point of the tensioning member is placed lateral to the subtalar joint access toward the fifth ray or the lateral aspect of the forefoot, it would have the effect of raising the lateral arch of the orthotic to pronate the foot or tip the foot inward and cause eversion of the subtalar joint. Attachment of the tensioning member medial to the subtalar joint access, by way of example under the first distal ray, would have the effect of raising the medial aspect of the orthotic and would have the effect of causing supination and tip the foot laterally which would invert the subtalar joint. Attachment of the tensioning member to the arch portion of the orthotic would draw the orthotic arch height down to be more flat. This would allow for rebound recoil spring as the lever is unweighted in the back. Drawing the orthotic layer down to the platen and allowing it to rebound back up as the lever is unweighted in the back would create lift proximal to the metatarsal heads or underneath the metatarsal heads if the orthotic is lengthened.

Similarly, the orthotic could be altered in length to affect changes in the foot anatomy. Conventional orthotics terminate behind the ball of the foot to allow for flexion of the ball of the foot. With the tri-layer energy return system of the present invention, the orthotic could be lengthened to be positioned underneath the ball of the foot if unweighting was desired at that area. Moreover, if the orthotic is positioned underneath the metatarsal heads and supported the metatarsal head weight a thrust upward under the ball of the foot could be created increasing vertical energy (as in a jump). Further, the orthotic could also be windowed under an area of an ulcer such that it prevented loading on the ulcer.

Those of skill in the art will appreciate that the flexibility in the base layer 12 and the rocker bottom shape would allow normal gait while controlling dorsiflexion and plantar flexion of the metatarsal phalangeal joint during gait. As noted, flexion of the base layer 12 provides flex energy while also providing shock absorption.

Thus, those of skill in the art will appreciate that the attachment point of the tensioning member to the orthotic and platen can be varied depending of the type of pathology that is being treated and the length and position of the orthotic may also be changed to affect changes in foot anatomy, the foregoing causing the orthotic to act as a leaf spring.

Figure 7:
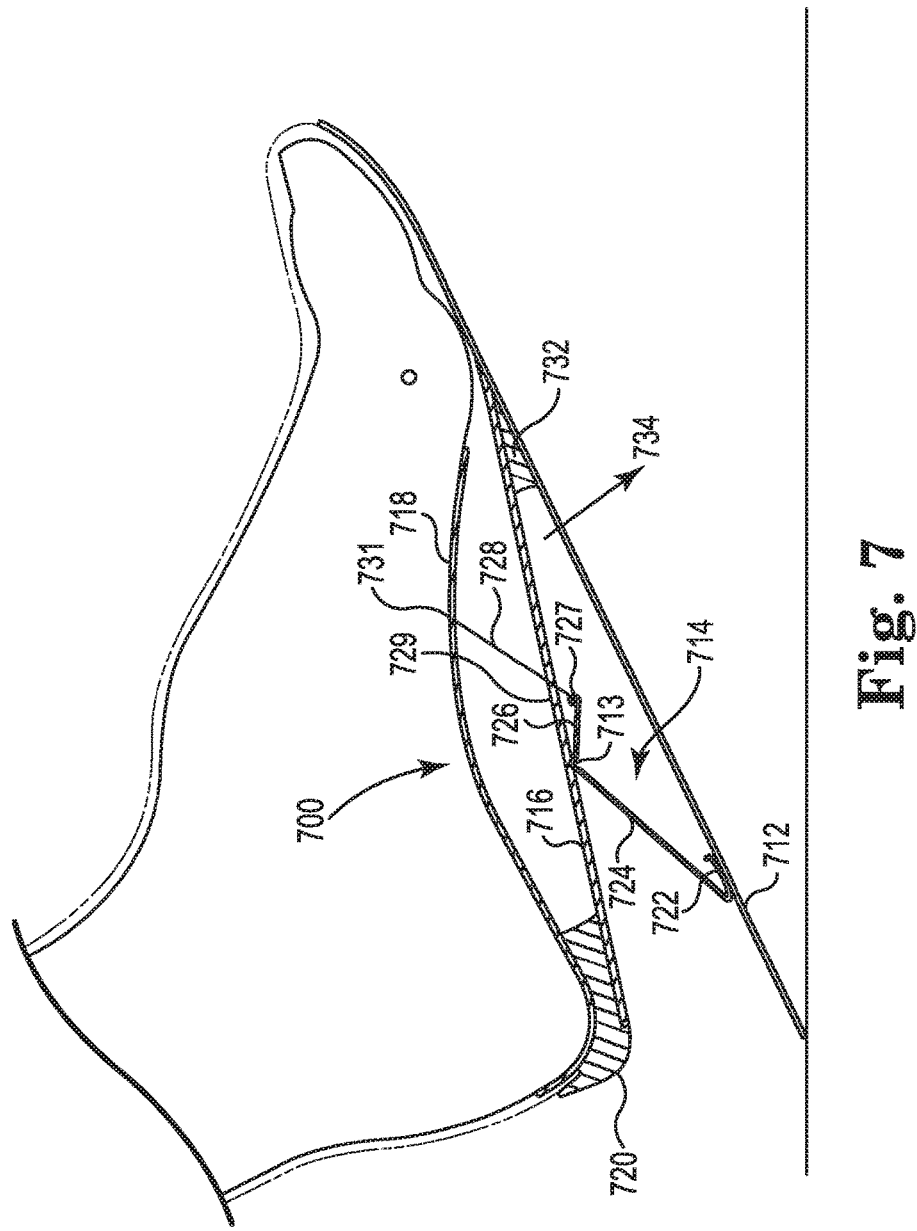
FIG. 7 is a side elevational view of a first alternative embodiment of the invention at the commencement of the gait cycle.

With the foregoing as background, FIGS. 7-10 illustrate a first alternative embodiment of the energy return system 700 in accordance with the invention comprising base layer 712, lever 714, platen 716 and orthotic 718. Functionally, the energy return system 700 of FIGS. 7-10 performs as does the energy return system 10 of FIGS. 1-6. The energy return system 700 illustrated in FIG. 7 is shown at the initial contact with the ground and is incorporated into footwear, brace or the like shown in phantom line. Arrow depicts the normal downward force DF of the foot and the energy return system 700 against a surface at grade. Base 712 may be of any length so long as it generally extends from the sole of the foot to the toe region and may comprise any material used for the soles of shoes including but not limited to rubber, plastics, polymers, polyurethanes and the like. Base 712 is desirably resilient functions as a leaf spring in this alternative embodiment.

Lever 714 includes slide 722, angled central portion 724, fulcrum 725, terminal portion 726 and cable 728. Lever 714 is made from a material that is resilient to allow it to dynamically deform during the gait cycle. Suitable materials that may be utilized for lever 714 include plastics, polymers and resilient metals. Orthotic 718 is also made from a material that is resilient to allow it to dynamically deform during the gait cycle. Suitable materials that may be utilized to construct orthotic 718 include polyolefin; polypropylene; open and closed cell foams and graphites. Platen 716 is desirably made from rigid or semi-rigid materials such as plastics know to those of skill in the art.

Cable 728 operably couples lever 714 at terminal portion 726 to orthotic 718. Platen 716 is desirably rigid or semi rigid and is operably coupled to orthotic 718 through rear gusset 720. Platen 716 is operably coupled to base 712 by front gusset 732. Angled central portion 724 of lever 714 terminates at fulcrum 713. Fulcrum 713 lies adjacent and supports platen 716. Terminal portion 726 includes loop 727 that operably couples cable 728 through pass 729 in platen 716. Cable 728 is coupled to orthotic 718 at attachment point 731 immediately forward of the arch of the foot and thus, indirectly operably couples orthotic 718 and base 712. Cable 728 is depicted as a cable or wire but may also comprise pins, rods, filaments and other structures known to those of skill in the art.

Figure 8:
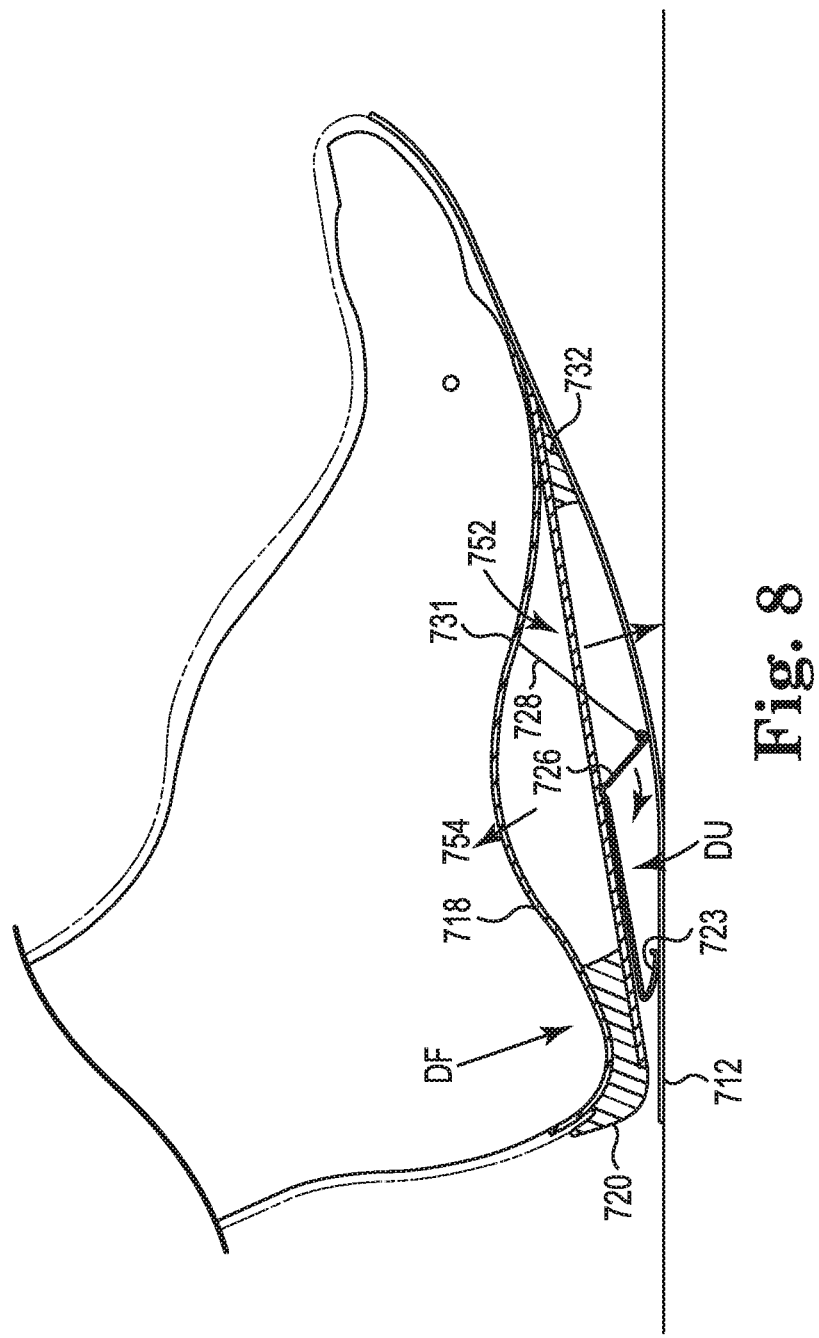
FIG. 8 is a view thereof at heel strike.
Figure 9:
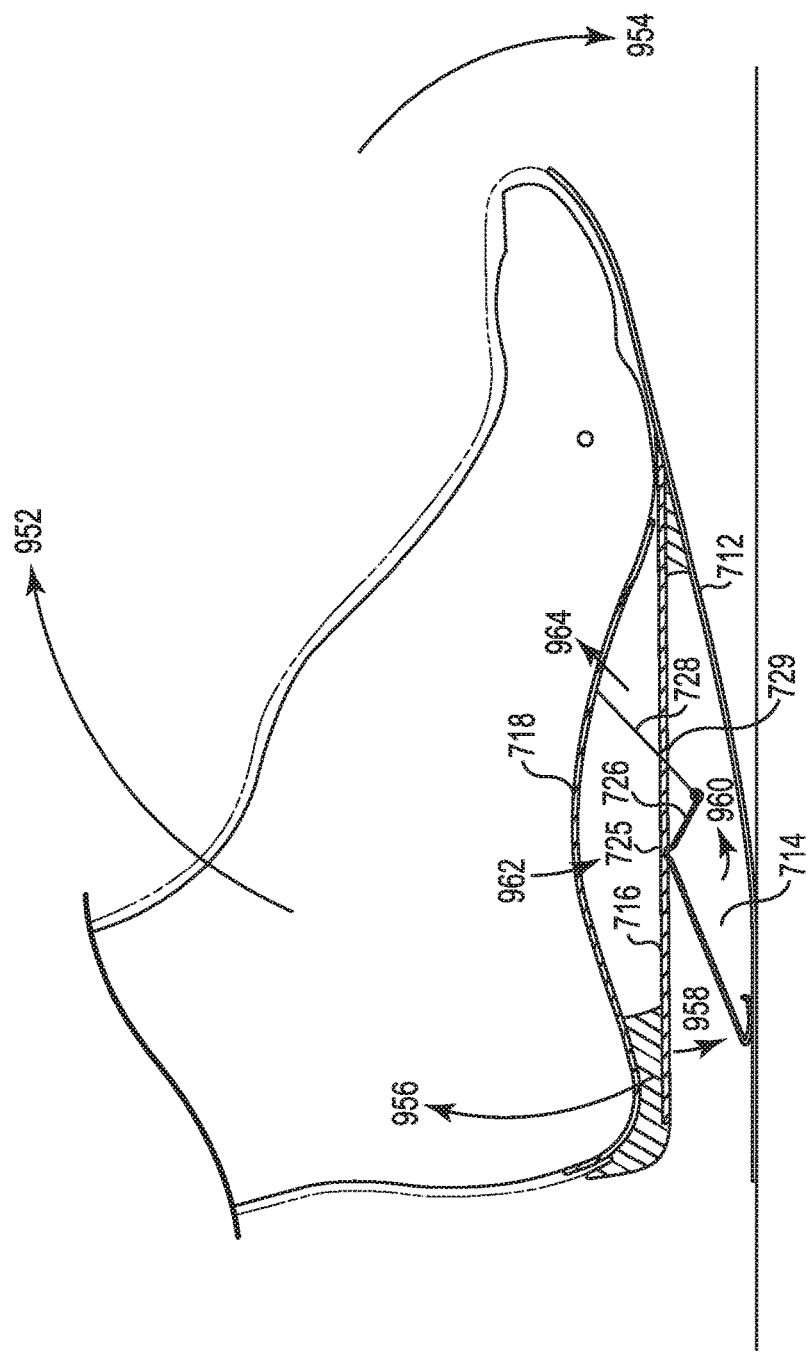
FIG. 9 is a view thereof rebounding from heel strike and moving toward mid-stance.

Referring now to FIG. 8, at heel strike the downward force (DF) of the heel causes base 712 to deform upwardly DU 850 toward platen 716. Slide 722 moves backwards toward heel putting tension on cable 728. Cable 728 thus pulls orthotic 718 away from the ball of the foot 752 causing it to rise against arch 754. Referring now to FIG. 9, the foot is shown as commencing forward rotational motion of the foot 952 toward mid-stance. Downward forces on the heel are released and unloaded 956. This rebound causes lever 714 to move toward its original position 958, 960 releasing energy from orthotic 718 and causing orthotic to flatten against the arch 962 and to thrust forward and upward 964.

Figure 10:
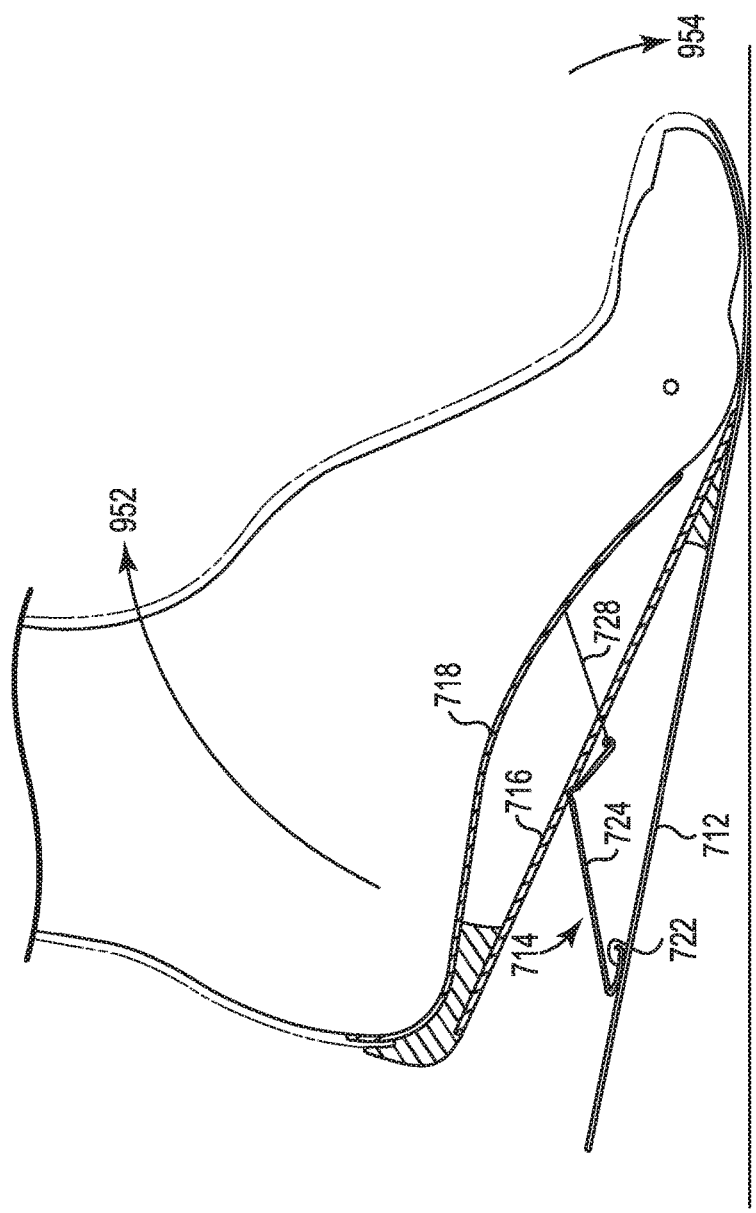
FIG. 10 is a view thereof at terminal stance with foot moving toward toe-off or the pre-swing phase.

FIG. 10 illustrates the foot continuing its normal forward rotational motion toward toe-off 954 with energy unloaded from the energy return system.

FIGS. 11-14 illustrate a second alternative embodiment of the energy return system in accordance with the invention similar to FIGS. 7-10 except cable 1128 is shown operably coupled to orthotic 1118 immediately proximal to the ball of the foot. FIGS. 11-14 again illustrate a part of the gait cycle from the unweighted position, to the loading response at heel strike through toe-off.

Figure 11:
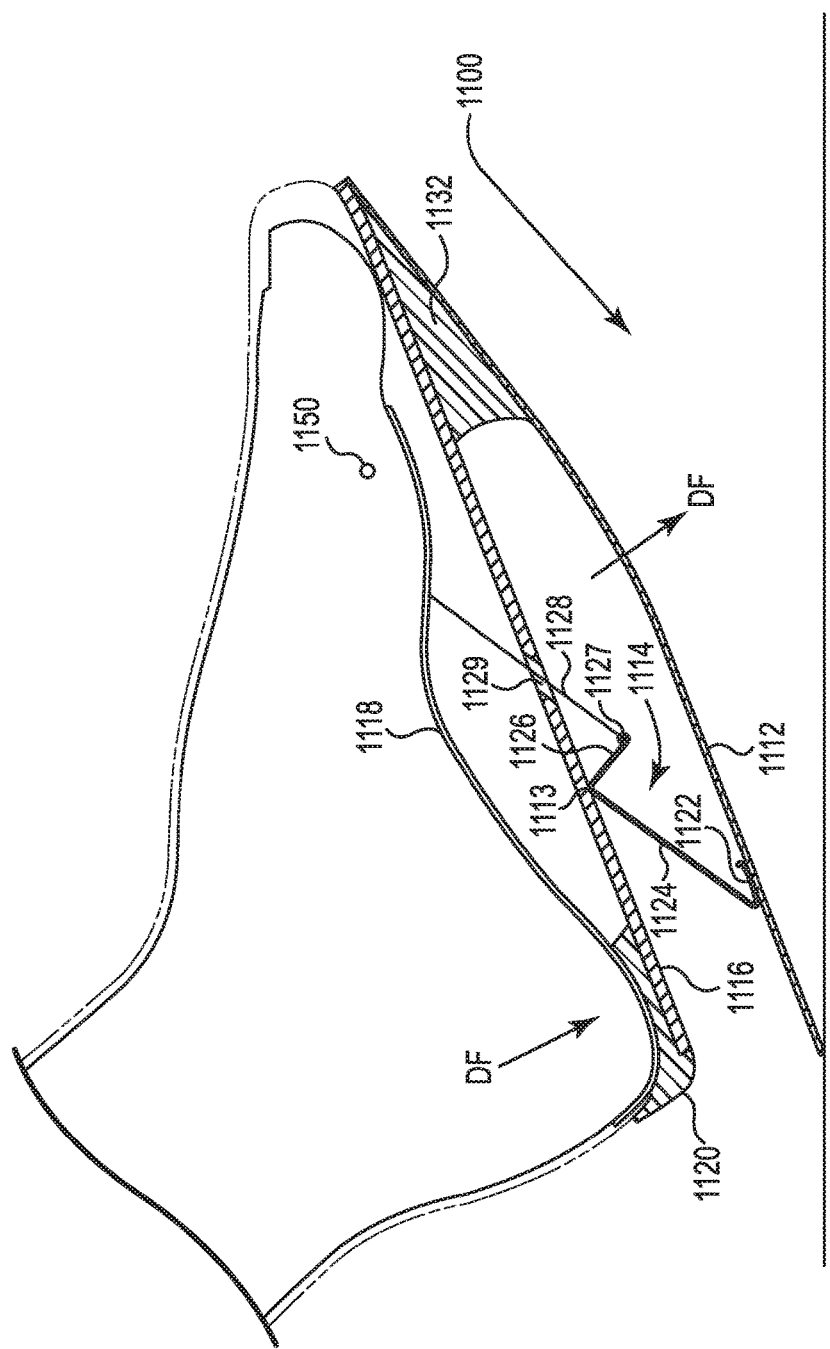
FIG. 11 is a side elevational view of a second alternate embodiment of the invention beginning initial contact with the ground.

Referring now to FIG. 11, like elements are identified with like numerals. The energy return system 1100 in accordance with the invention comprises base 1112, lever 1114, platen 1116 and orthotic 1118. The energy return system 1100 illustrated in FIG. 11 is shown prior to heel strike and is incorporated into shoe shown in phantom line. Arrow depicts the normal downward force DF of the foot and the energy return system 1100 against a surface at grade. Base 1112 may be of any length so long as it generally extends from the sole of the foot to the toe region and may comprise any material used for the soles of shoes including but not limited to rubber, plastics, polymers, polyurethanes and the like. Base 1112 is desirably resilient functions as a leaf spring in this alternative embodiment.

Lever 1114 includes slide 1122, angled central portion 1124, fulcrum 1125, terminal portion 1126 and cable 1128. Lever 1114 is made from a material that is resilient to allow it to dynamically deform during the gait cycle. Suitable materials that may be utilized for lever 1114 include plastics, polymers and resilient metals. Orthotic 1118 may also made from a material that is resilient to allow it to dynamically deform during the gait cycle. Suitable materials that may be utilized to construct orthotic 1118 include polyolefin; polypropylene; open and closed cell foams and graphites. Platen 1116 is desirably made from rigid or semi-rigid materials such as plastics known to those of skill in the art.

Cable 1128 operably couples lever 1114 at terminal portion 1126 to orthotic 1118. Platen 1116 is desirably rigid or semi rigid and is operably coupled to orthotic 1118 through rear gusset 1120. Platen 1116 is operably coupled to base 1112 by front gusset 1132. Angled central portion 1124 of lever 1114 terminates at fulcrum 1113. Fulcrum 1113 lies adjacent and supports platen 1116. Terminal portion 1126 includes loop 1127 that operably couples cable 1128 through pass 1129 in platen 1116. Cable 1128 is coupled to orthotic 1118 at attachment point 1150 immediately proximal the rotation axis of the ball of the foot and thus, operably couples orthotic 1118 and platen 1116. Cable 1128 is depicted as a cable or wire but may also comprise pins, rods, filaments and other structures known to those of skill in the art.

Figure 12:
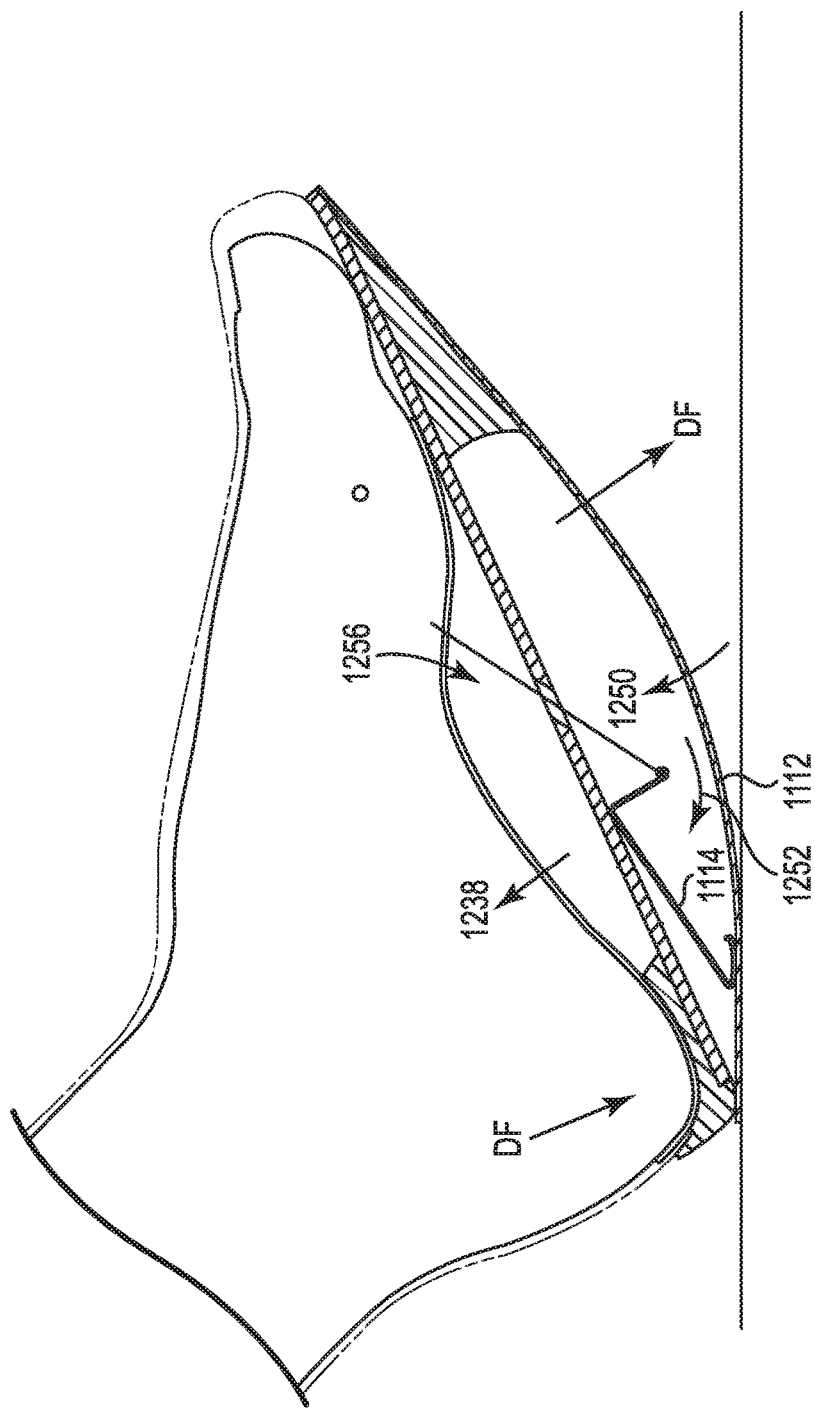
FIG. 12 is a view thereof at full initial contact with the ground.

Referring now to FIG. 12, downward forces at heel strike cause base 112 to deform upwardly toward the heel 1250 causing lever 1114 to slide proximally 1252. As lever continues sliding proximally tension is put on cable 1128 drawing orthotic 1118 rearward 1256 away from the ball of the foot and upward against the arch of the foot 1258.

FIG. 13 depicts the unloading 1350 of the base 1116 and the forward unloading motion 1352, 1354 of the foot as it moves from mid-stance toward toe-off position. The unloading motion transmits rebound energy to the system allowing lever 1114 to commence returning to original position. The rebound energy propels heel upward and forward while flattening 1356 orthotic 111 against arch and to thrust forward 1357.

Figure 14:
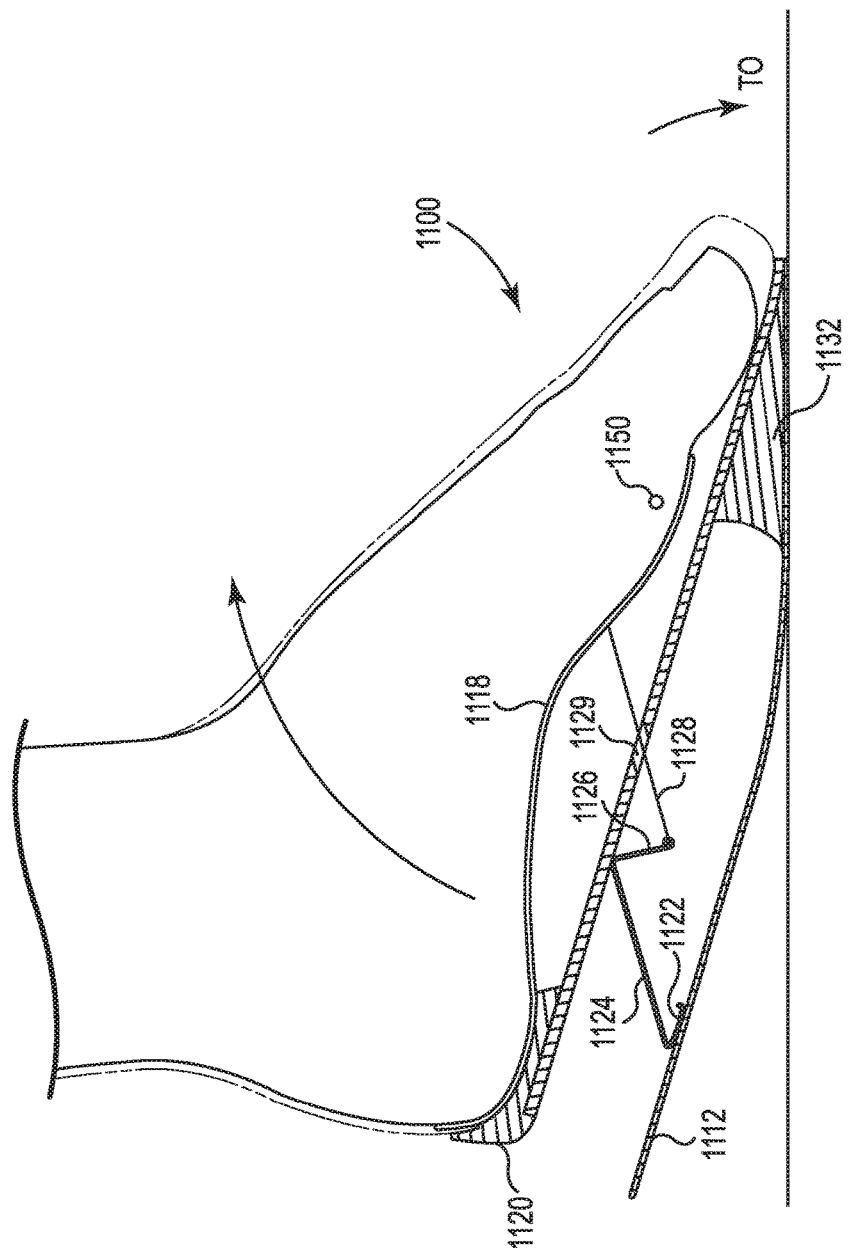
FIG. 14 is a view thereof near pre-swing.

FIG. 14 illustrates the forward thrusting of the foot toward toe-off and the continuing rebound due to the release of energy from the energy return system in accordance with the invention. Thus, the embodiment depicted in FIGS. 11-14 is designed to address forefoot pressures and operates with limited MPJ dorsiflexion. Thus, stress fractures, metatasalgia and foot ulcers and other types of dysfunctions may be treated.

Figure 15:
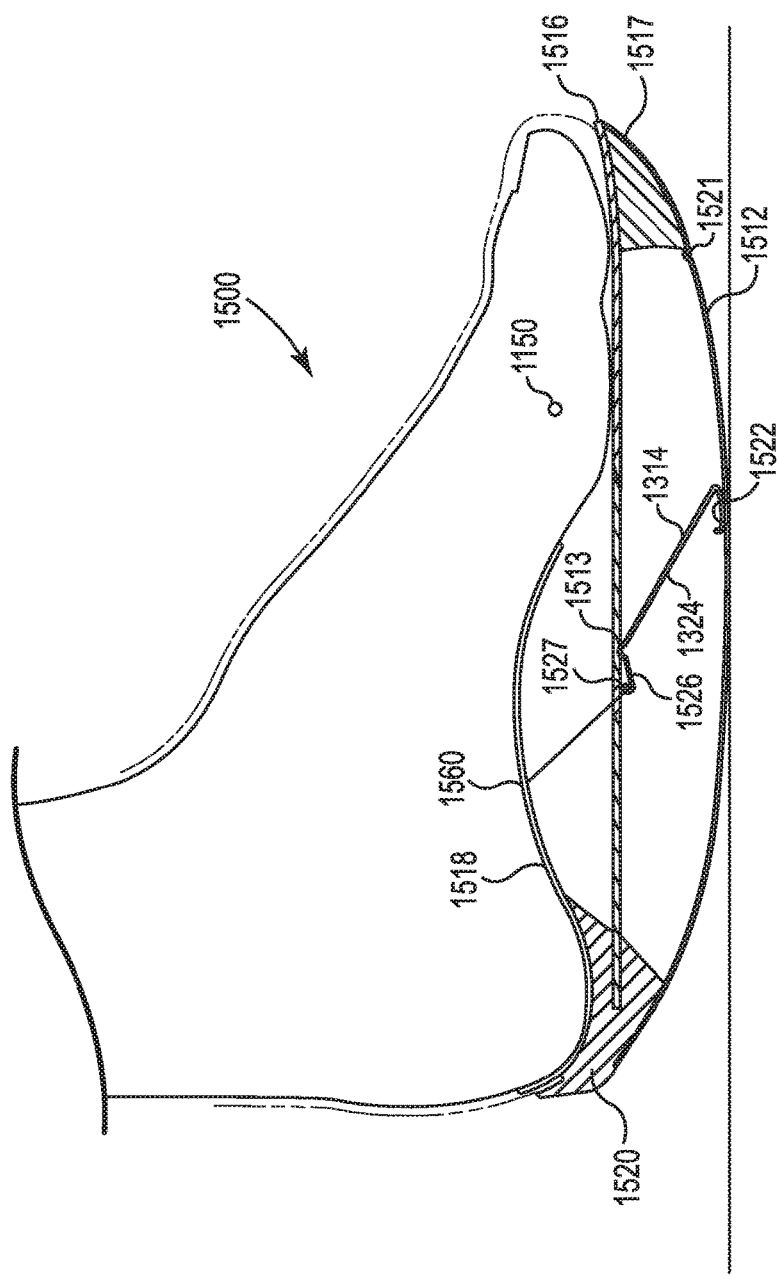
FIG. 15 is a side elevational view of a third alternate embodiment of the invention shown on an equines patient in the unburdened position.
Figure 16:
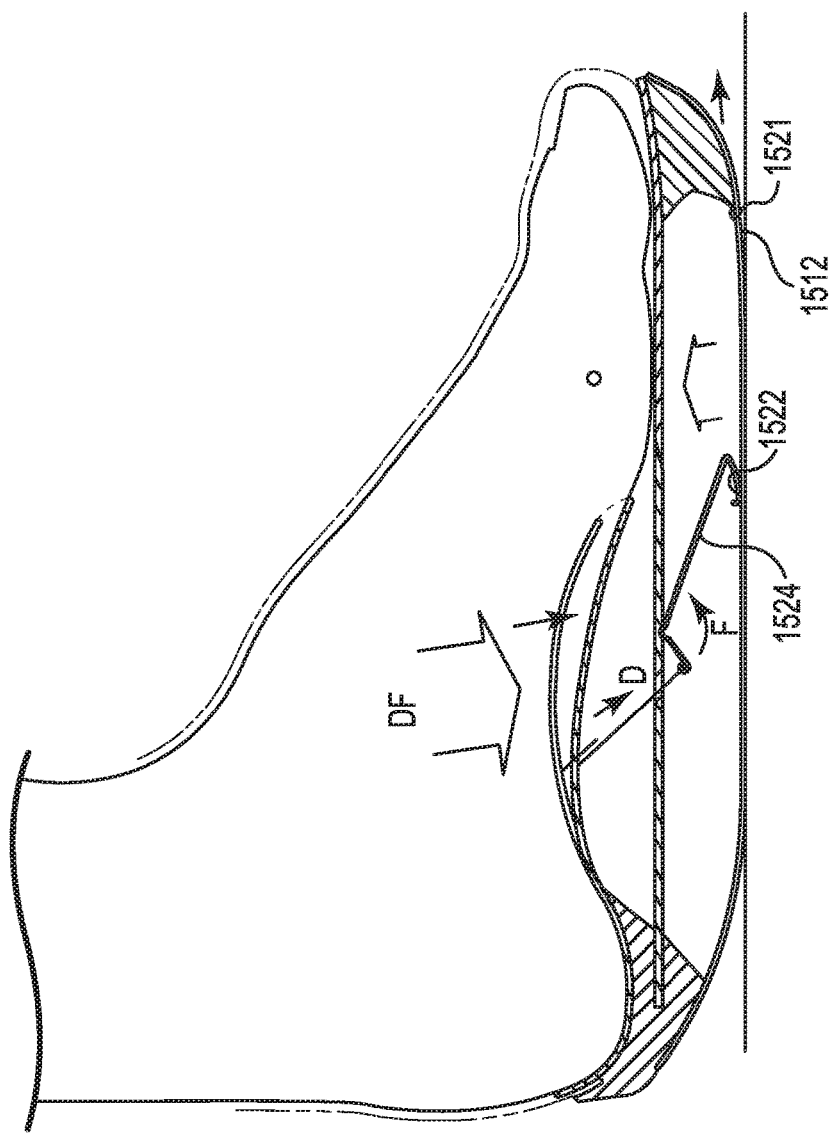
FIG. 16 is a view thereof in a position toward loading.
Figure 17:
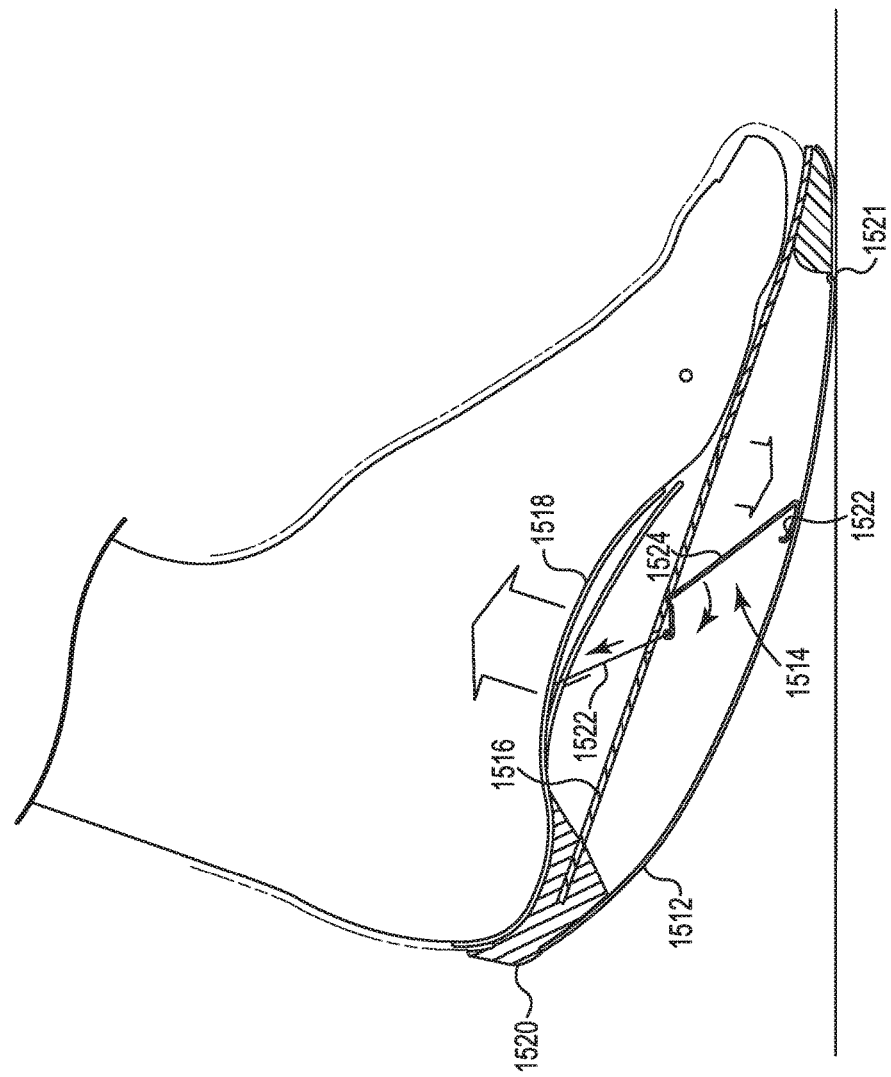
FIG. 17 is a view thereof at toe impact.
Figure 18:
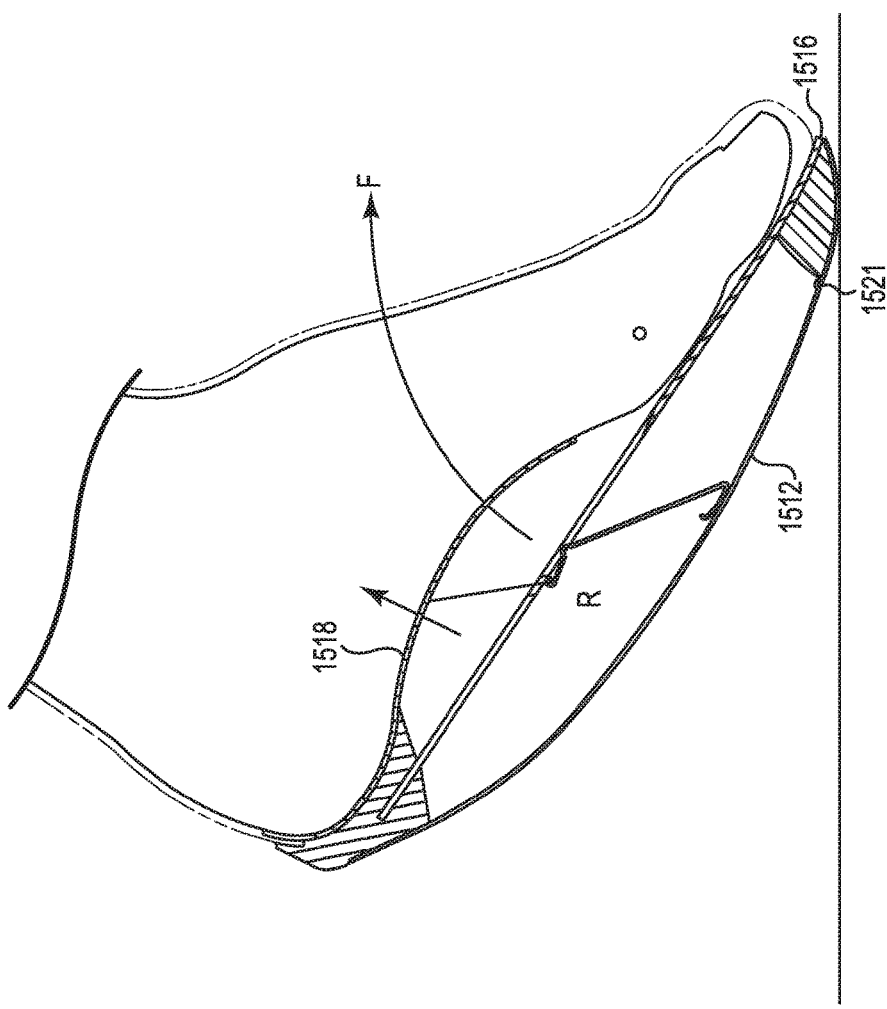
FIG. 18 is a view thereof at completion of toe impact.

Referring now to FIGS. 15-18 a third alternative embodiment in accordance with the energy return system 1500 of the present invention is illustrated. Particularly, lever 1514 is inverted and designed to operate differently than previously described embodiments. As can be seen the attachment point 1560 of cable 1528 is at a point proximal to the mid-arch. In addition rear gusset operably couples base 1512 with platen 1516 and orthotic 1518. Platen 1516 is also operably coupled to base 1512 at the forefoot by compressible tip 1517. As can be seen in FIGS. 15-16 compressible tip includes a hook 1521 that allows base 1512 to uncouple due to compressive ground forces as the foot moves toward toe-off and recouple when no compressive forces are present. FIG. 15 depicts the energy return system in the unburdened profile or in other words at rest. Referring to FIG. 16, downward force DF creates systematic collection of potential energy by compressing resilient leaf spring-like base 1512. Angled central portion 1524 of lever 1514 rotates forward as cable 1528 pulls orthotic 1518 downward D away from arch. The flattening of orthotic 1528 presses the distal edge of orthotic forward and compressible tip 1517 bulges forward. As best seen in FIG. 17 as the foot nears toe-off, energy is further absorbed as base 1512 continues to flatten and rotates lever 1514 to continue drawing orthotic 1518 to flatten while the distal edge of orthotic moves forward and the ball of foot begins to lift. As best seen in FIG. 18, as the foot is raised and rotated forward F toward toe-off the base 1512 and flattened orthotic 1518 release stored energy causing angled central portion 1524 of lever 1514 to move rearward which releases the tension on cable 1528 and orthotic 1518. Orthotic 1518 returns or rebounds to support the arch of foot.

The embodiment depicted in FIGS. 15-18 is designed for the treatment of equines (toe runners with no heel strike) in which limited dorsiflexion at the ankle causes pathology. Equines is the primary cause of ulcers in diabetic equines patients.

Figure 19:
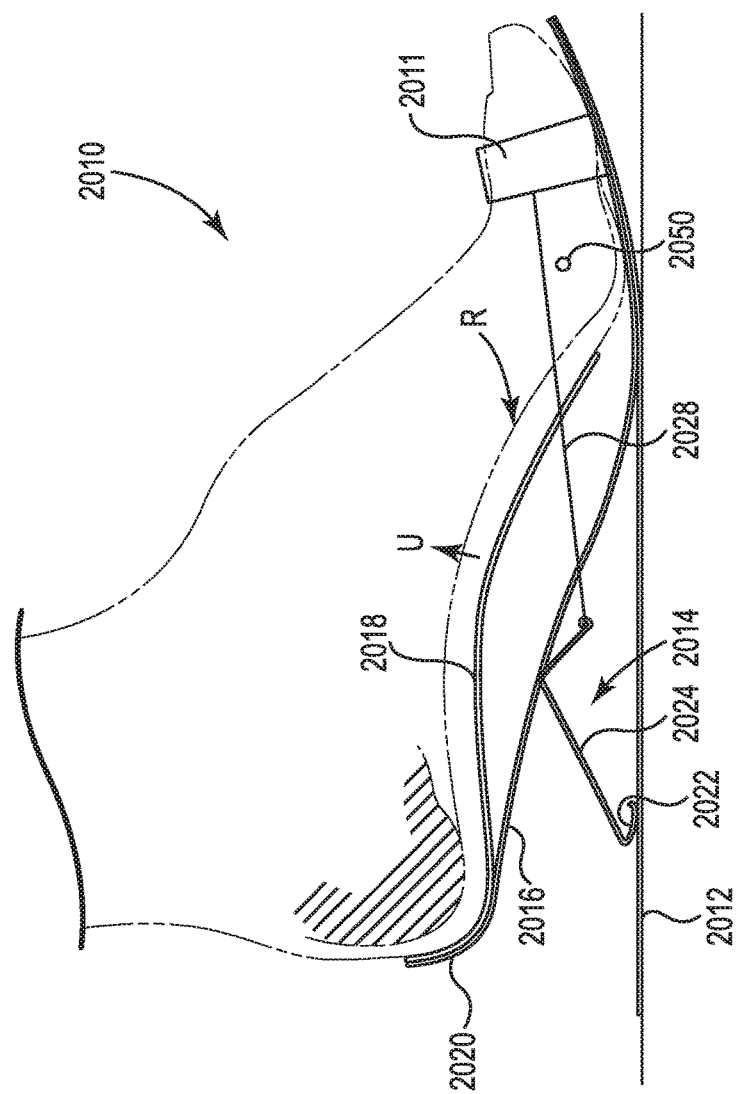
FIG. 19 is a side elevational view of a fourth alternate embodiment of the invention with the foot depicted in a static unburdened position.

FIG. 19 depicts a fourth alternative embodiment 2010 of the energy return system with the foot depicted in a static unburdened position. Like elements are labeled with like numerals. Particularly, orthotic 2018 is attached to platen 2016 at the rear of the foot 2020. Base 2012 is attached to platen 2016 underneath the ball of the foot 2029. Band 2011 surrounds the phalanges and the cable 2028 is attached to the band. As platen 2016 flattens, lever 2014 functions to drawn arch up U. Orthotic 2018 moves rearward R and upward U against the arch when downward force is applied to the ground during the gait cycle. This embodiment is designed to treat plantar fascia.

Figure 21:
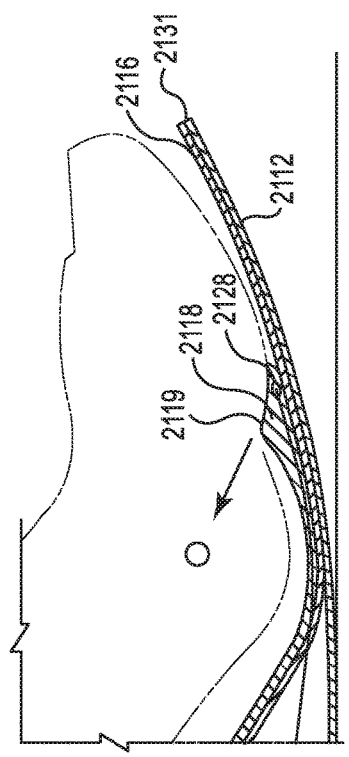
FIG. 21 is an enlarged detail taken from the area 21A of FIG. 20.
Figure 20:
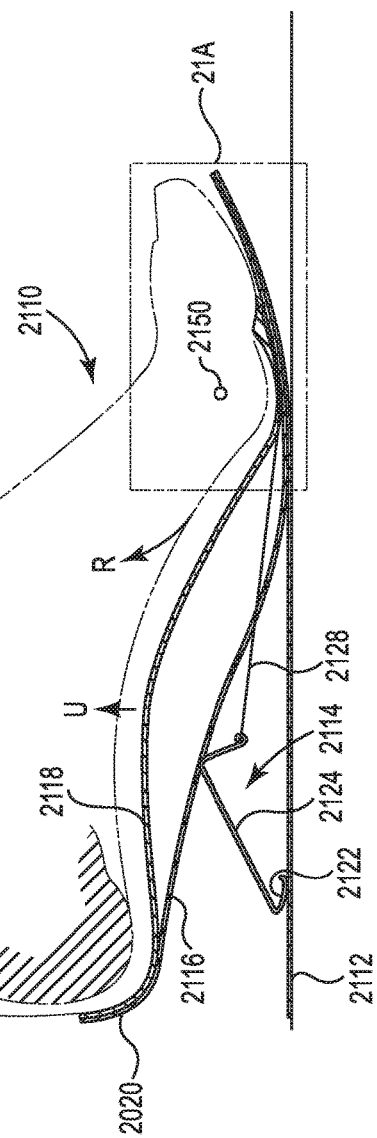
FIG. 20 is a side elevational view of a fifth alternate embodiment of the invention shown in a static unburdened position.
Figure 33:
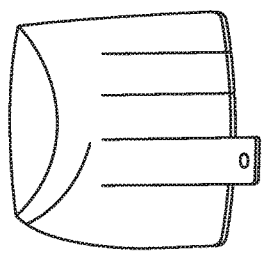
FIG. 33 is a front elevational view thereof showing the secondary position.

FIGS. 20 and 21 depict a fifth alternative embodiment 2110 of the energy return system in accordance with the invention designed to treat plantar fasciitis. Like elements are labeled with like numerals. Base 2112 is attached to platen 2116 behind heel at 2120. As best seen in FIG. 21, orthotic 2118 is modified to form a cup that cradles sulcus 2119 thus allowing the foot to roll forward during gait without restriction. Cable 2128 is coupled to orthotic 2118 slightly forward of sulcus 2019. Base 2112 and platen 2116 are coupled underneath the ball of the foot 2129 through to tip 2131. Lever 2114 will thus draw the orthotic 2118 rearward R and upward U against the arch, and draws the sulcus rearward when downward force is applied to the ground during the gait cycle.

FIG. 22 depicts a sixth alternative embodiment of the invention. The orthotic is fixedly attached at the distal end to platen 2260 and free at the proximal end. As can be seen, orthotic is cupped around heel. The base layer 2212 is fixedly attached 2215 at the proximal end to platen 2216. Cable 2228 is attached to orthotic 2218 underneath the sole of the foot. In this embodiment as the user propels through the gait cycle, the orthotic 2218 will be drawn forward 2223 while lifting 2225 beneath the arch giving support to the plantar fascia.

FIG. 23 depicts a seventh alternative embodiment of the energy return system in accordance with the invention. Like features have like numerals. As can be seen, orthotic 2318 is fixedly attached 2360 at the distal end to platen 2316. Orthotic 2318 is cupped around the heel of the foot. The proximal end of orthotic 2318 is free. Base 2312 is fixedly attached to platen 2316 by spacer or bridge 2315, which mitigates ground reactive forces. Cable 2328 is attached to orthotic slightly forward of the heel. In operation, as the foot moves through the gait cycle, the orthotic 2318 is drawn forward 2223 while lifting the arch upward 2225 giving support to the plantar fascia.

As discussed previously, in human anatomy, the subtalar joint occurs at the meeting point of the talus and the calcaneus. The subtalar joint allows inversion and eversion of the foot during the gait cycle. Thus, depending on the particular foot pathology needing treatment, the attachment point of the tensioning member would affect the function of the energy return system.

Tensioning member is attached to the orthotic underneath the arch portion. Thus the tensioning member would draw the orthotic arch height down to be more flat. This would allow for rebound recoil spring as the lever is unweighted in the back. Drawing the orthotic layer down to the platen and allowing it to rebound back up as the lever is unweighted in the back would create lift proximal to the metatarsal heads or underneath the metatarsal heads.

Referring now to FIGS. 24-26 orthotic 2400 is shown, which is the base orthotic for the modifications seen in FIGS. 27-32. Orthotic 2400 includes a tab 2410 coupled to a bottom side of the base layer of orthotic 2400. Tab 2410 is operably coupled by pin 2418 to an elongate lever 2414 that is configured to rotate about pin 2418. Those of skill in the art will appreciate that having a rotatable lever is advantageous because the orthotic can be adjusted from time to time as needed. Tensioning member 2428 may comprise a filament, cable, wire or the like having a first end 2402 and a second end 2403. The first end 2402 is coupled at attachment point 2412, which is shown in a neutral position. Attachment point may be an aperture in the orthotic to which the tensioning member 2428 is coupled. Alternatively, attachment point 2412 may comprise mechanical or chemical attachment means. The coupling of the tensioning member 2428 to attachment point 2412 fixes the lever 2414 so that it cannot rotate. The second end of the lever is coupled to tab 2410 by pin 2418. Attachment point 2403 of tensioning member 2428 is positioned underneath an arch portion 2411 of the orthotic 2418. As can best be seen in FIG. 25, the tensioning member is bending the front portion of the orthotic 2400 downwardly 2415 raising the arch height and thus creating lift proximal to the metatarsal heads or underneath the metatarsal heads depending on the length of the orthotic top layer. FIG. 26 illustrates that there is no angle of correction in the orthotic because the tensioning member is in the "neutral," centered position so that it neither pronates nor supinates the orthotic.

Referring now to FIGS. 27-28 orthotic 2400 is depicted with a cut 2401 approximately down the center of orthotic 2400. Orthotic 2400 includes a tab 2410 coupled to a bottom side of a base layer thereof. Tab 2410 is operably coupled by pin 2418 to a elongate lever 2414 that rotates about pin 2418. Those of skill in the art will appreciate that rotatable lever is advantageous because the orthotic can be adjusted from time to time as needed. Tensioning member 2428 may comprise a filament, cable, wire or the like having a first end 2402 and a second end 2403. The first end 2402 is coupled at attachment point 2412, which as shown, is medial to the center line, distally under the location of the first ray and may comprise an aperture in the orthotic. Alternatively, attachment point 2412 may comprise mechanical or chemical attachment means. Attachment point 2412 fixes the lever 2414 so that it cannot rotate. The second end of the lever is coupled to tab 2410 by pin 2418. In operation, the tensioning member 2128 causes orthotic 2400 to rotate downward 2414 on the medial side of the orthotic by therapeutic angle 2416 increasing forefoot varus dynamically having the effect of raising the medial aspect of the orthotic arch and would have the effect of causing supination and tip the foot laterally which would invert the subtalar joint. FIG. 28 illustrates angle of correction 2416.

If the attachment point 2412 of the tensioning member 2428 is placed lateral to the subtalar joint access toward the fifth ray or the lateral aspect of the foot, it would have the effect of raising the lateral aspect of the orthotic arch to pronate the foot or tip the foot inward and cause eversion of the subtalar joint.

FIGS. 29-30 illustrate orthotic 2400 with segment or cut 2901 approximately down the center line of the orthotic 2400. Orthotic 2400 includes a tab 2410 coupled to a bottom side thereof. Tab 2410 is operably coupled by pin 2418 to a elongate lever 2414 that rotates about pin 2418. Those of skill in the art will appreciate that having a rotatable lever is advantageous because the orthotic and its angle of correction can be adjusted from time to time as needed. Tensioning member 2428 may comprise a filament, cable, wire or the like having a first end 2402 and a second end 2403. The first end 2402 is coupled at attachment point 2412, which as shown, is lateral to the subtalar joint access, distally under the location of the fifth ray. Attachment point 2412 fixes the lever 2414 so that it cannot rotate. The second end of the lever is coupled to tab 2410 by pin 2418. Tensioning member 2428 is attached to orthotic 2400 laterally at attachment point 2412. In this position, tensioning member 2428 causes orthotic 2400 to rotate downward on the lateral side by therapeutic angle 2916 increasing forefoot valgus dynamically having the effect of causing pronation and tipping the foot medially. FIG. 30 illustrates the angle of correction 2416.

Figure 32:
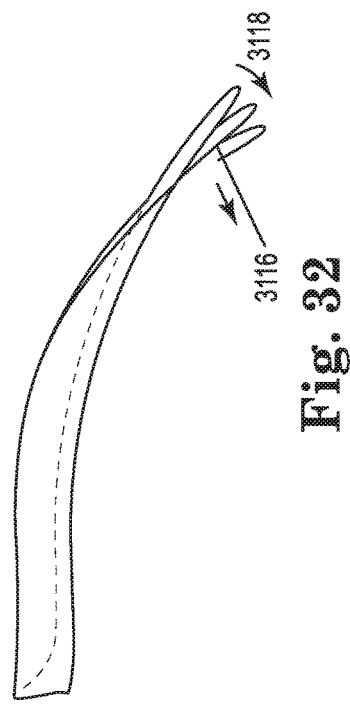
FIG. 32 is a side elevational view thereof similar to that of FIG. 25 showing a secondary position.

Referring now to FIGS. 31-32 orthotic 2400 is shown with a segmented digit array 3114. Orthotic 2400 includes a tab 2410 coupled to a bottom side of the orthotic 2400. Tab 2410 is operably coupled by pin 2418 to an elongate lever 2414 that is configured to rotate about pin 2418. Those of skill in the art will appreciate that having a rotatable lever is advantageous because the orthotic can be adjusted from time to time as needed. Tensioning member 2428 may comprise a filament, cable, wire or the like having a first end 2402 and a second end 2403. The first end 2402 is coupled at attachment point 2412, which as shown, is on the second ray position. The coupling of the tensioning member 2428 to attachment point 2412 fixes the lever 2414 so that it, cannot rotate. The second end of the lever is coupled to tab 2410 by pin 2418. Attachment point 2403 of tensioning member 2428 is underneath the arch portion 2411 of the orthotic 2418. In operation the second digit ray 3112 of orthotic 2400 is pulled downward 3116 by therapeutic angle 3118 to achieve the remedial therapeutic goal of dynamic offloading of the metatarsals. For example, if the attachment point is on the first segmented ray dynamic offloading of the first metatarsal-phalangeal joint occurs to treat Hallux Limitus. If the attachment point is on the second ray stress fractures, matasalgia and the like are treated. Those of skill in the art will appreciate that the attachment point 2412 of the tensioning member 2428 may be attached to any ray of the segmented orthotic to result in dynamic off-loading of a particular metatarsal.

Those of skill in the art will appreciate that the segmented orthotic described in FIGS. 27-32 is not limited as to how the orthotic is segmented or which ray the tensioning member is attached to. Rather, depending on the particular foot pathology that needs correction any segment of the orthotic can be made and the tensioning member may be attached to any ray. For example, it is anticipated that two parallel cuts could be made in the orthotic while the tensioning member is attached to the second ray making the second ray dynamic.

FIGS. 34-44 illustrate a bi-layer orthotic designed to correct a pronated foot and/or a supinated foot. When standing, pronation occurs as the foot rolls inwards toward its medial side and the arch of the foot flattens. Supination is the opposite of pronation and refers to the outward roll of the foot to its lateral side during normal motion.

Figure 35:
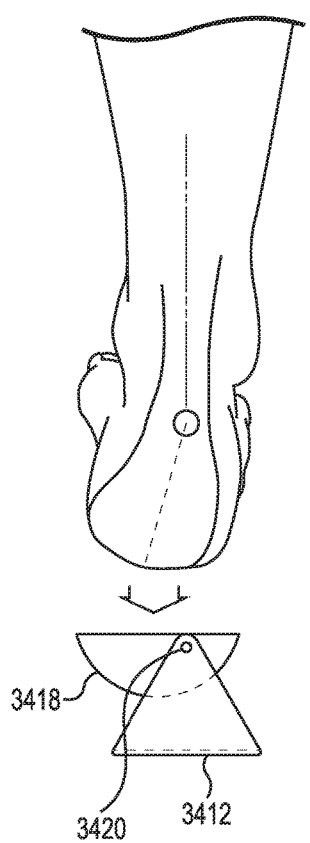
FIG. 35 is a rear elevational view of the bi-layer orthotic of FIG. 34 taken along line 35-35 and showing a pronated foot requiring correction descending into the bi-layer orthotic.
Figure 36:
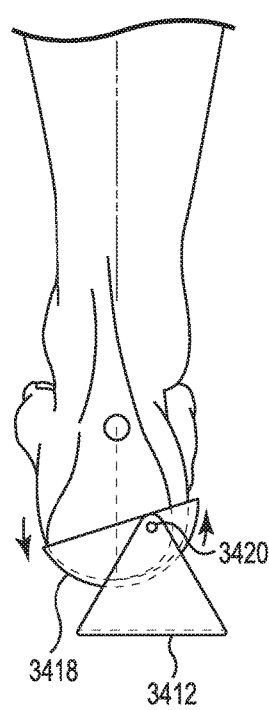
FIG. 36 is a rear elevational view thereof showing the therapeutic correction of a pronated foot.
Figure 37:
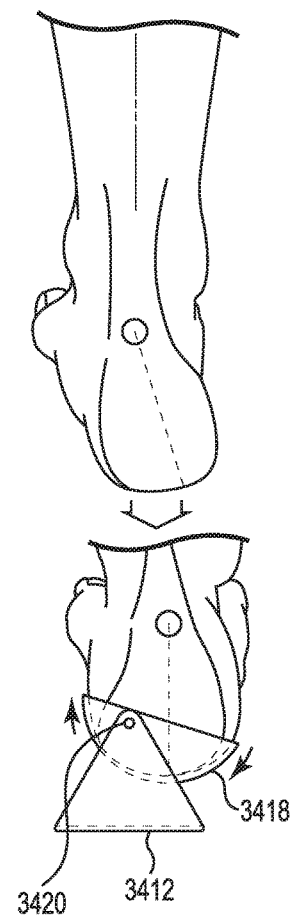
FIG. 37 depicts a supinated foot descending into the bi-layer orthotic in accordance with the invention of FIG. 34 and showing the correction.

FIGS. 34-41 depict a bi-layer orthotic in accordance with the invention that may include a cushioning layer between orthotic 3400 and base layer 3412, omitted for clarity. FIG. 34 is a side elevational view of a bi-layer orthotic 3400 in accordance with an embodiment of the invention. As can be seen orthotic 3400 includes an upper layer 3411 and base layer 3412. Base layer 3412 is operably coupled to orthotic 3400 at the heel cup 3418 of the orthotic 3400 by pin 3420, whose function is best seen in FIGS. 35-37. Pin 3420 is pivotally received by heel cup 3418 and coupled to base 3412 such that orthotic 3418 pivots relative to the base 3412.

FIG. 35 is a rear elevational view taken along line 35-35 of FIG. 34 showing a supinated foot requiring correction. FIG. 36 is a rear elevational view of the supinated foot received within the heel cup 3418 of orthotic 3400. To provide the proper correction, pin 3420 is off-set from the longitudinal axis of the orthotic 3400 toward the lateral side of base layer 3412. As seen in FIG. 36 as the foot applies weight to the heel cup 3418 the orthotic heel cup pivots downwardly on the medial side and upwardly on the lateral side to cause the foot to roll inwardly to a neutral position. Thus orthotic 3400 has provided the therapeutic correction.

Similarly, FIG. 37 is a dynamic rear elevational view similar to that of FIG. 36 showing a pronated foot requiring correction. Pin 2020 is off-set from the longitudinal axis of orthotic 3400 toward the medial side of the heel cup 3418 to provide correction as the pronated foot is received by heel cup 3418. As the individual places the foot into heel cup 3418, heel cup 3418 pivots upwardly on the medial side and downwardly on the lateral side and causes the foot to roll outwardly to a neutral position. The differential travel of the foot in orthotic 3400 causes the therapeutic correction. Those of skill in the art will appreciate that the portion of the base layer 3412 that is pivotally coupled to the heel cup relies of the flexibility of the material to make the desired correction as best seen in FIG. 34 by arrow 3419. The correction may be adjusted by shifting the axis of the pin 3420 further from the midline of the heel cup 3418 without the need for sliding or channels.

FIG. 38A is a side elevational view of an alternative structure for the pin 3420 of bi-layer orthotic 3400. Orthotic 3800, as with orthotic 3400, may include a cushioning layer between the upper layer 3811 and base layer 3812, which has been omitted for clarity. Bi-layer orthotic 3800 includes base layer 3812 and upper layer 3811. Upper layer 3811 is coupled to base layer 3812 at the heel cup 3818 of upper layer 3811 by arcuate rotator follower 3820 as best seen in the enlarged view depicted in FIG. 38B. Arcuate rotator follower 3820 includes an outer coupling piece 3832 and an inner follower piece 3834. FIGS. 39-41 are views taken along line 39 of FIG. 38. Base layer 3812 includes an arcuate shaped channel 3822 cut therein that receives inner follower piece 3824. Outer coupling piece 3822 secures the inner follower piece 3824 in the channel 3822 and to base layer 3812. Channel 3832 is cut so that it curves toward the medial side of orthotic 3800.

FIG. 39 is a rear elevational view taken along line 39-39 of FIG. 38 with the addition of the lower portion of a leg and a pronated foot requiring correction. FIG. 39 depicts a pronated foot being positioned in orthotic 3800. As the foot is positioned in orthotic 3800, the weight of the individual causes the inner follower piece 3834 (coupled to the outer coupling piece 3832) to travel in the arcuate channel 3822 such that the medial side of the heel cup pivots upwardly while the lateral side of the heel pivots downwardly causing the pronated foot to supinate or roll outwardly to a neutral position to provide the appropriate correction. FIG. 41 is a rear elevational view similar to that of FIG. 36 with an arcuate channel 3824 cut into the base layer 3812 but cut to extend toward the lateral side of the foot. As the individual positions her supinated foot in the heel cup 3818 the medial side of the heel cup pivots downwardly and the lateral side of the heel cup 3818 pivots upwardly to cause the foot to pronate or roll inwardly to a neutral position to provide the appropriate correction. Those of skill in the art will appreciate that orthotic 3800 may be dynamic such that whenever the individual steps into the heel cup the coupling piece travels in the arcuate channel as hereinbefore described. Alternatively, the inner follower piece 3834 and outer coupling piece 3832 may comprise a nut and bolt such that the coupling piece does not move but rather is fixed in one therapeutic position. If orthotic 3800 is dynamic the travel in the channel by the coupling piece is additive to the travel in the bilayer. If fixed the bilayer travels but the coupling piece in the channel does not.

Figure 42:
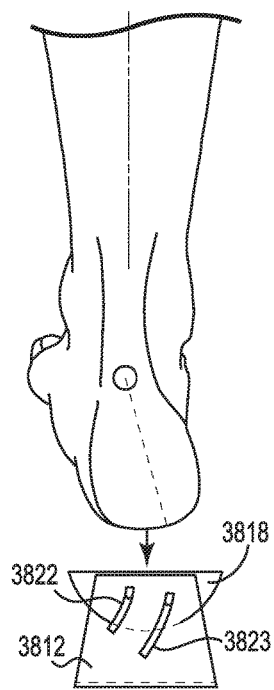
FIG. 42 is a rear elevational view of an alternative to the bi-layer orthotic of FIG. 38 but including two arcuate channels cut into a base layer thereof and showing a supinated foot descending downward into the orthotic and being supinated as the channels create a differential travel and cause a change of alignment.
Figure 43:
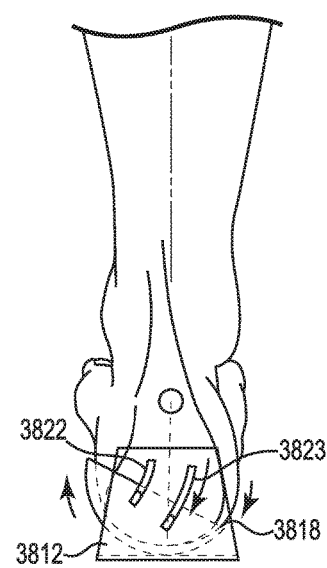
FIG. 43 is a view similar to that of FIG. 42 showing the correction of the supinated foot.
Figure 44:
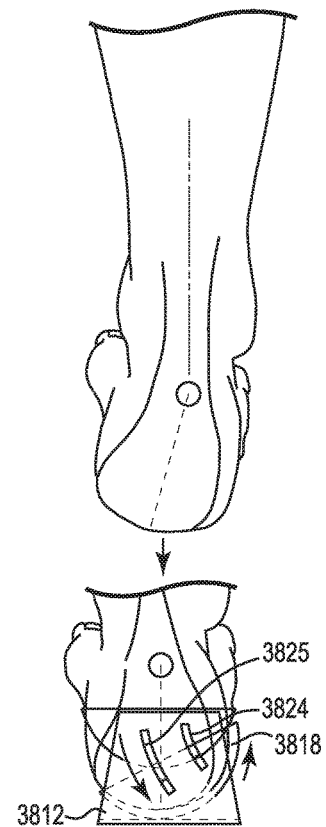
FIG. 44 is similar to the embodiment of FIGS. 42 and 43 wherein a pronated foot is shown descending and then having been corrected by the bi-layer orthotic of FIG. 42 in accordance with the invention.

FIGS. 42-44 show a variation of the arcuate channel cut into base layer 3812 of orthotic 3800. As can be seen, two arcuate channels 3822, 3823 and 3824, 3825 are cut into the base layer 3812. As best seen in FIG. 38C, arcuate rotator follower 3820 includes an outer coupling piece 3832 and two inner follower pieces 3840, 3842. The inner coupling pieces 3840, 3842 travel in channels 3822, 3818 and 3825 and 3824 respectively as the individual positions his foot in and applies weight to heel cup 3818 depending on the required correction.

FIG. 42 is a rear elevational view similar to that shown in FIG. 38 but including two arcuate channels 3822 and 3823 and showing a pronated foot descending downward into the heel cup 3822 of orthotic 3800. FIG. 43 is a view similar to that of FIG. 40 showing the correction of the pronated foot. FIG. 44 is similar to that of FIG. 41 except with two arcuate channels 3825, 3824 wherein a supinated foot is shown descending and then having been corrected to a neutral position by the bi-layer orthotic of FIG. 38 in accordance with the invention.

Figure 46:
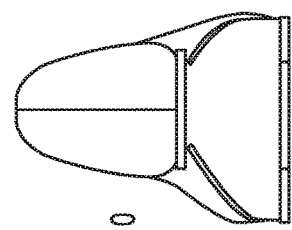
FIG. 46 is a rear elevational view thereof.
Figure 45:
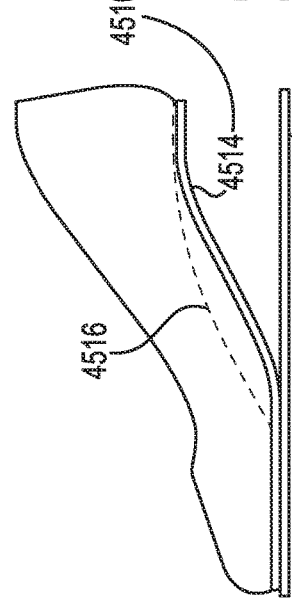
FIG. 45 is a side elevational view of a shoe built on a bi-layer or tri-layer orthotic frame with parts omitted for clarity.
Figure 47:
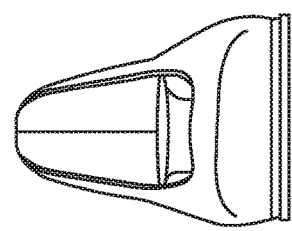
FIG. 47 is a front elevational view thereof.
Figure 48:
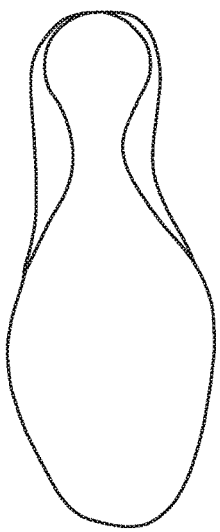
FIG. 48 is a bottom plan view thereof.
Figure 49:
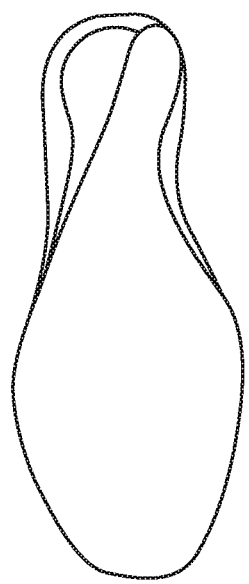
FIG. 49 is a bottom plan view of a first alternative embodiment of the bi-layer orthotic of FIGS. 45-48 in accordance with the invention.
Figure 50:
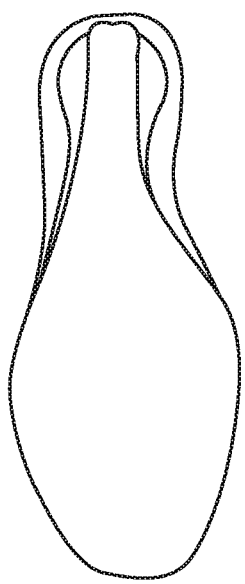
FIG. 50 is a bottom plan view of a second alternative embodiment of the bi-layer orthotic of FIGS. 45-48 in accordance with the invention.
Figure 51:
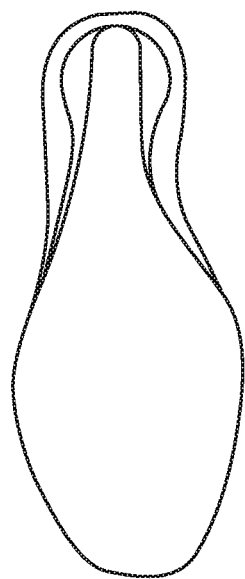
FIG. 51 is a bottom plan view of a third alternative embodiment of the bi-layer orthotic of FIGS. 45-48 in accordance with the invention.
Figure 52:
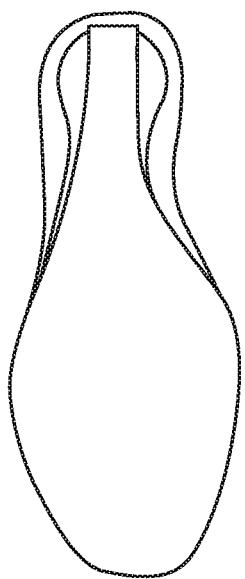
FIG. 52 is a bottom plan view of a fourth alternate embodiment of the bi-layer orthotic of FIGS. 45-48 in accordance with the invention.

FIG. 45 is a side elevational view of a shoe built on a bi-layer or tri-layer orthotic frame 4500 in accordance with the invention with an optional soft insole interface between the foot and the shoe (omitted for clarity) and especially designed for women's footwear. The function of the rear suspension spring 4510 is visible outside the confines of the shoe upper. A tri-layer version of the shoe configuration is shown in dashed line with the third layer referenced at 4516. The bottom two layers 4512, 4514 of the tri-layer energy return system or both layers of a bilayer orthotic 4512, 4514 become the "sole" of the shoe. An individual walking in a high heeled shoe no longer faces significant ankle plantar flexion at heel strike. FIG. 46 is a rear elevational view thereof. FIG. 47 is a front elevational view thereof. FIG. 48 is a bottom plan view thereof FIG. 49 is a bottom plan view of a first alternative embodiment of the bi-layer orthotic of FIGS. 45-48 in accordance with the invention. FIG. 50 is a bottom plan view of a second alternative embodiment of the bi-layer or tri-layer orthotic of FIGS. 45-48 in accordance with the invention. FIG. 51 is a bottom plan view of a third alternative embodiment of the bi-layer orthotic of FIGS. 45-48. FIG. 52 is a bottom plan view of a fourth alternative embodiment thereof. FIGS. 49-52 illustrate how the shape and width of the bottom sole layer of the shoe of FIG. 45 can vary.

Figure 53:
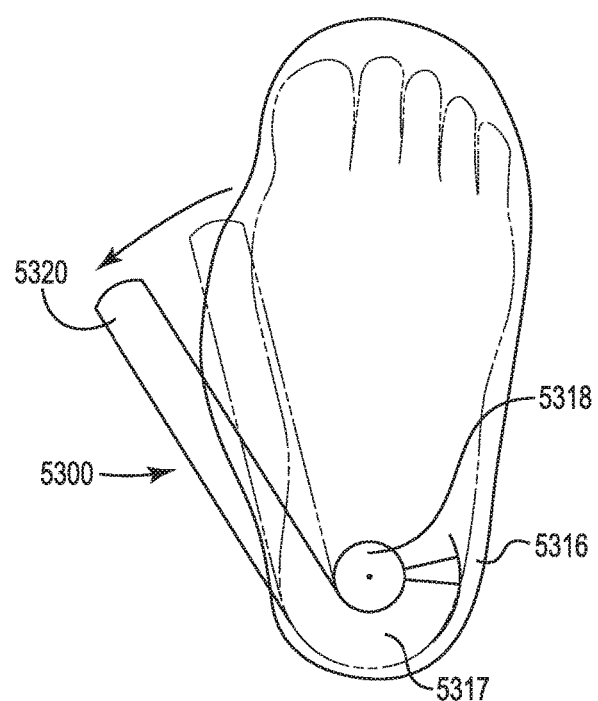
FIG. 53 is a top plan view of an alternative embodiment of an orthotic in accordance with the invention showing a kick stand strut.
Figure 54A:
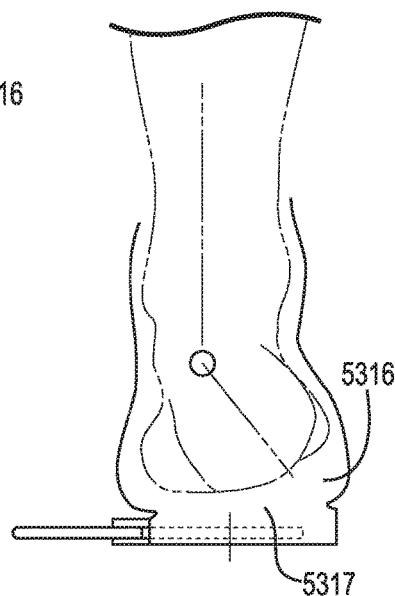
FIG. 54A is a rear view of a pronated foot showing an undeployed kick stand strut.
Figure 54B:
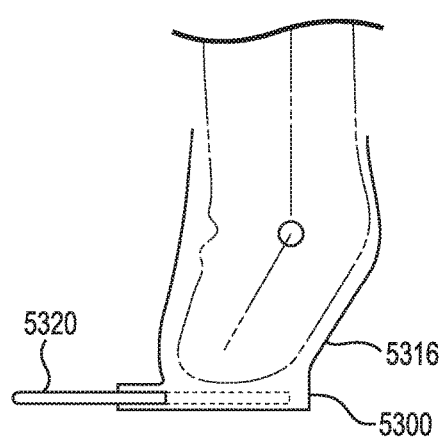
FIG. 54B is a rear view of the pronated foot of FIG. 54A being corrected (supinated) by deployed medial kickstand strut.

FIG. 53 is a top plan view of an alternative embodiment of an orthotic in accordance with the invention showing kick stand 5300. The kick stand 5300 comprises an elongate lever 5320 movable between a first position encased within orthotic 5316 and a second position outside of orthotic 5316. Elongate lever 5320 is pivotally coupled to wheel or pin 5318 at orthotic heel 5317. As seen in FIG. 54A a pronated foot requires correction. Medial movement of the elongate lever 5320 of kick stand 5300 stops pronation of foot by supinating it, as best seen in FIG. 54B. When elongate lever 5320 of kick stand 5300 is deployed the foot moves laterally, as best seen, in FIG. 54B due to the decrease in forefoot abduction. Compressibility of the bilayer orthotic allows patient tolerability of dynamic control due to shock absorption. Those of skill in the art will appreciate that elongate lever 5320 of the kick stand 5300 could be placed on the lateral side of the orthotic to correct supination.

Figures 55, 56:
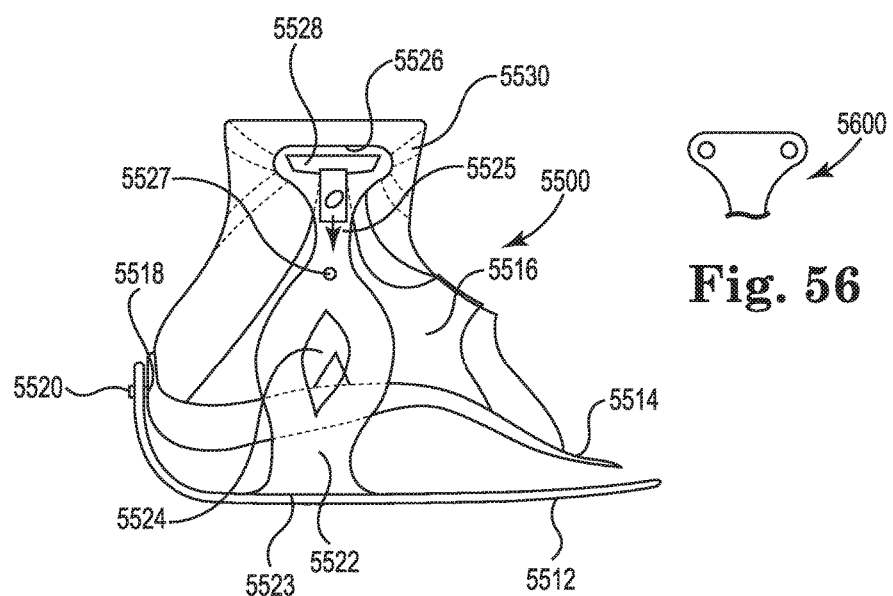
FIG. 55 is an alternative embodiment of a bi-layer orthotic in accordance with the invention for adjustable medial support of a foot with posterior tibial tendon dysfunction.
FIG. 56 is a fragmentary side elevational detail view of the part of the embodiment of FIG. 55.

Turning now to FIGS. 55-56 an alternative embodiment of the bi-layer orthotic in accordance with the invention is shown. Bi-layer orthotic 5500 broadly includes dynamic base layer 5512, orthotic 5514 and boot 5516. As can be seen base layer 5512 is operably coupled to orthotic 5514 at the heel 5518 of the orthotic by off axis rotator axel 5420. Off axis rotator axel 5520 is pivotally received by base layer 5512 and orthotic 5514 so that orthotic 5514 pivots relative to the base 5512. Dynamic base layer 5512 includes upright supports 5522 operably coupled at a first end 5523 thereto. Upright supports 5522 include cutouts 5524 for malleoli (ankle bones). Upright supports 5522 include optional hinge pin 5527 that operably couples upright support 5522 to boot 5516. Hinge pin 5527 allows for articulation if ankle range of motion is desired. Upright supports 5522 terminate at a second end 5525 with pull tab 5526.

Pull tab 5526 is fixedly coupled to boot 5516 and includes finger portion 5528 that allow a user to pull on it to facilitate easy donning of the boot 5516. Boot 5516 may optionally include tensioning straps 5530. Tensioning straps 5530 act to limit anterior/posterior displacement of the foot relative to the upright supports 5522 and are positioned such that they do not encircle the ankle or lower leg thus avoiding constriction and/or irritation of that anatomy. Tensioning straps 5530 allow another measure of control above and beyond what the bilayer orthotic can achieve alone. Boot 5516 also allows the tensioning straps to provide support that is more dispersed or spread out on the medial side of the foot and at the ankle thus decreasing tissue interface irritation and allowing tolerance of more control. FIG. 56 depicts a second pull tab 5600 that may be positioned within an upper edge of boot 5516 to facilitate donning of the boot. Second pull tab 5600 may include a neoprene like padded collar to accommodate edema and changes in leg size.

Referring now to FIGS. 57A-57D, orthotic 5700 includes upper layer 5710 (depicted as a heel cup) and may be used with a bilayer or tri-layer system. Orthotic 5700 with dynamic shim 5718 affords the potential for the foot to tolerate more correction than may be tolerated with a static shim, which when increased for more correction may often cause intolerance. Orthotic 5700 includes an upper layer 5712 and a lower layer 5714. Upper heel cup layer 5712 is fixedly coupled to lower heel cup layer 5714 at attachment point 5716. Those of skill in the art will appreciate that attachment point 5716 may be a pin or Velcro other mechanical means or may be an adhesive or bonding agent or other chemical means. Although attachment point 5716 is shown as being a single point, those of skill in the art will appreciate that the attachment may extend across the width of the orthotic 5700. As shown, shim 5718 is positioned between upper layer 5712 and lower layer 5714 and is illustrated as being positioned on the lateral side. Those of skill in the art will appreciate that shim 5718 may be positioned on a medial side of orthotic 5700 to tip the patient's heel laterally or may be positioned on the lateral side of orthotic 5700 to tip the patient's heel medially depending on the therapeutic benefit sought. Shim 5718 passively deflects upper layer 5712 (or the upper and mid-layer in the case of a tri-layer orthotic) as it compresses during the gait cycle to cause a desired alignment of the foot. The attachment point 5716 prevents the forefoot from becoming misaligned in the case of a bi-layer orthotic. This improves the alignment and reduces pathological motion in the joints.

Figure 57A:
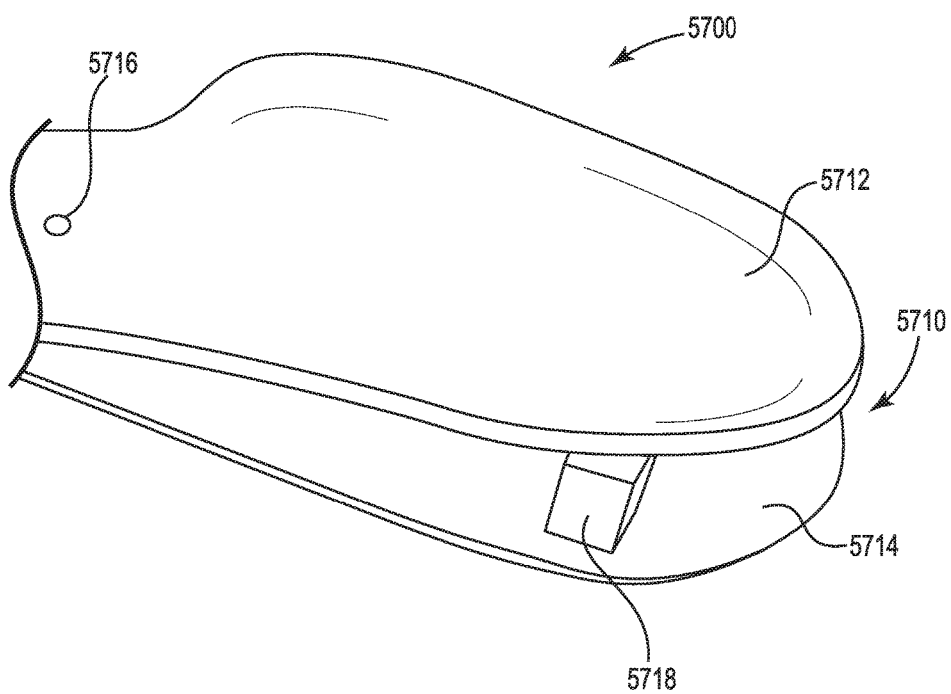
FIG. 57A is a perspective view of an orthotic showing a shim placed between two layers with the upper layer fixed to the lower or base layer at a front portion thereof.
Figure 57B:
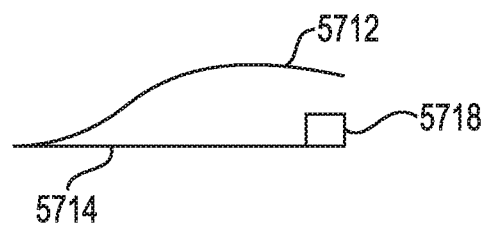
FIG. 57B is a side view of the orthotic of FIG. 57A showing placement of shim.
Figure 57C:
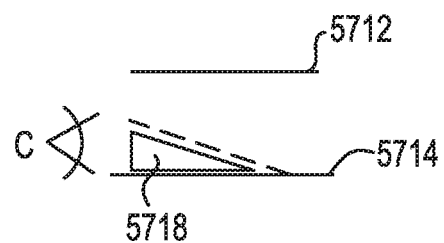
FIG. 57C is a rear view of the orthotic of FIG. 57A showing shim and the angle of correction.
Figure 57D:
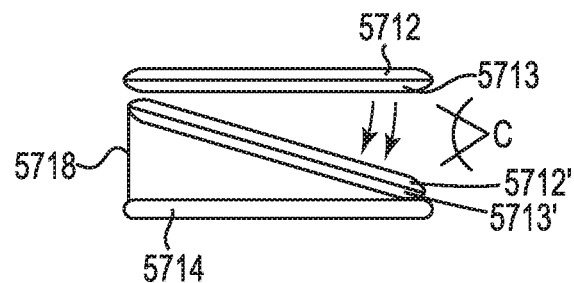
FIG. 57D is a rear view illustration of the orthotic of FIG. 57A showing the upper layer descending into lower layer and causing alignment correction; a built-in shim is positioned between the top and bottom layers.

Referring to FIG. 57D, a tri-layer system is depicted. Tri-layer system includes top layer 5712, mid-layer 5713, shim 5718 and bottom layer 5714. The shim 5718 causing alignment correction is incorporated between the mid-layer 5713 and the bottom layer 5714 such that upper layer 5712 depresses down into mid-layer 5713 and shim 5718 such that shim 5718 redirects motion and creates a new alignment of the foot as layer 5712' bottoms out on mid-layer 5713'. The angle of correction is depicted as C, the angle of the shim 5718, best seen in FIG. 57D and FIG. 57C. Those of skill in the art will also appreciate that shim 5718 may be used with and in addition to any of the orthotic systems disclosed herein. Those of skill in the art will appreciate that the tri-layer system illustrated in FIG. 57D could also function as a bi-layer system by eliminating mid-layer 5713. In such a case, the shim 5718 would be positioned between upper layer 5712 and bottom layer 5714 and upper layer 5712 would depress down into shim 5718 such that shim 5718 redirects motion and creates a new alignment of the foot as top layer 5712' bottoms out on shim 5718.

Figure 58A:
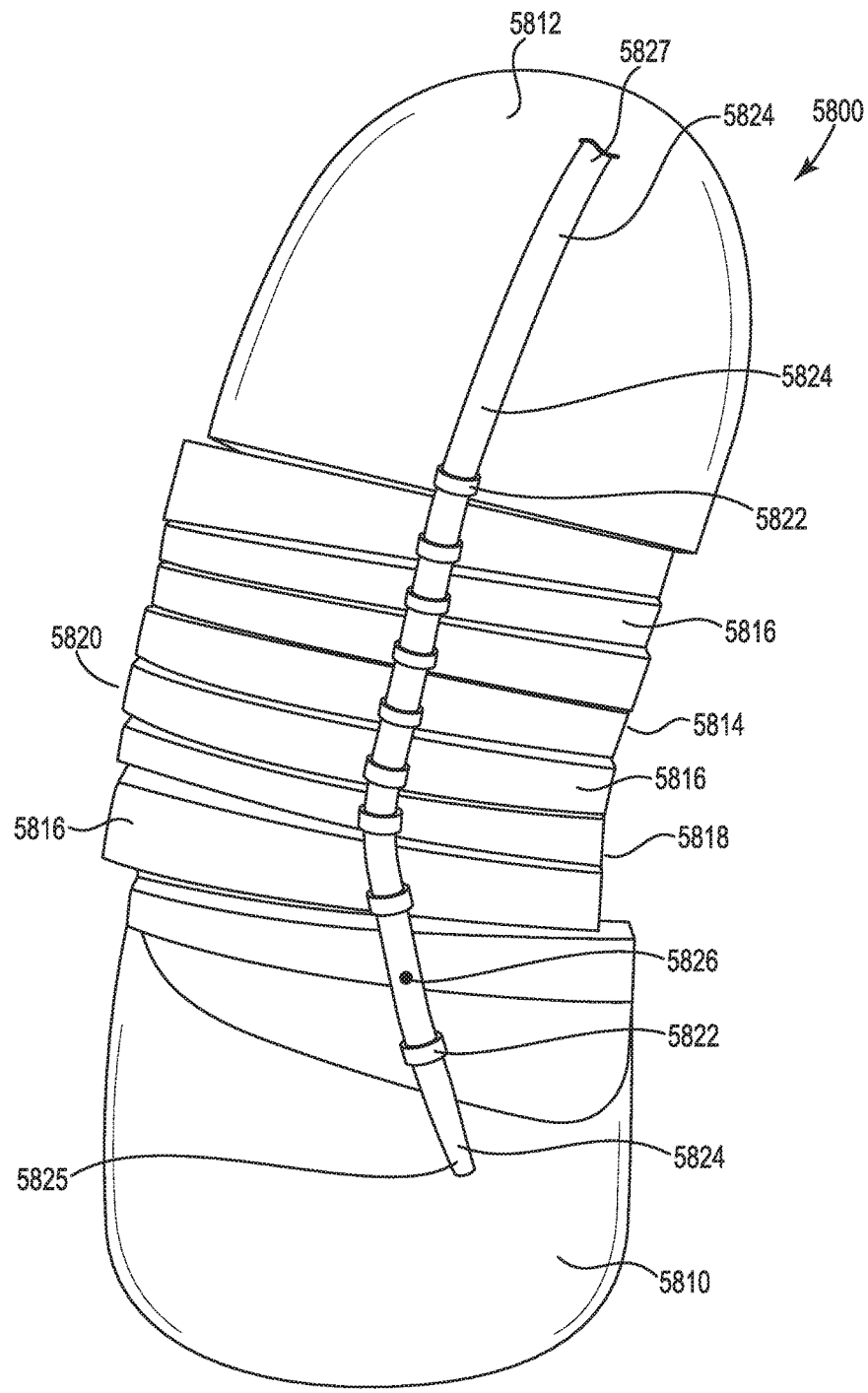
FIG. 58A is a perspective view of one aspect of the orthotic in accordance with the invention showing a bottom thereof and illustrating one or more segments cut from medial to lateral having the ability to rotate freely on an axis, which segments may be made in the top layer of a bi-layer or tri-layer orthotic any one or more of which can be deformed or shimmed according to the patient's foot pathology.
Figure 58B:
FIG. 58B is a line drawing illustrating the point of attachment of the top layer of FIG. 58A to a bi-layer orthotic.
Figure 58C:
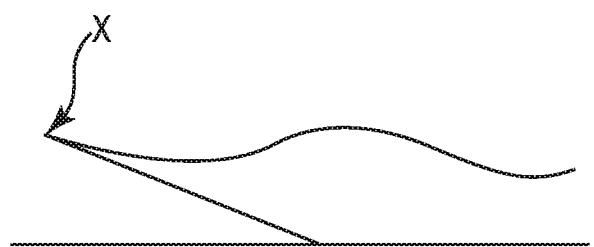
FIG. 58C is a line drawing illustrating the point of attachment of the top layer of FIG. 58A to a tri-layer orthotic.

Referring now to FIGS. 58A-58C another aspect of an orthotic system is shown. Orthotic 5800 is a top layer of a bi-layer or tri-layer orthotic (viewed from a bottom thereof) and depicts that any area of the orthotic (what used to be a solid layer of material) may be controllably adjusted. Those of skill in the art will appreciate that such a top layer is designed to be used with any of the bi-layer and tri-layer systems disclosed herein. Top layer orthotic system 5800 includes a toe portion 5810, heel portion 5812 and an arch portion 5814. At least one segment 5816 extends across the arch portion 5814 from the medial side 5818 to the lateral side 5820. Top layer orthotic system 5800 is depicted as having a plurality of segments 5816 extending across arch portion 5814 from the medial side 5818 to the lateral side 5820. Those of skill in the art will appreciate that any number of segments 5816 may be provided and may extend partially or wholly from the medial side to the lateral side or from the medial and/or lateral sides to the arch portion without departing from the scope of the invention. Each of the segments 5816 is operably coupled by connection 5822 to a semi-rigid spine 5824 that extends from the heel portion 5812 to the toe portion 5810 in this way preventing segments 5816 from separating from the orthotic 5800. Spine 5824 provides the arch shape and the rigidity to the orthotic such that the segments may be made of more resilient materials. Spine 5824 may be made of any semi-rigid material such as but not limited to PEEK (polyether ether ketone) or other organic thermoplastic polymers in the polyaryletherketone (PAEK) family. Advantageously, PEEK is a shape-memory polymer that allow it to return to the remembered shape. Spine 5824 includes a front end 5825 and a heel 5827. In a bi-layer system, shown in FIG. 58B, the front portion 5825 of spine 5824 would be coupled to the front of the base layer under the ball of the foot or just proximal to it as seen in FIG. 58B at "X." In a tri-layer system the heel end would be coupled to a mid-layer as seen in FIG. 58C at the back/heel position thereof, shown as "X." Those of skill in the art will appreciate that coupling X may comprise a fixed coupling such as by mechanical means or chemical means such as fusing the top to the bottom.

Referring again to FIG. 58A, segments 5816 are coupled to spine 5827 by connection 5822. Connection 5822 may comprise any connection or coupling known to those of skill in the art, such as band, wires, cables, pins and the like. In the case of bands, wires and cables it is desirable that the connection be flexible to allow the laterally cut segments to flex and be positioned in accordance with the pathology being treated. Connection 5822 may also comprise a pin 5826 that couples the laterally cut segments 5816 to the flexible spine 5824. In operation, one or more of the laterally cut segments 5816 may be deformed to lateral side 5820 or to medial side 5818 to accommodate different foot pathologies. In addition, some segments 5816 may be deformed to the lateral side 5820 while other segments 5816 may be deformed to the medial side 5818. Spine 5824 may comprise PEEK or other semi-rigid, shape-memory materials while segments 5812 may comprise carbon fiber or other softer materials, such as open and closed cell foams materials, known to those of skill in the art.

The top layer orthotic system 5800 depicted in FIG. 58A-58C provides the ability to control the alignment of individual segments of the orthotic that relate to specific joints or all joints of the foot. All joints can be positioned as close to neutral or normal alignment simultaneously or one or more segments may be deformed downwardly or upwardly on the lateral side by a therapeutic angle, which causes the medial side of the segment to deform in the opposite direction. Alternatively the medial side of the segment can be positioned in the neutral position. Alternatively, the medial side of one or more segments may be deformed downwardly or upwardly by a therapeutic angle, which causes the lateral side of the segment to deform in the opposite direction. Alternatively, the lateral side of the segment can be positioned in the neutral position. Top layer orthotic 5800 provides the ability to controllably move different parts of the foot to obtain proper alignment, which has not been possible with the single layer prior art orthotics. Those of skill in the art will appreciate that laterally cut segments may be made from a resilient material that allows them to be deformed or a tensioning wire or filament may be coupled by a hole placed in the laterally cut segment to deform it, as hereinbefore disclosed.

Figure 59:
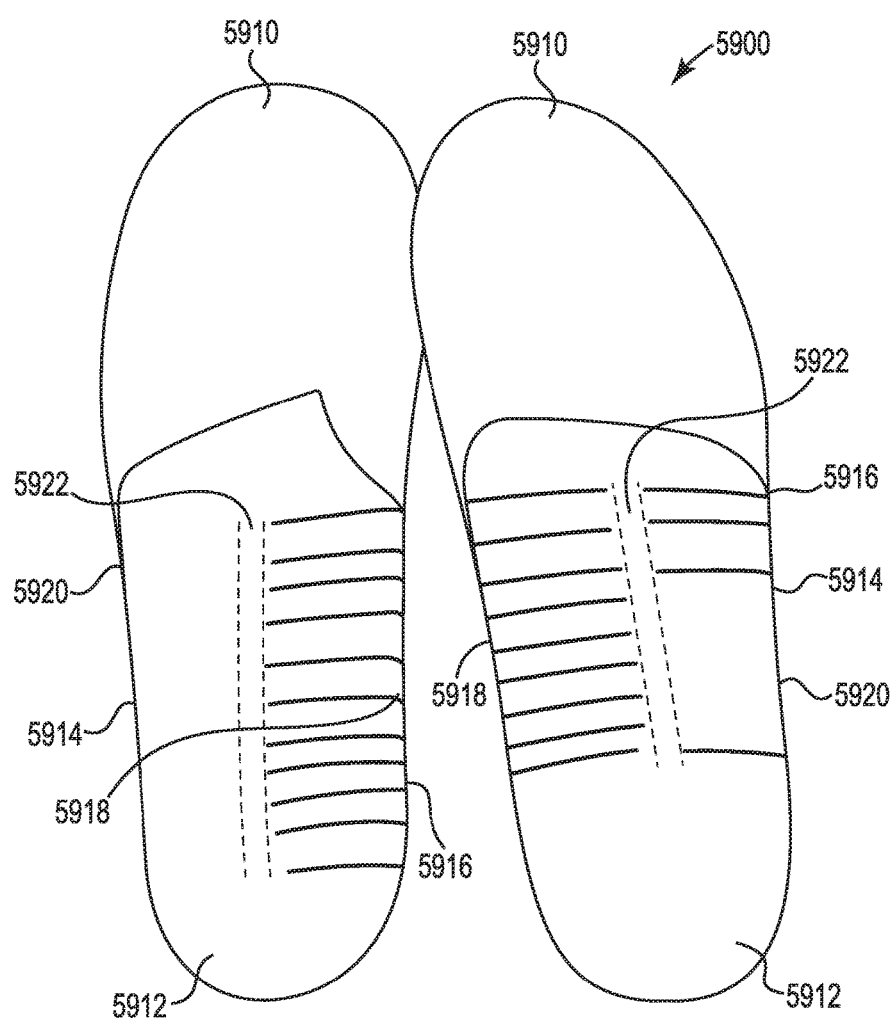
FIG. 59 is a perspective view of the orthotic of FIG. 58 illustrating two alternative patterns of segments any one or more of which can be deformed or shimmed depending on a patient's foot pathology.

Referring now to FIG. 59 an alternative to the top layer orthotic of FIG. 58 is shown. Orthotic 5900 is also a top layer orthotic designed to be used with the bi-layer and tri-layer systems disclosed herein. Orthotic 5900 generally includes a toe portion 5910, heel portion 5912, spine portion 5922 (shown in dashed lines) and arch portion 5914. At least one laterally cut segment 5916 extends across the arch portion 5914 from the medial side 5918 to the lateral side 5920. Orthotic system 5900 is depicted as having a plurality of laterally cut segments 5916 extending into the arch portion 5914 from either the medial side 5918 or the lateral side 5920. Some embodiments may include segments extending from both the medial side 5918 and the lateral side 5920. However, unlike the orthotic 5900 of FIG. 59 they do not extend entirely across the arch portion 5914 from the medial side 5918 to the lateral side 5920. This eliminates the need for a connection for coupling the segments 5916 to the toe and heel portions 5910, 5912. In that regard, spine portion 5922 is the functional equivalent of spine 5824 of top layer orthotic 5800. Those of skill in the art will appreciate that any number of laterally cut segments 5916 may be provided without departing from the scope of the invention. In operation, one or more of the laterally cut segments 5916 may be deformed to lateral side 5920 or to medial side 5918 or both to accommodate different foot pathologies. In addition, some segments 5916 may be deformed to the lateral side 5920 while other segments 5916 may be deformed to the medial side 5918 and still other segments 5916 may be deformed to both the medial and lateral sides.

Figure 60A:
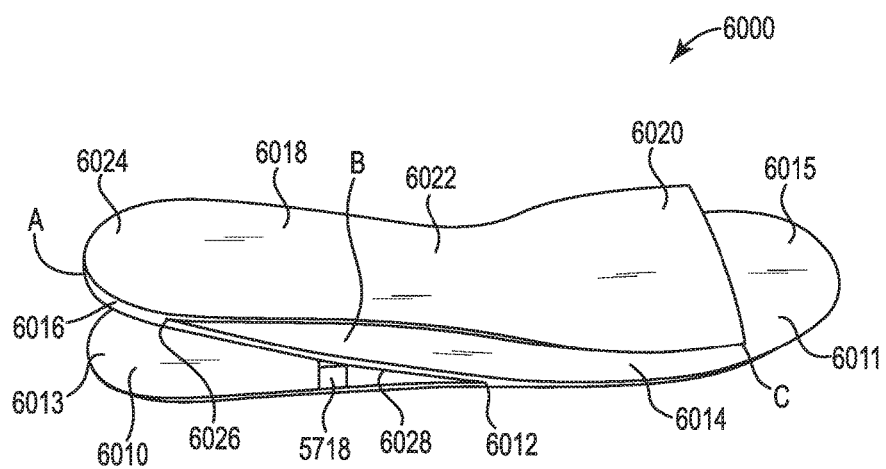
FIGS. 60A-60B are perspective views of one aspect of a basic trilayer orthotic system in accordance with the invention.
Figure 60B:
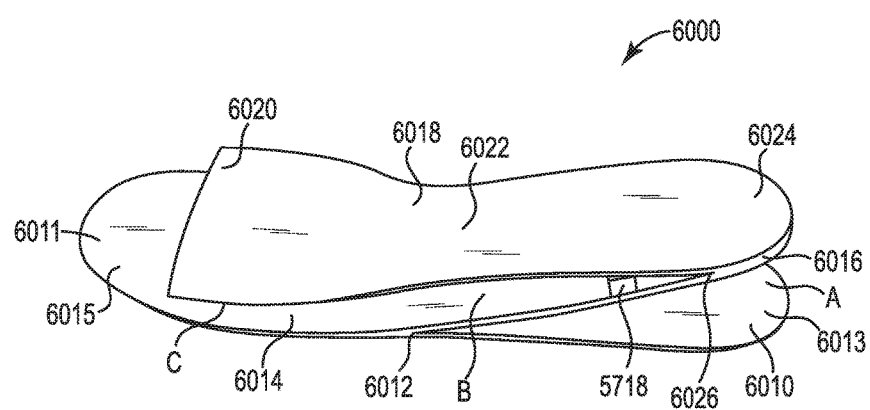

Referring now to FIGS. 60A-60B another aspect of the orthotic system in accordance with the invention is depicted. Optional shim 5718 is also depicted. Shim 5718 may be positioned between any of the layers, such as between the bottom layer and the ground, between the foot and the top layer or between the top layer and the mid-layer such that existing state orthotic correction is additive to the platform. Orthotic system 6000 forms the basis for orthotic systems depicted in FIGS. 61A through 62B. Orthotic 6000 is a tri-layer orthotic that includes three layers of material of varying thicknesses that may be laminated together in a mold with resin, or similar materials, joining the three layers together. Those of skill in the art will appreciate that tape may also be used to hold the layers together. The three layers may comprise the same materials or each layer may comprise a different material. Alternatively, two layers may comprise the same material with the base layer comprising a different material. The orthotic 6000 is layered in a mold, vacuumed formed over the mold components that separate the layers in certain areas and allow the layers to bond in other areas. The orthotic is then baked to activate and cure the resin that fuses the layers together into a single piece. The three layers may also be held together with tape and the like. The orthotic is then trimmed to appropriate sizes, i.e. size 6, 7, 8, etc. The orthotic may also be trimmed to match the foot of a particular individual user. The material may be carbon fiber or other materials known to those of skill in the art such as carbon composites, fiberglass, polypropylene and the like so long as such materials are resilient.

Alternatively, those of skill in the art will appreciate that the tri-layer orthotic may be manufactured using 3D printing. In such an embodiment, the size and shape of an orthotic may be determined based on images or other information associated with the foot requiring correction. Data about the foot may be acquired in the general context of computer-executable instructions, such as routines executed by a general-purpose computer, e.g., a server computer, wireless device, or personal computer. Those skilled in the relevant art will appreciate that the system can be practiced with other communications, data processing, or computer system configurations, including: Internet appliances, network PCs, mini-computers, mainframe computers, medical computing devices, and the like. Indeed, the terms "computer" and "computing system" are generally used interchangeably herein, and refer to any of the above devices and systems, as well as any data processor.

Aspects of the orthotic systems may be embodied in a special purpose computer or data processor that is specifically programmed, configured, or constructed to perform one or more of the computer-executable instructions or routines explained in detail herein. Aspects of the system can also be practiced in distributed computing environments where tasks or modules are performed by remote processing devices, which are linked through a communications network, such as a Local Area Network (LAN), Wide Area Network (WAN), Storage Area Network (SAN), Fibre Channel, or the Internet. In a distributed computing environment, program modules may be located in both local and remote memory storage devices.

Aspects of the orthotic systems may be stored or distributed on computer-readable media, including magnetically or optically readable computer discs, hard-wired or preprogrammed chips (e.g., EEPROM semiconductor chips), nanotechnology memory, biological memory, or other tangible data storage media. Indeed, computer implemented instructions, data structures, screen displays, and other data under aspects of the system may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme). Those skilled in the relevant art will recognize that portions of the system reside on a server computer, while corresponding portions reside on a client computer, and thus, while certain hardware platforms are described herein, aspects of the system are equally applicable to nodes on a network.

Accordingly an orthotic configuration system may receive an image or images of a foot requiring correction. The received images may be two-dimensional and/or three-dimensional images, providing information about images areas in all dimensions. For example, the image may be a partial or full image of a foot, a partial or full image of the heel area of the foot, a partial or full image of a toe area, and so on. The image may be taken using a number of different imaging techniques, such as radiological imaging (e.g., x-rays), X-Ray computed tomography (e.g. CT Scans), ultrasound, MRI or any other imaging technique or modality.

The orthotic configuration system may extract information from the received image or images. For example, the system may extract information associated with size of an affected area of the foot requiring correction. The orthotic configuration system may extract other information, such as information associated with the contour of the foot, the arch area, the heel area and/or the toe area.

The orthotic configuration system configures an orthotic that is configured to conform to the patient's foot and may generate a schematic of an orthotic based on the size and/or shape information extracted from the received images.

This information may be used to manufacture an orthotic according to the determined configuration. For example, the system manufactures an orthotic that is based on the generated schematic. Thus, the system may be utilizes to form orthotics that are optimized in size and/or shape to the area of the foot requiring correction.

Referring now to FIG. 60A AND 60B, orthotic 6000 broadly includes a base layer 6010 having a distal toe end 6011 and a proximal heel end 6013, a mid-layer portion 6014 coupled to the distal toe end 6011 of the base layer 6010 up to an approximate mid-arch point 6012. Mid-layer portion 6014 includes a distal toe portion 6015 (coupled to the distal toe end 6011 of the base layer) and a proximal heel portion 6016. Upper layer 6018 includes front upper layer portion 6020, arch upper layer portion 6022 and heel upper layer portion 6024. Heel upper layer portion 6024 is coupled to the proximal heel portion 6016 of mid-layer portion 6014. In this way all three layers 6010, 6014 and 6018 are coupled together creating three "spring" or suspension areas: rear spring section A, mid spring section B and front spring section C. Orthotic 6000 is a tri-layer orthotic that includes three layers of material of varying thicknesses that may be laminated or otherwise coupled together in a mold with resin, adhesive, or similar materials, which joins the three layers together. Those of skill in the art will appreciate that tape may also be used to hold the layers together. In one aspect, the orthotic 6100 may be vacuumed formed and baked to cure the resin and trimmed to appropriate sizes, i.e. size 6, 7, 8, etc. The orthotic may also be trimmed to match the foot of a particular individual user. The material may be carbon fiber or other materials known to those of skill in the art. Due to the characteristics of the material from which the orthotic 6000 is constructed, the upper layer 6018 is configured to be suspended over the forefoot base portion 6014. One such material may comprise carbon fiber. The heel portion 6024 of the upper layer 6018 is also configured to be suspended above the heel base portion 6010 at a therapeutic elevation angle 6028 that allows for shock absorption and cushioning as well as creating ankle dorsiflexion at heel strike that offsets ankle plantar flexion seen in normal gait at heel strike. Stored energy in the deflected material facilitates a smooth transition to mid-stance without foot slap and jarring decreasing the pronatory forces of ground impact. The elevation angle is sufficient to create enough travel for smooth shock absorption and reduction of jarring at heel strike. The elevation angle is dictated by the weight of the individual and the materials used and can be adjusted by altering the fulcrum position or adding a variable sized blocker similar to adjusting the dial on a diving board. As the toe segment dorsiflexes during forefoot loading during the gait cycle, the front upper layer portion 6020 drops causing suspension of the ball of the foot. The mid-spring section B provides suspension for the foot during mid-stance. During the gait cycle, at heel strike the rear spring section A including heel base portion 6010, proximal heel portion 6016 and heel portion 6024 provide suspension to the heel and compress at heel strike to decelerate impact and store energy. In addition, the upward curve of deflection of distal toe end 6011 during the gait cycle suspends upper layer 6018 above forefoot base portion 6014. Those of skill in the art will appreciate that materials may also be interposed between one or more layers to maintain separation of the layers. In addition, an option shim 5718 may be positioned on the medial or lateral side of the orthotic between the base layer and mid-layer or between the mid-layer and the upper layer at the junction where the layers are coupled together.

By simulating the mobile adaptor function of the foot as it attacks the ground or uneven surfaces during the gait cycle the suspension of the foot decreases the necessary reactive forces and angular deflections the body has to absorb. By functionally adding additional joint axis in appropriate areas to simulate ankle, subtalar and mid-tarsal motions, better biomechanical control of the foot and ankle may be achievable. The suspension of the foot may facilitate smoother transition of energy such that the feel of ambulation is changed to that of a smooth rolling feel without jarring and shock. Decreased pronation, supination, ankle dorsiflexion and plantar flexion required for ambulation is expected. Resultant pathological forces may be mitigated. Restorative movement from use of the device in the case of individuals requiring bracing to limit motion due to pain/arthritis or people with fused or arthrodesed joints or prosthesis should facilitate more normal function and reduce the subsequent compensatory deterioration of adjacent structures. The line of progression should straighten during gait, i.e. better alignment, resulting in decreased wear and tear on the body during gait. Less shock and jar of heel strike impact should positively influence the back and its pathologies. Control of pathological deflection of the tibia should decrease knee and hip joint wear and tear over time slowing arthritic changes.

Figure 61A:
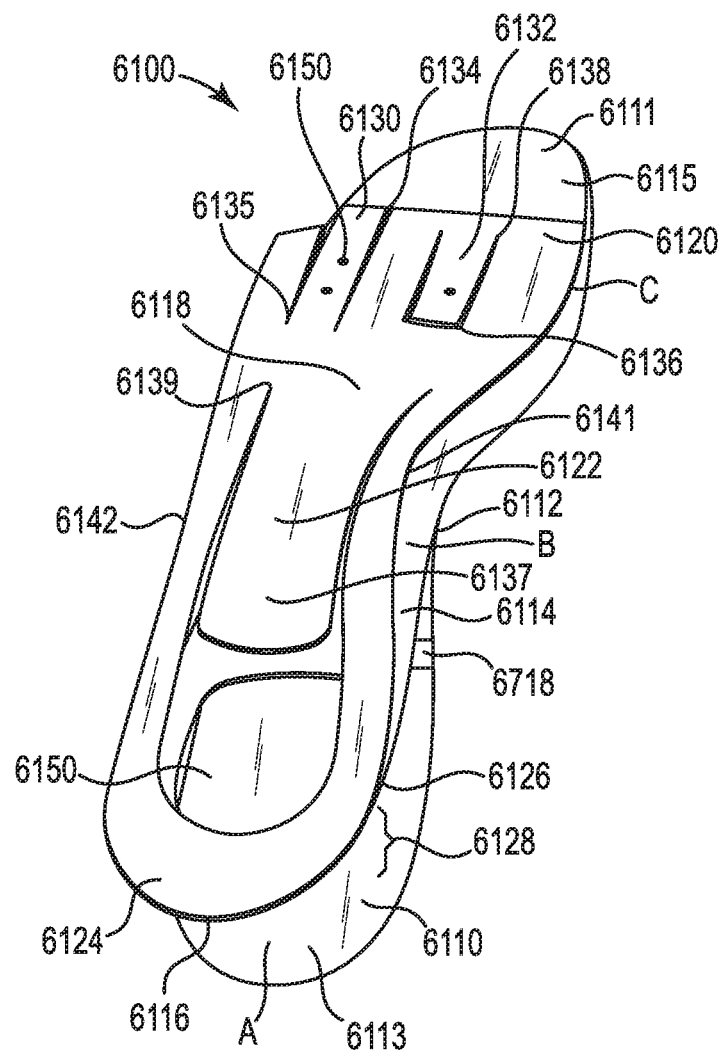
FIGS. 61A-61B are perspective views illustrating different aspects of how the basic trilayer orthotic system shown in FIGS. 60A-60B may be cut depending on a patient's foot pathology.
Figure 61B:
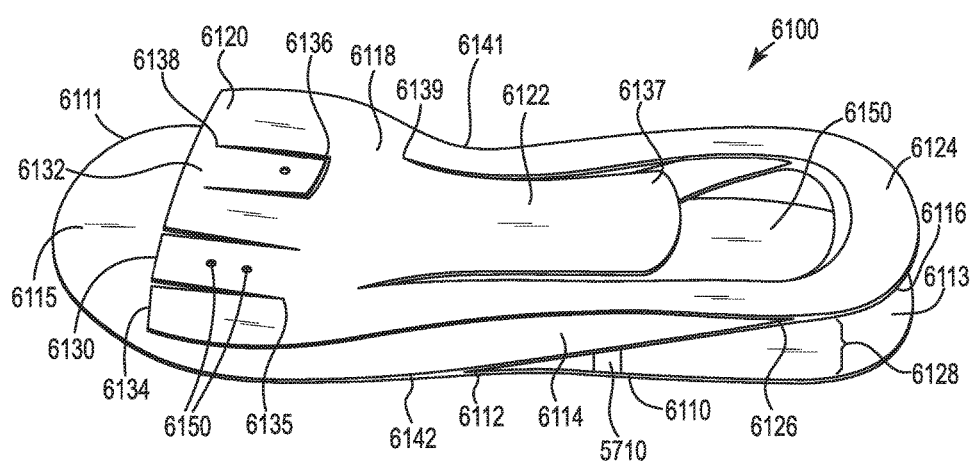

Referring now to FIGS. 61A-61B modifications to the tri-layer orthotic system 6000 depicted in FIGS. 60A-60B are shown. Optional shim 5718 is shown. Those of skill in the art will appreciate that one or more of the modifications may be made depending on the foot pathology to be corrected. Similar to orthotic 6000, orthotic 6100 is a tri-layer orthotic that includes three layers of material of varying thicknesses that may be laminated or otherwise coupled together in a mold with resin, adhesive, or similar materials, which joins the three layers together. Those of skill in the art will appreciate that tape may also be used to hold the layers together. In one aspect, the orthotic 6100 may be vacuumed formed and baked to cure the resin and trimmed to appropriate sizes, i.e. size 6, 7, 8, etc. The orthotic may also be trimmed to match the foot of a particular individual user. The material may be carbon fiber or other materials known to those of skill in the art. Orthotic 6100 broadly includes a base layer 6110 having a distal toe end 6111 and a proximal heel end 6113, a mid-layer portion 6114 fused or laminated to the distal toe end 6111 of the base layer 6110 up to an approximate mid-arch point 6112. Mid-layer portion 6114 includes a distal toe portion 6115 (fused to the distal toe end 6111 of the base layer) and a proximal heel portion 6116. Upper layer 6118 includes front upper layer portion 6120, arch upper layer portion 6122 and heel upper layer portion 6124. Heel upper layer portion 6124 is fused or laminated to the proximal heel portion 6116 of mid-layer portion 6114. In this way all three layers 6110, 6114 and 6118 are coupled together creating three "spring" or suspension areas: rear spring section A, mid spring section B and front spring section C. Due to the characteristics of the material from which the orthotic 6100 is constructed, the upper layer 6118 is configured to be suspended over the forefoot base portion 6114. Such materials may comprise carbon fiber, carbon composites, fiberglass, polypropylene and the like so long as such materials are resilient. The heel portion 6124 of the upper layer 6118 is also configured to be suspended above the heel base portion 6110 at a therapeutic elevation angle 6128 that allows for rebound recoil spring as the heel strikes the ground. The elevation angle is sufficient to create enough travel for smooth shock absorption and reduction of jarring at impact. During the gait cycle, the rear spring section A including heel base portion 6110, proximal heel portion 6116 and heel portion 6124 flex and compress at heel strike providing suspension to the heel and decelerating impact. The mid-spring section B provides suspension when the foot is flat during mid stance. As the toe segment dorsiflexes during forefoot loading during the gait cycle, the front upper layer portion 6120 drops causing suspension of the forefoot on the ball of the foot.

Front portion 6120 may include one or more segmented digit rays 6130 and 6132 cut thereinto. Those of skill in the art will appreciate that any number of segmented digit rays from one to five may be cut into the front portion. As depicted, ray 6130 is cut from a first end 6134 to a second end 6135 with the first end 6134 separated from the front portion 6120 while the second end 6135 remains operably and resiliently coupled to the front portion 6120. Ray 6130 may be deformed downwardly or upwardly during the molding process or may be deformed downwardly by attaching a filament or wire to one or more holes 6150 in the segmented digit ray and coupling it to the forefoot base portion 6115 to tension it to deflect the segmented digit ray down. If a particular ray is deformed downwardly by a therapeutic angle it achieves the remedial therapeutic goal of dynamic offloading of the metatarsals. For example, if the first segmented ray is deformed downwardly dynamic offloading of the first metatarsal-phalangeal joint occurs to treat Hallux Limitus. If the second ray is deformed downwardly stress fractures, matasalgia and the like are treated. Rays may also be tensioned downwardly to off-load an ulcer. Ray 6132 is cut in the opposite way from a first end 6136 to a second end 6138 and may be deformed downwardly or upwardly depending on the foot pathology to be treated. Those of skill in the art will appreciate that any part of the front portion 6120 may be cut to correspond to one of the five digits and deformed upwardly or downwardly.

Simple weight bearing may depress the suspension such that an unsupported segment or ray may depress during gait. Blocking depression of rays with resilient material underneath will also prevent their travel and functionally increase the corresponding pressures in that area thus offloading or redistributing pressure from adjacent areas. Alternatively a metatarsal insert segment of heat moldable or deformable materials can be dropped in a cutout window area in the suspended top layer. This would facilitate modification and offloading by thermally depressing or raising the material supported by the top layer, without requiring deflection of the rest of the device either passively with materials blocking deflection of the suspension or dynamically by means of a coupled filament that is statically adjusted and tensioned like a guitar string or dynamically tensioned by means of a lever mechanism.

Arch portion 6122 is cut into the upper layer 6118 and functions as another spring. As depicted the arch portion is cut from a proximal end 6138 to a distal end 6139 with the distal end 6139 coupled to the upper layer 6118 and the proximal end 6137 separated from the upper layer 6118. However, those of skill in the art will appreciate that the cut may be made in the opposite direction, i.e. from the distal end 6139 to the proximal end 6137 without departing from the scope of the invention. Arch portion 6122 may be deformed upwardly or downwardly depending on whether a user has high arches or flat arches but as shown is in the neutral position. Those of skill in the art will also appreciate that a shim 5718 (best seen in FIG. 57) may also be added to the medial side 6141 or lateral side 6142 of orthotic 6100 in between the heel base portion 6110 and the mid-layer portion 6114.

As seen, optional heel aperture 6150 has been cut into heel upper layer portion 6124 and mid-layer portion 6114 to off-load a potential ulcer site in a user's heel.

Figure 61C:
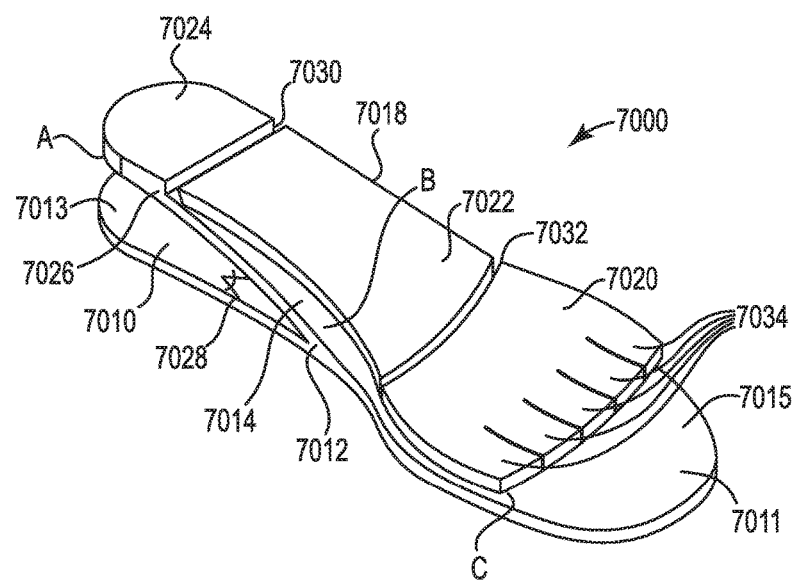
FIG. 61C is a perspective view of a variation of the trilayer orthotic system in accordance with the invention showing digit rays that may be articulated.
Figure 61D:
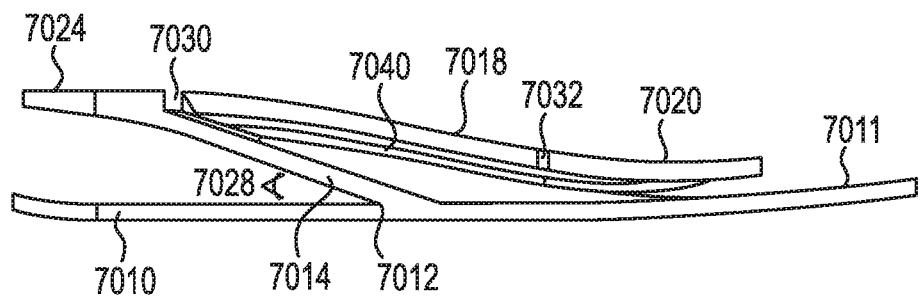
FIG. 61D is a side view of the trilayer orthotic of FIG. 61C.

Referring now to FIGS. 61C and 61D another aspect of the base tri-layer configuration seen in FIG. 60A-60B is depicted. Similar to orthotic 6000, tri-layer orthotic 7000 includes three layers of material of varying thicknesses laminated or otherwise coupled together in a mold with resin, or like materials, which joins the three layers together. The three layers may also be joined together by tape or manufactured by 3D printing as hereinbefore disclosed. Orthotic 7000 broadly includes base layer 7010, mid-layer 7014 and upper layer 7018. Base layer 7010 includes distal toe end 7011 and a proximal heel end 7013, a mid-layer portion 7014 fused or laminated to the distal toe end 7011 of the base layer 7010 up to an approximate mid-arch point 7012. Mid-layer portion 7014 includes a distal toe portion 7015 (fused to the distal toe end 7011 of the base layer) and a proximal heel portion 7016. Upper layer 7018 includes front upper layer portion 7020, arch upper layer portion 7022 and heel upper layer portion 7024. Heel upper layer portion 7024 is fused or laminated to the proximal heel portion 7016 of mid-layer portion 7014. In this way all three layers 7010, 7014 and 7018 are coupled together creating three "spring" or suspension areas: rear spring section A, mid spring section B and front spring section C. Due to the characteristics of the material from which the orthotic 7000 is constructed, the upper layer 7018 is configured to be suspended over the forefoot base portion 7014. One such material may comprise carbon fiber. Other softer, resilient materials such as open and closed cell foams may also be used as hereinafter described. The heel portion 7024 of the upper layer 7018 is also configured to be suspended above the heel base portion 7010 at a therapeutic elevation angle 7028 that allows for shock absorption and cushioning as well as creating ankle dorsiflexion at heel strike that offsets ankle plantar flexion seen in normal gait at heel strike. Stored energy in the deflected material facilitates a smooth transition to mid-stance without foot slap and jarring decreasing the pronatory forces of ground impact. The elevation angle is sufficient to create enough travel for smooth shock absorption and reduction of jarring at heel strike. The elevation angle is dictated by the weight of the individual and the materials used and can be adjusted by altering the fulcrum position similar to adjusting the dial on a diving board. As the toe segment dorsiflexes during forefoot loading during the gait cycle, the front upper layer portion 7020 drops causing suspension of the forefoot on the ball of the foot. The mid-spring section B provides suspension for the foot during mid-stance. During the gait cycle, at heel strike the rear spring section A including heel base portion 7010, proximal heel portion 7016 and heel portion 7024 provide suspension to the heel and compress at heel strike to decelerate impact and store energy. In addition, the upward curve of deflection of distal toe end 7011 during the gait cycle suspends upper layer 7018 above mid-layer 7014. Those of skill in the art will appreciate that materials may also be interposed between one or more layers to maintain separation of the layers.

Upper layer 7018 includes cuts 7030, 7032 that extend from the top of upper layer 2018 to the bottom of upper layer 2018. Cuts 7030, 7032 allow for additional flexibility of upper layer 2018 during the gait cycle. Segmented digit rays 7034 are cut into the front upper layer portion 7020 any one of which may be deflected upwardly or downwardly to correct pathologies of the toes. A deflection downwardly may be accomplished by one or more filaments that operably coupled to one or more segmented digit rays 7034 and the distal toe end 7011 of the base layer 7010. A deflection upwardly may be accomplished by the selection of materials for the upper layer.

As best seen in FIG. 61D upper layer is operably coupled to a semi-rigid spine 7040 similar to the semi-rigid spine seen in FIG. 58A. Semi-rigid spine 7040 connect the segments of the orthotic and allows for deflection of segments around the spine's axis while still controlling shape.

By simulating the mobile adaptor function of the foot as it attacks the ground or uneven surfaces during the gait cycle the suspension of the foot decreases the necessary reactive forces and angular deflections the body has to absorb. By functionally adding additional joint axis in appropriate areas to simulate ankle, subtalar and mid-tarsal motions, better biomechanical control of the foot and ankle may be achievable. The suspension of the foot may facilitate smoother transition of energy such that the feel of ambulation is changed to that of a smooth rolling feel without jarring and shock. Decreased pronation, supination, ankle dorsiflexion and plantar flexion required for ambulation is expected. Resultant pathological forces may be mitigated. Restorative movement from use of the device in the case of individuals requiring bracing to limit motion due to pain/arthritis or people with fused or arthrodesed joints or prosthesis should facilitate more normal function and reduce the subsequent compensatory deterioration of adjacent structures. The line of progression should straighten during gait, i.e. better alignment, resulting in decreased wear and tear on the body during gait. Less shock and jar of heel strike impact should positively influence the back and its pathologies. Control of pathological deflection of the tibia should decrease knee and hip joint wear and tear over time slowing arthritic changes.

Figure 62A:
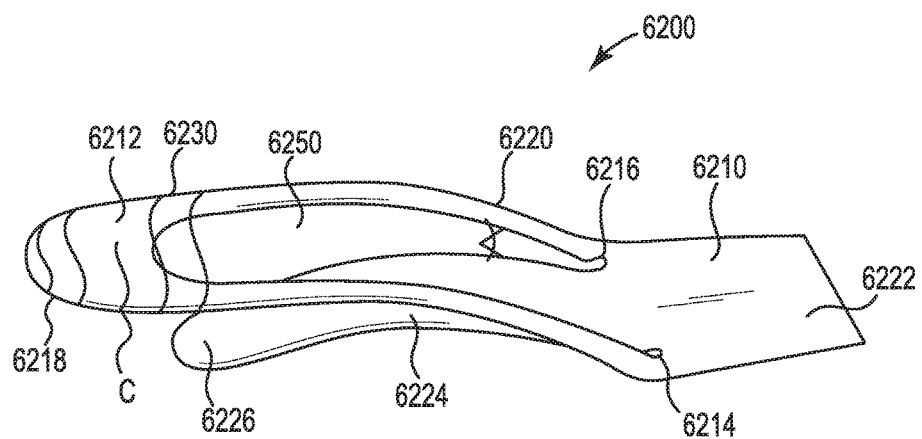
FIGS. 62A-62B are perspective views of a basic orthotic system in accordance with the invention.
Figure 62B:
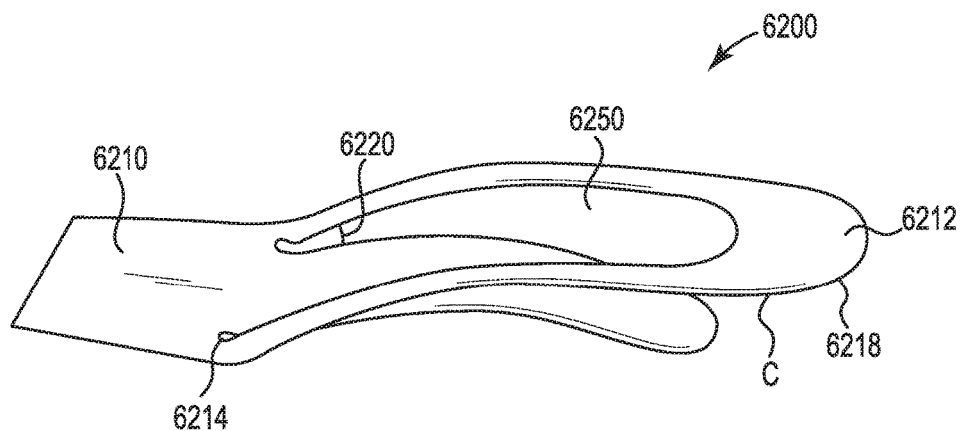

Referring now to FIGS. 62A and 62B a bi-layer orthotic constructed from a single sheet or layer of material will now be disclosed. Such a material may comprise carbon fiber, carbon composites, fiberglass, polypropylene and like materials known to those of skill in the art so long as such materials are resilient. Those of skill in the art will appreciate that orthotic 6200 and the modifications seen in FIGS. 63A-63C may be manufactured using 3D printing as hereinbefore described.

Figure 63A:
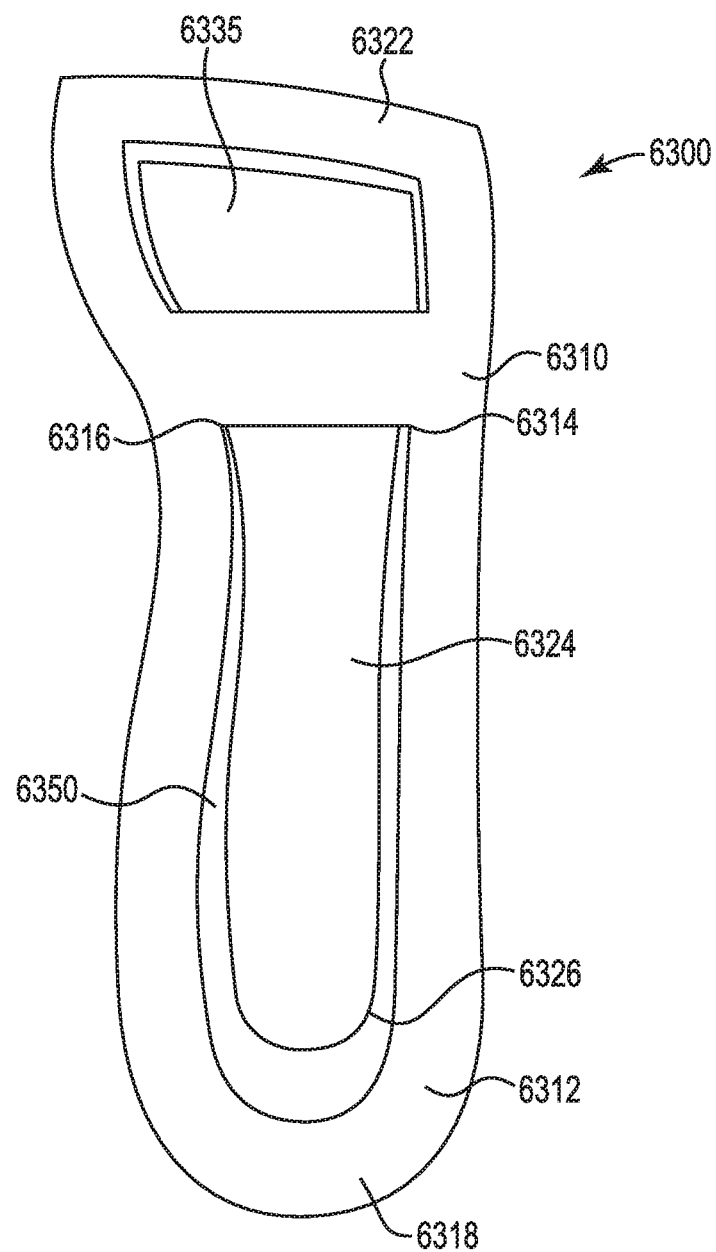
FIGS. 63A-63B are perspective views of the basic orthotic system of FIGS. 62A and 62B illustrating how the basic orthotic system may be cut and deformed depending on a patient's foot pathology.
Figure 63B:
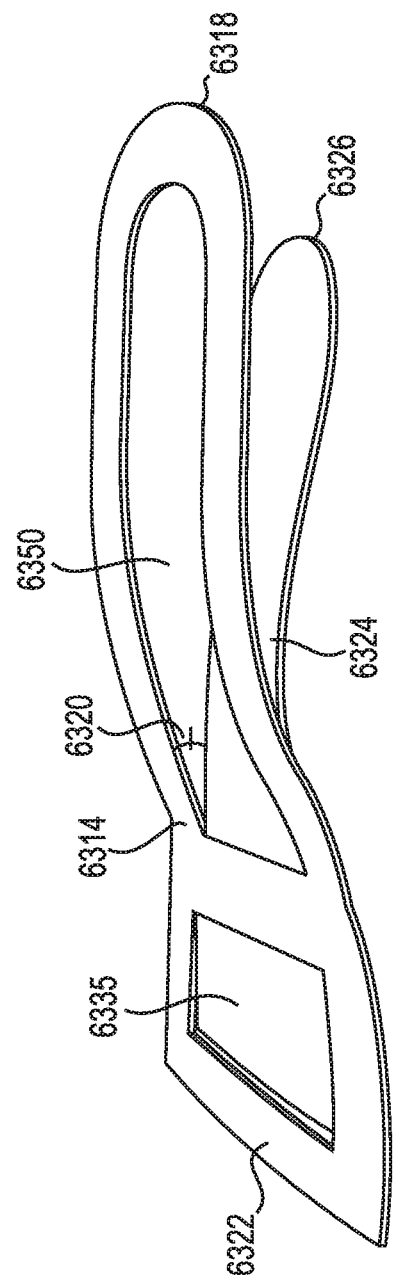
Figure 63C:
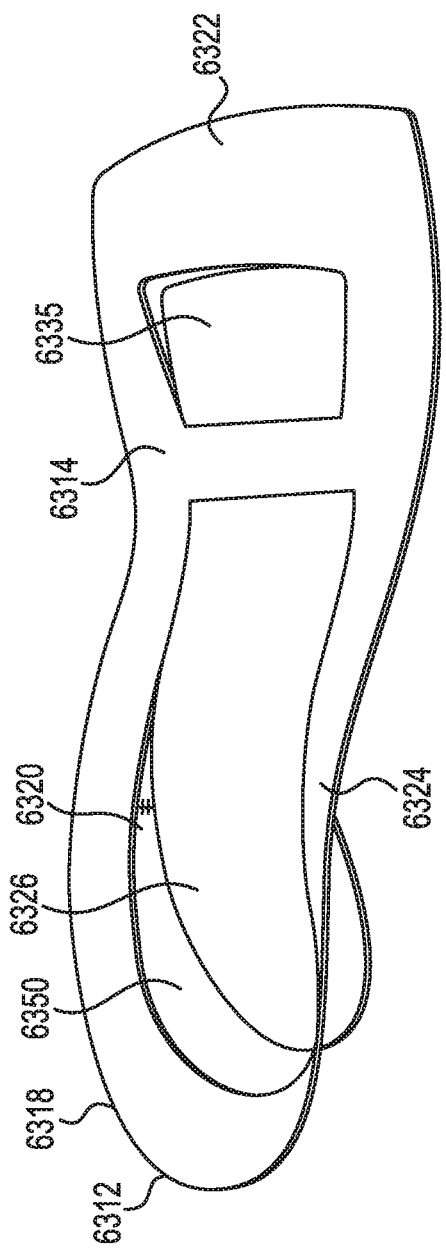
FIG. 63C is a perspective view of the orthotic of FIGS. 63A and 63B showing a modification to a heel portion thereof showing a three-dimensional conformation of shape to the heel allowing peripheral redistribution of pressures or off-loading of the central heel that normally accepts weight at impact/heel strike.

Orthotic 6200 is the base orthotic system for the modifications seen in FIGS. 63A-63C. Orthotic 6200 includes base layer 6210 and heel portion 6212. Heel portion 6212 is elevation by a therapeutic angle 6220 over base layer 6210 creating central void 6250 and forming rear spring area C. Central void 6250 off loads direct pressure on arch support structures to treat, for example, plantar fasciitis. Base layer 6210 and suspended heel portion 6212 are integrally formed from a single sheet or layer of carbon fiber, carbon composites, fiberglass, polypropylene and the like so long as such materials are resilient. Heel portion 6212 is operably coupled at a distal end 6216 thereof to base layer 6210 at attachment point 6214. Heel portion 6212 is molded to rise at a therapeutic angle 6220, which results in an elevation of the proximal end 6218 of heel portion 6212. Base layer 6210 includes a distal toe portion 6222, mid-portion 6224 and end portion 6226. Mid-portion is configured to be molded such that it is suspended from the ground with only the end portion 6226 touching the ground. Those of skill in the art will appreciate that orthotic 6200 may be covered with a flexible fabric or padding 6230 and the like such that the stretch of the fabric 6230 may suspend the foot as in a hammock between the perimeter structure of the device thus redistributing forces and pressure to areas not usually carrying load and increasing the load surface available for distribution.

Referring now to FIGS. 63A-63B various modifications of base orthotic system 6200 are depicted. Those of skill in the art will appreciate that one or more of the modifications may be made depending on the pathology of the patient's foot that requires correction. Orthotic 6300 includes base layer 6310 and heel portion 6312. Heel portion 6312 is suspended by a therapeutic angle 6320 over base layer 6310 creating central void 6350 to form rear spring area C. Base layer 6310 and suspended heel portion 6312 are formed from a single sheet of carbon fiber, carbon composites, fiberglass, polypropylene and the like so long as such materials are resilient or other suitable material and thus are integrally formed. Heel portion 6312 is integrally coupled at a distal end 6316 thereof to base layer 6310 at point 6314. Heel portion 6312 is molded to rise from a therapeutic angle 6320 that results in an elevation of the proximal end 6218 of heel portion 6312. Base layer 6310 includes a distal toe portion 6322, mid-portion 6324 and end portion 6326. Mid-portion is configured to be molded such that it is suspended from the ground with only the end portion 6326 touching the ground to form an arch. Distal toe portion 6322 has been modified to create central bi-layer area 6335, which is shown as being deformed downwardly but may also be deformed upwardly. Front bi-layer area 6335 provides suspension for the forefoot or ball of the foot similar to the rear spring area C.

Due to the resiliency of the material from which orthotic 6300 is molded, during the gait cycle the two levels in the rear 6326, 6318 and the two levels in the front 6322, 6335 constitute a suspension that travels during the gait cycle to allow shock absorption, energy return and suspension of the foot from contact on the perimeter and without direct pressure upward under the central foot and plantar fascia.

Referring now to FIG. 63C a modification to the orthotic 6300 is shown. Like areas are labeled with like reference numerals. As can be seen, proximal end 6218 of heel portion 6312 is rounded and curves upwardly to accommodate a heel. In an alternative embodiment, orthotic 6400 may be molded "upside down" so that the central bi-layer area 6335 and end portions 6326 are molded upwardly with proximal end 6318 being molded downwardly. Elevation of the central area proximal to the metatarsal head would allow for support of the transverse metatarsal.

Those of skill in the art will appreciate that orthotic 6300 may be covered with a resilient fabric or padding may be affixed to the orthotic to suspend the foot in a hammock between the more vertically oriented perimeter structure as hereinbefore disclosed. Similarly the travel in the forefoot suspension may afford similar function as well as the ability to drop in a moldable resilient insert in the window that could be modified to redistribute pressures under the foot for therapeutic benefit.

Those of skill in the art will appreciate that the disclosed embodiments in accordance with the invention are designed to accommodate numerous modifications as hereinbefore described. Thus, although the present invention has been described with reference to certain embodiments, those of ordinary skill in the art will recognize that changes may be made in form and detail without departing from the spirit and scope of the invention.

What is claimed is:

1. A bi-layer orthotic system comprising:
   a base layer having a distal toe portion, a mid-portion and a proximal end portion;
   a single upper layer integrally formed with said base layer, said upper layer having a proximal heel upper layer portion and a bi-furcated distal end, said bi-furcated distal end of said upper layer integrally coupled at first and second attachment points to the distal toe end of the base layer,
   wherein the heel upper layer portion is elevated by a therapeutic angle over said base layer to form a rear spring area.

2. The bi-layer orthotic system of claim 1 wherein said distal toe portion of the base layer includes a central bi-layer area cut into said distal toe portion.

3. The bi-layer orthotic system of claim 1 wherein said bi-furcated distal end of the heel upper layer portion is integrally formed with the distal toe portion at said attachment points.

4. The bi-layer orthotic system of claim 1 wherein a material used to construct said orthotic system is carbon fiber.

5. The bi-layer orthotic system of claim 1 further comprising a shim positioned between said distal toe portion and said upper layer.

6. The bi-layer orthotic system of claim 1 wherein said orthotic system is configured to be inserted into footwear.

7. The bi-layer orthotic system of claim 2 wherein said central bi-layer area is configured to be deformed upwardly or downwardly by a therapeutic angle.

8. The bi-layer orthotic system of claim 1 further comprising at least one sensor positioned on or near said orthotic that senses movement and/or pressure during the gait cycle; a knowledge base that provides data on a plurality of foot pathologies and a plurality of information regarding a normal foot and/or normal gait cycle; a processing device in operable communication with said at least one sensor and said knowledge base, said processing device operative to (a) receive data from said at least one sensor related to the gait cycle of an individual; (b) compare said data received from said at least one sensor to the plurality of foot pathologies in said knowledge base; (c) determine a therapeutic correction to the orthotic based on the plurality of information regarding a normal foot and/or normal gait cycle to improve the gait cycle of the individual; and (d) output a visual representation of said correction to the individual.

9. The bi-layer orthotic system of claim 1 wherein said orthotic is configured to be passively; static-dynamically or dynamic-dynamically controlled during the gait cycle to control foot, ankle and body biomechanics.

10. The bi-layer orthotic system of claim 1 wherein the elevation of said heel portion by a therapeutic angle over the base layer is configured to create a central void that off loads pressure on an arch.

11. The bi-layer orthotic system of claim 10 wherein said orthotic includes a flexible fabric or padding structured to suspend a foot over the central void.

12. The bi-layer orthotic system of claim 1 wherein said base layer mid-portion is suspended from a ground and said end portion touches the ground.

13. The bi-layer orthotic system of claim 7 wherein said bi-layer area is structured to provide suspension for a forefoot.

14. The bi-layer orthotic system of claim 1 wherein an edge of said heel upper layer portion is rounded upwardly to accommodate a heel.

\* \* \* \* \*